US011206777B2

(12) United States Patent
Baley et al.

(10) Patent No.: US 11,206,777 B2
(45) Date of Patent: Dec. 28, 2021

(54) DISEASE RESISTANT PLANT METHODS AND COMPOSITIONS

(71) Applicant: Monsanto Technology LLC, St. Louis, MO (US)

(72) Inventors: George J. Baley, St. Louis, MO (US); Derek R. Drost, Penn Valley, CA (US); Hongwu Jia, Apex, NC (US); Yule Pan, Chesterfield, MO (US); Jeffrey Michael Stein, Wildwood, MO (US); Chongqing Xie, Johnston, IA (US); Hao Zhou, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 84 days.

(21) Appl. No.: 16/831,282

(22) Filed: Mar. 26, 2020

(65) Prior Publication Data

US 2020/0305375 A1 Oct. 1, 2020

Related U.S. Application Data

(62) Division of application No. 16/404,570, filed on May 6, 2019, now Pat. No. 10,638,685, which is a division of application No. 14/801,618, filed on Jul. 16, 2015, now Pat. No. 10,280,433.

(60) Provisional application No. 62/101,292, filed on Jan. 8, 2015, provisional application No. 62/027,153, filed on Jul. 21, 2014.

(51) Int. Cl.
| | |
|---|---|
| *A01H 5/10* | (2018.01) |
| *C12Q 1/6895* | (2018.01) |
| *A01H 6/46* | (2018.01) |
| *C12Q 1/6865* | (2018.01) |

(52) U.S. Cl.
CPC .............. *A01H 5/10* (2013.01); *A01H 6/4684* (2018.05); *C12Q 1/6865* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 7,166,779 B1 | 1/2007 | Hall et al. |
| 7,414,181 B1 | 8/2008 | Eichelberger |
| 7,718,859 B2 | 5/2010 | Bockelman |

FOREIGN PATENT DOCUMENTS

WO WO 2015/088970 6/2015

OTHER PUBLICATIONS

*Zea mays* cultivar B73 chromosome 6 clone CH201-423H3, a GenBank/NCBI Accession No. AC207798, published on Sep. 23, 2013 (selected pages only).*
Carson, "Sources and Inheritance of Resistance to Anthracnose Stalk Rot of Corn," Thesis University of Illinois at Urbana-Champaign, 1980.
Chung et al., "Targeted discovery of quantitative trait loci for resistance to northern leaf blight and other diseases of maize," *Theor Appl Genet* 123:307-326, 2011.
Civardi et al., "The relationship between genetic and physical distances in the cloned *a1-sh2* interval of the *Zea mays* L. genome," *Proc. Natl. Acad. Sci. USA*; vol. 91, pp. 8268-8272; Aug. 1994.
Churchill et al., "Empirical threshold values for quantitative trait mapping," *Genetics* 138(3):963-971, 1994.
Lee et al., "Expanding the genetic map of maize with the intermated B73 x M017 (IBM) population," *Plant Mol Biol.* 48(5-6):453-461, 2002.
Andorf et al., "The Locus Lookup tool at MaizeGDB: Identification of genomic regions in maize by integrating sequence information with physical and genetic maps," *Bioinformatics* 26:434-436, 2010.
MaizeGDB Locus Record IDP7601. Available at http://www.maizegdb.org/data_center/locus?id=IDP7601. Retrieved Oct. 21, 2016.
MaizeGDB Locus Record gpm426b. Available at http://www.maizegdb.org/data_center/locus?id=gpm426b. Retrieved Oct. 21, 2016.
MaizeGDB Locus Record umc2006. Available at http://www.maizegdb.org/data_center/locus?id=umc2006. Retrieved Oct. 21, 2016.
MaizeGDB Locus Record chs562. Available at http://www.maizegdb.org/data_center/locus?id=chs562. Retrieved Oct. 21, 2016.
Schnable et al."The B73 Maize Genone: Complexity, Diversity, and Dynamics," *Science*; vol. 326; pp. 1112-1115;Nov. 20, 2009.
Wei et al., "Physical and Genetic Structure of the Maize Genome Reflects its Complex Evolutionary History," *PLOS Genetics*; vol. 3, Issue 7; e213; Jul. 2007.
*Zea mays* cultivar B73 chromosome 6 clone CH201-170P15, GenBank accession No. AC216196, published Sep. 13, 2014.
*Zea mays* cultivar RP4Htn1 hypothetical DUF630 domain protein, GenBank accession No. KR014666, published Jul. 16, 2015.

* cited by examiner

*Primary Examiner* — Bratislav Stankovic
(74) *Attorney, Agent, or Firm* — Dentons US LLP; Matthew Madsen

(57) ABSTRACT

The present invention provides methods and compositions for producing elite lines of corn exhibiting anthracnose stalk rot (ASR) resistance. Also provided in the present invention are corn plants exhibiting ASR resistance resulting from such methods, and methods for breeding corn such that the ASR resistance traits may be transferred to a desired genetic background.

7 Claims, 3 Drawing Sheets
Specification includes a Sequence Listing.

| SEQ ID | 51 | 52 | 53 | 8 | 54 | 55 | 5 | 56 | LSMean | StdDev |
|---|---|---|---|---|---|---|---|---|---|---|
| CV391950 | TT | CC | CC | GG | GG | AA | TT | AA | 2.77 | 0.96 |
| CV820914 | CC | CC | TT | CC | AA | GG | CC | GG | 6.89 | 1.11 |
| CV820914/CV391950:b |  |  |  |  |  |  |  |  | 5.22 | 0.44 |
| CV820914/CV391950:d |  |  |  |  |  |  |  |  | 5.61 | 0.53 |
| CV820914/CV391950:e |  |  |  |  |  |  |  |  | 5.87 | 0.72 |
| CV820914/CV391950:f |  |  |  |  |  |  |  |  | 4.42 | 0.58 |
| CV820914/CV391950:g |  |  |  |  |  |  |  |  | 3.44 | 0.60 |
| CV820914/CV391950:h |  |  |  |  |  |  |  |  | 2.33 | 1.10 |
| CV820914/CV391950:i |  |  |  |  |  |  |  |  | 3.66 | 0.64 |
| CV820914/CV391950:j |  |  |  |  |  |  |  |  | 2.78 | 0.58 |
| CV820914/CV391950:p |  |  |  |  |  |  |  |  | 3.20 | 0.58 |
| CV820914/CV391950:o |  |  |  |  |  |  |  |  | 3.09 | 0.55 |
| CV820914/CV391950:n |  |  |  |  |  |  |  |  | 5.22 | 0.51 |
| CV820914/CV391950:m |  |  |  |  |  |  |  |  | 5.62 | 0.68 |
| CV820914/CV391950:l |  |  |  |  |  |  |  |  | 6.25 | 0.51 |
| CV820914/CV391950:k |  |  |  |  |  |  |  |  | 5.25 | 0.64 |
| CV820914/CV391950:q |  |  |  |  |  |  |  |  | 5.01 | 0.51 |

FIG. 1

| SEQ ID | 51 | 52 | 53 | 8 | 54 | 55 | 5 | 56 | LSMean | StdDev |
|---|---|---|---|---|---|---|---|---|---|---|
| CV391950 | TT | CC | CC | GG | GG | AA | TT | AA | 2.77 | 0.96 |
| CV295879 | CC | TT | TT | CC | AA | GG | CC | GG | 7.10 | 0.96 |
| CV295879/CV391950:b | | | | | | | | | 5.26 | 0.48 |
| CV295879/CV391950:d | | | | | | | | | 6.18 | 0.60 |
| CV295879/CV391950:e | | | | | | | | | 6.12 | 0.60 |
| CV295879/CV391950:f | | | | | | | | | 4.31 | 0.68 |
| CV295879/CV391950:g | | | | | | | | | 2.92 | 0.60 |
| CV295879/CV391950:i | | | | | | | | | 4.27 | 0.58 |
| CV295879/CV391950:j | | | | | | | | | 3.34 | 0.64 |
| CV295879/CV391950:p | | | | | | | | | 3.14 | 0.53 |
| CV295879/CV391950:o | | | | | | | | | 3.54 | 0.58 |
| CV295879/CV391950:n | | | | | | | | | 5.16 | 0.51 |
| CV295879/CV391950:m | | | | | | | | | 6.12 | 0.53 |
| CV295879/CV391950:l | | | | | | | | | 4.98 | 0.49 |
| CV295879/CV391950:k | | | | | | | | | 6.60 | 0.53 |
| CV295879/CV391950:q | | | | | | | | | 4.41 | 0.61 |

FIG. 2

| SEQ ID | 4 | 81 | 82 | 53 | 83 | 8 | LSMean | StdDev |
|---|---|---|---|---|---|---|---|---|
| CV391950 | AA | TT | AA | CC | AA | GG | 1.20 | 0.45 |
| CV005260 | GG | CC | GG | TT | TT | CC | 3.80 | 1.79 |
| CV005260/CV391950:a | | | | | | | 1.10 | 0.33 |
| CV005260/CV391950:b | | | | | | | 4.90 | 1.58 |
| CV005260/CV391950:c | | | | | | | 4.50 | 1.72 |
| CV005260/CV391950:d | | | | | | | 3.40 | 1.51 |
| CV005260/CV391950:e | | | | | | | 4.11 | 1.27 |
| CV005260/CV391950:f | | | | | | | 3.50 | 1.96 |
| CV005260/CV391950:g | | | | | | | 4.20 | 1.87 |
| CV005260/CV391950:h | | | | | | | 2.00 | 1.25 |
| CV005260/CV391950:i | | | | | | | 1.10 | 0.32 |
| CV005260/CV391950:j | | | | | | | 1.20 | 0.42 |
| CV005260/CV391950:k | | | | | | | 1.20 | 0.63 |
| CV005260/CV391950:l | | | | | | | 1.00 | 0.00 |
| CV005260/CV391950:m | | | | | | | 1.90 | 0.88 |

FIG. 3

SEQUENCE LISTING

```
<160> NUMBER OF SEQ ID NOS: 106

<210> SEQ ID NO 1
<211> LENGTH: 668
<212> TYPE: DNA
<213> ORGANISM: Zea mays
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (448)..(456)
<223> OTHER INFORMATION: n is a, c, g, or t
<220> FEATURE:
<221> NAME/KEY: misc_feature
<222> LOCATION: (542)..(551)
<223> OTHER INFORMATION: n is a, c, g, or t
<220> FEATURE:
<221> NAME/KEY: misc_feature
<222> LOCATION: (565)..(576)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (580)..(585)
<223> OTHER INFORMATION: n is a, c, g, or t
<220> FEATURE:
<221> NAME/KEY: misc_feature
<222> LOCATION: (587)..(591)
<223> OTHER INFORMATION: n is a, c, g, or t
<220> FEATURE:
<221> NAME/KEY: misc_feature
<222> LOCATION: (593)..(594)
<223> OTHER INFORMATION: n is a, c, g, or t
<220> FEATURE:
<221> NAME/KEY: misc_feature
<222> LOCATION: (601)..(618)
<223> OTHER INFORMATION: n is a, c, g, or t
<220> FEATURE:
<221> NAME/KEY: misc_feature
<222> LOCATION: (623)..(631)
<223> OTHER INFORMATION: n is a, c, g, or t
<220> FEATURE:
<221> NAME/KEY: misc_feature
<222> LOCATION: (636)..(667)
<223> OTHER INFORMATION: n is a, c, g, or t

<400> SEQUENCE: 1
ccaagcccta ctgcctcaat ggtaacactt ctaataaaag caactgcgcc tgtcaaacaa      60
gaaatgaaac tgtcgttgtt agtggtatgg atgatggtgt caccatcaaa cagttcatag     120
taccactgca taatcacaat tccagcagaa atgctagctg acataatttg tatattttct     180
acactatata tctatcttta cctctttgca ttcccttgag caatttccga tccttcttgt     240
agcttttgat gggcaacgag accaactttc tggtccctga accaacagca actagtgatc     300
ttattggagg aagccctttt agcaatttgt gcacctagac aacagatact tcagttcaga     360 ctaaggggg attaattcat aaatcaagtg gaaatatagt attttctctg tatttgcaca     420
agcaaatcaa aanattatat atatattnnn nnnnnncttt ttctgctatc aagttttac     480 atgttccgtg tccctcatgc aaaagcatac atgtctgaga gtacaggtgc acaaggggag     540
```

```
annnnnnnnn nattttttaga aatgnnnnnn nnnnnntncn nnnnnannnn ntnncctatg      600
nnnnnnnnnn nnnnnnnncc cannnnnnnn ncatgnnnnn nnnnnnnnnn nnnnnnnnnn      660 nnnnnnna                                                               668
```

```
<210> SEQ ID NO 2
<211> LENGTH: 876
<212> TYPE: DNA
<213> ORGANISM: Zea mays
<220> FEATURE:
<221> NAME/KEY: misc_feature
<222> LOCATION: (381)..(381)
<223> OTHER INFORMATION: n is a, c, g, or t

<400> SEQUENCE: 2 attttttgccg gccctgtctc cggtaagacg gattccgatt ccgttgtttt cttgccaaat       60
ccttcgcagc ttgggggcgg tttcgctccg gttcttgcgc ttcggctcca ggccatggag      120
cagcggaggt ggctcgcggt agccgttttg atgtgcctgc tggtgctttg ctccgggaga      180
ggtgggttgt tggcccttct ttggtcctcc cgtttctcgc tgccggaaag gaaaaaaatt      240 gtctttttgaa tcggtttccc ctaccgtttc gtgcaagcgg actctgcctg ccggttgatt      300
ttccttagtt tatgtattgc acatttcatc agattcttat tttacccgta ccttttggat      360
tcagaactga agaccaaaca ngtgcccata tatgacccag tgctggcccg gacacttgct      420
gaatatactt ctgctgtgag ttcacctgac cttcttgatg ctgtcatcat tcacatccac      480
atccacgttg gattatgtta ttgttgaata cgtccttttt ctagtgaaat atgctgcatt      540
catcgtggag ttgaacttgg tgcttttgtg caggtctata ctgctgacct tacccaactg      600
tttacatgga catgtgagag atgttgtgac ttaacagagg tattttatat ttgtcatcac      660
catctgacat tctataattt taccaatggt tttcaaattc acatttggct tggtttgaaa      720
tcttcattaa atttatttgg tagctcaggg gttcgaggtg atagagctga ttgttgatgt      780
gaaaaattgc ttacaggtta ctgcttctgc cagtgcacct gaaccgttttt cttttttacct      840 agtaataggc ttttgattat attgatgatg atgtgt                                 876

<210> SEQ ID NO 3
<211> LENGTH: 473
<212> TYPE: DNA
<213> ORGANISM: Zea mays
<220> FEATURE:
<221> NAME/KEY: misc_feature
<222> LOCATION: (221)..(221)
<223> OTHER INFORMATION: n is a, c, g, or t

<400> SEQUENCE: 3
ggtactgaca tcataacaga atgtgcactc gccaaaagtt tttagcaatt caactctagt       60
caattcagtt gaactattgc cacaaaattc ataggtttcc accgaatgat ctccaacagc      120
aaacaggcac tgagggaggg aagcttgaac tccttgccgc aagttattgt tcaagaagtg      180
attaccaagg tttgaatcat ctgaaatatt gtttccggcg nggtagtatt catcaagttt      240
aatttgggca attgatgcct tgagccttac atttttttgga taagtctgca gatatcaaca      300
agaaaaaata tcaaatacca agcttggtga aactaaaatg atgcatggac taagaagccc      360
tgatgtacca gtaccagtac agacaaaatg aataccttgta gatcaagatg aatgttctca      420
cacttggctt tgagatgatg catatttaag ctggaagctg tagcaggaga taa             473

<210> SEQ ID NO 4
```

```
<211> LENGTH: 374
<212> TYPE: DNA
<213> ORGANISM: Zea mays
<220> FEATURE:
<221> NAME/KEY: misc_feature
<222> LOCATION: (130)..(130)
<223> OTHER INFORMATION: n is a, c, g, or t

<400> SEQUENCE: 4
tctgctgttc aagaaaatgc tggcattaaa ggtttggcct accaatgcga cgtattcttg      60
catcctgaag gtgtttgata cgcccgattt gctatccgtt ggaatgcaac ttcatggctg     120
cttgctgaan atgggaacgg aggttgacac tgctttgggg actgccttga tgacgatgta     180
tggcaggtgt ggtggagttg atgagatacc taggttggct tgtcgtataa ggcatgatgc     240
gctttcgagg actgccctgc ttggcgctta tgcacgtact ggatacaatg cagaggcaat     300
tggtgttttc aaggagatga tcatgaaaaa tatggcaatt gaccagtcag ctatgactgg     360
tatgctgcag gttt                                                      374

<210> SEQ ID NO 5
<211> LENGTH: 705
<212> TYPE: DNA
<213> ORGANISM: Zea mays
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (642)..(643)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (648)..(652)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (698)..(700)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t

<400> SEQUENCE: 5
gctccttttc aagtgccttt tgggcgtata tagtagatgg gccttataca ctttataaca      60
tcaatataaa tataattgtc tcaaattaca aatgctaaca cattccttt cttaaagata     120
```

-continued

```
tgcattacaa atccatgtta ctacctttca tttatctgac catatcaacc tatcaccacc    180
agattccaaa tattaccaac ataggtttga cagcacggaa aattaaaaag gcagctatcg    240
ttgggggtgg tctaatggga tccggaattg caacaatact gatattgaac aactttaatg    300
ttgtcttgaa agaagtaaat gaacagttct tatctgctgg cattaacaga attaaaggta    360 cactttatt tgntgcactt ttttttgga attgccttca tagttcctca gaagtttgtt     420
ctcttgtgtt cagtgaattt gcaaagtctt gtcagaaagg gtcaacttac tgaagaagat    480
tatgaaaaga ancttctct gctatgtggt gctcttgact atgaacagtt cagagataca    540
gatgtagtaa ttgaggtaga cccagtttct attatattca ccactctctg attaanatga    600
gacagcgntg cttattcagc tttgtcacct atatagagac anntancnnn nntatatcat    660
gtgcataggt ataactagtt atgtcttata acancngnnn cantc                   705
```

<210> SEQ ID NO 6
<211> LENGTH: 700
<212> TYPE: DNA
<213> ORGANISM: Zea mays
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (411)..(412)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t

<400> SEQUENCE: 6

```
cctccagtat caggtcatgc agggtcccgg tcaccacctg ccgcttggat ttgagcaccc    60
```

```
tagtaaactc caaagcggcg ccctgtacaa gaaaattctc caaatattat naactcggaa      120
gaaactcagc gtggcngtgg gggtacatac atctacggag agatgngaga tcatgccact      180
aatatgagaa aatacaagtt cnaccattaa ccgaaacgtt gattctagca aatctagtag      240
gtcactcccc caaagagttg agacctaagt ttaaggaccc ctgcaagttg atgcaactgg      300
naagcccgtt agcgaatcca tggacccaac tcttttcccc tctcgggagt gaaacttcat      360
tgacctaatt aggtggcgtc acctcgtaag tcaatgcaat tcactctctc nnatggtagt      420
acataccaag agtccacacg ctganggaat tggtatcggc aggntggaga dacgaggagg      480
gaggcgcaca cctggttctt gttgtagtgg gcgacggcga agcgagcggc gtccncggcc      540
tcggcncgct cgcggagcgc ggcgagcaca cccctcacga daccgctctc gtcccncccn      600
aggtgaaacc cggagaccgc ggcggcggag gccgcgagga gcaccgcggc gaagagaagg      660
gcgcggcgag gcatcatcgt cagcgcggcg aacctactac                           700
```

<210> SEQ ID NO 7
<211> LENGTH: 519
<212> TYPE: DNA
<213> ORGANISM: Zea mays
<220> FEATURE:
<221> NAME/KEY: misc_feature
<222> LOCATION: (463)..(463)
<223> OTHER INFORMATION: n is a, c, g, or t

<400> SEQUENCE: 7

```
caagtgaacg tcgtgcccga cttactggat tgaagcaggc agaggacata aagaagttag       60
agatgtcagc aacgccgacc acaacagtgt gtatttcatc ggtagagcaa cagggagctg      120
cttctttaag tgcgaagatt accaatgctt ctgtttctga aggacagaag aatcctggaa      180
attatatgcc ttctgccatt tcaattcccg tggggagcca tgttctgggc ctgggcgcaa      240
caagtattga agaaacaact gccactatga taactcaggc tcctgcagtt tcaaaatcag      300
aacgaagaaa acttccagga ggcagtcaac aaggtattat ttattctact cagatcatga      360
tcaattttct tggtccagat gagaagagtg gcataatctt tgctattatt ttccatggta      420
acagtaacag tggctgacat gacttgtaca tgttattgtt ttnccttttt cgtaggtatt      480
cagtttgaga gttcagcatc aaaaacaaag atggtatca                             519
```

<210> SEQ ID NO 8
<211> LENGTH: 1343
<212> TYPE: DNA
<213> ORGANISM: Zea mays
<220> FEATURE:
<221> NAME/KEY: misc_feature
<222> LOCATION: (6)..(10)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(76)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature

```
<222> LOCATION: (311)..(311)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (317)..(318)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1040)..(1040)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1282)..(1282)
<223> OTHER INFORMATION: n is a, c, g, or t
<220> FEATURE:
<221> NAME/KEY: misc_feature
<222> LOCATION: (1309)..(1311)
<223> OTHER INFORMATION: n is a, c, g, or t
<220> FEATURE:
<221> NAME/KEY: misc_feature
<222> LOCATION: (1320)..(1328)
<223> OTHER INFORMATION: n is a, c, g, or t

<400> SEQUENCE: 8
tctgtnnnnn ctatctctcc ttctccgtct ctttcttctg tgttcttcct ccattgctct      60
gtacttattn atnnnngcgc gctgccttt caancagggg caagatcctc gaggtgctca      120
agaactggcc cgagaggagc atccaggtca tcgtcgtcac cgacggcgag cgcatcctcg     180
gcctcggtga tctcggttgc caggggatgg gaattcccgt tggcaagctc tccctctaca     240
ctgccctcgg aggtgttcgc ccgtcagctg taagtgctgc tcacaatgct cnttcttcag     300
tattactact nctgntnngn aataaacttg tagcactagt cgtagtagga aagatttgga     360 atcgatttt tttcttcagt attactacta cttcagtatt attngtcgta ataatgttta     420
cgctgctgca gtgcctgccc atcacaattg atgtcggcac caacaacgag gccttgctca     480
aggacgagtt ctacatcggc ctccgccaga ggcgtgccac cggcgaggtc agcaactcat     540
ctgcaatccc ctccattgat ttagttctac ccctacatgg ctgttctgtt cacccacttg     600
cagctggtga ttttgttnaa cctgtaacca gtctcttgtc tggattattg agacgtggct     660 tgtgttttg atggttcaca ggagtaccat gaacttcttg aagagttcat gaccgccgtc     720
aagcaaaact acggcgagaa ggtcctcacc caggtcagtc tcagtggacc agccacagat     780
```

| | |
|---|---|
| actaccagct gttggttttc gccttttgg ccgaactttc tctcatcctg gatctgaaat | 840 |
| ggatgttctt tttgacctct gaccgtgcag ttcgaagact tcgccaacca caacgccttt | 900 |
| gacctgctcg agaagtacag ggagagccat ctcgtcttca acgacgatat ccaggtaggc | 960 |
| taggcttttcc ttgtgacagc gcatcacagg caaacagnag caccatggat gccaagttca | 1020 |
| gaacagggc ctgcctgttn tgtgctcgtt ccgtcgtccg tttctttcca ccgtgctgaa | 1080 |
| cgaaaacgat gcggatgtgt gtgattgctg cagggaacag cntccgtggt cctgctggc | 1140 |
| ctcctggcgg cgctcaaggt ggtcggcggg acactngcgg accacactta cctgttcctc | 1200 |
| ggcgccggcg aggtcggtcg atttgacttg ctagtatact gcatcagtgt taccctatct | 1260 |
| tttctttgcc gatcaaagct tnggatcact cgcggcctca ttcttttcnn ngattacgtn | 1320 |
| nnnnnnnnca tctgcaggcc ggg | 1343 |

<210> SEQ ID NO 9
<211> LENGTH: 402
<212> TYPE: DNA
<213> ORGANISM: Zea mays
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (389)..(394)
<223> OTHER INFORMATION: n is a, c, g, or t

<400> SEQUENCE: 9

| | |
|---|---|
| ttgaatttct ttgattccat ttcttgacag cataagcatc cacctgtgga tgtgtcctcc | 60 |
| aggagaaaac atgtgaaccc gccgagcatt catttcaaac ttcaaaatag ggccatcatg | 120 |
| gagggagaga aacgttatga cgaagtanac aaatctgtcg ctgtcaccgt cttcattacc | 180 |
| attgcctaaa gcaaaatcat cttctctgaa catcaattca gtcattgaag cccatgtgta | 240 |
| cctccatttc cttgacaaga gacatgttct tacagcttct tttattggca aacagcagag | 300 |
| aattttatct ttaataacat caggtagatt actgatgatg tcaacatttg taacagattt | 360 |
| atgtcttttc ttttgagaac ctccacgann nnngggtat ac | 402 |

<210> SEQ ID NO 10
<211> LENGTH: 584
<212> TYPE: DNA
<213> ORGANISM: Zea mays
<220> FEATURE:
<221> NAME/KEY: misc_feature
<222> LOCATION: (469)..(469)
<223> OTHER INFORMATION: n is a, c, g, or t

<400> SEQUENCE: 10

| | |
|---|---|
| agcaagaaca tactgggaaa aggtggcttt ggatacgtct acagagggca gttccctgac | 60 |
| ggaactcttg tggccgtcaa gcgactcaag gacggcaacg ccgcgggcgg cgaggcccag | 120 |
| tttcaaaccg aggtcgagat gatcagcctg gcactgcaca gaaaccttct caggctctat | 180 |
| gggttctgca tgaccgccac agagaggttg ctggtctatc catacatggc taatggaagc | 240 |
| gtcgcgtccc gcctcagagg taagcttttt tttttcttct tcttcttctc aagattccaa | 300 |
| tgtgaacttg cagtagtgca aacagattc tctcttcttc ttcggaaagt gactggaatc | 360 |
| ggattctagc tagcacttcc ttattcttcc ttccagttga caaatgttgg cacagctagc | 420 |
| agtaccacaa gcatacgatt cctatcctca ctttattcca caatgatcnc tacgcctaca | 480 |
| gggaagccac ctctggactg ggtgacgagg aagaggatag ctctcggggc agggaggggg | 540 | ctgctgtacc tgcacgagca gtgcgacccc aagatcatac acag    584

<210> SEQ ID NO 11
<211> LENGTH: 27
<212> TYPE: DNA
<213> ORGANISM: Zea mays

<400> SEQUENCE: 11
gggattaatt cataaatcaa gtggaaa    27

<210> SEQ ID NO 12
<211> LENGTH: 25
<212> TYPE: DNA
<213> ORGANISM: Zea mays

<400> SEQUENCE: 12
ccgtaccttt tggattcaga actga    25

<210> SEQ ID NO 13
<211> LENGTH: 28
<212> TYPE: DNA
<213> ORGANISM: Zea mays

<400> SEQUENCE: 13
tgttcaagaa gtgattacca aggtttga    28

<210> SEQ ID NO 14
<211> LENGTH: 23
<212> TYPE: DNA
<213> ORGANISM: Zea mays

<400> SEQUENCE: 14
cgatttgcta tccgttggaa tgc    23

<210> SEQ ID NO 15
<211> LENGTH: 25
<212> TYPE: DNA
<213> ORGANISM: Zea mays

<400> SEQUENCE: 15
tgctggcatt aacagaatta aaggt    25

<210> SEQ ID NO 16
<211> LENGTH: 22
<212> TYPE: DNA
<213> ORGANISM: Zea mays

<400> SEQUENCE: 16
tttaaggacc cctgcaagtt ga    22

<210> SEQ ID NO 17
<211> LENGTH: 25
<212> TYPE: DNA
<213> ORGANISM: Zea mays

<400> SEQUENCE: 17
acagtggctg acatgacttg tacat    25

<210> SEQ ID NO 18
<211> LENGTH: 21
<212> TYPE: DNA
<213> ORGANISM: Zea mays

```
<400> SEQUENCE: 18
tgttctgttc acccacttgc a                                              21

<210> SEQ ID NO 19
<211> LENGTH: 25
<212> TYPE: DNA
<213> ORGANISM: Zea mays

<400> SEQUENCE: 19
catcatggag ggagagaaac gttat                                          25

<210> SEQ ID NO 20
<211> LENGTH: 25
<212> TYPE: DNA
<213> ORGANISM: Zea mays

<400> SEQUENCE: 20
cagtaccaca agcatacgat tccta                                          25

<210> SEQ ID NO 21
<211> LENGTH: 26
<212> TYPE: DNA
<213> ORGANISM: Zea mays

<400> SEQUENCE: 21
acggaacatg taaaaacttg atagca                                         26

<210> SEQ ID NO 22
<211> LENGTH: 26
<212> TYPE: DNA
<213> ORGANISM: Zea mays

<400> SEQUENCE: 22
acagcagaag tatattcagc aagtgt                                         26

<210> SEQ ID NO 23
<211> LENGTH: 23
<212> TYPE: DNA
<213> ORGANISM: Zea mays

<400> SEQUENCE: 23
gtaaggctca aggcatcaat tgc                                            23

<210> SEQ ID NO 24
<211> LENGTH: 20
<212> TYPE: DNA
<213> ORGANISM: Zea mays

<400> SEQUENCE: 24
ccccaaagca gtgtcaacct                                                20

<210> SEQ ID NO 25
<211> LENGTH: 23
<212> TYPE: DNA
<213> ORGANISM: Zea mays

<400> SEQUENCE: 25
gaggaactat gaaggcaatt cca                                            23

<210> SEQ ID NO 26
<211> LENGTH: 20
<212> TYPE: DNA
<213> ORGANISM: Zea mays
```

<400> SEQUENCE: 26
ggtccatgga ttcgctaacg                                          20

<210> SEQ ID NO 27
<211> LENGTH: 26
<212> TYPE: DNA
<213> ORGANISM: Zea mays

<400> SEQUENCE: 27
gatgctgaac tctcaaactg aatacc                                   26

<210> SEQ ID NO 28
<211> LENGTH: 22
<212> TYPE: DNA
<213> ORGANISM: Zea mays

<400> SEQUENCE: 28
caagccacgt ctcaataatc ca                                       22

<210> SEQ ID NO 29
<211> LENGTH: 24
<212> TYPE: DNA
<213> ORGANISM: Zea mays

<400> SEQUENCE: 29
gcaatggtaa tgaagacggt gaca                                     24

<210> SEQ ID NO 30
<211> LENGTH: 20
<212> TYPE: DNA
<213> ORGANISM: Zea mays

<400> SEQUENCE: 30
ccagaggtgg cttccctgta                                          20

<210> SEQ ID NO 31
<211> LENGTH: 14
<212> TYPE: DNA
<213> ORGANISM: Zea mays

<400> SEQUENCE: 31
agcaaatcaa aaaa                                                14

<210> SEQ ID NO 32
<211> LENGTH: 19
<212> TYPE: DNA
<213> ORGANISM: Zea mays

<400> SEQUENCE: 32
catatatggg cacgtgttt                                           19

<210> SEQ ID NO 33
<211> LENGTH: 21
<212> TYPE: DNA
<213> ORGANISM: Zea mays

<400> SEQUENCE: 33
cttgatgaat actaccgcgc c                                        21

<210> SEQ ID NO 34
<211> LENGTH: 17
<212> TYPE: DNA

<213> ORGANISM: Zea mays

<400> SEQUENCE: 34
cttgctgaaa atgggaa                                                    17

<210> SEQ ID NO 35
<211> LENGTH: 16
<212> TYPE: DNA
<213> ORGANISM: Zea mays

<400> SEQUENCE: 35
aaaagtgcag caaata                                                     16

<210> SEQ ID NO 36
<211> LENGTH: 13
<212> TYPE: DNA
<213> ORGANISM: Zea mays

<400> SEQUENCE: 36
caactggaaa gcc                                                        13

<210> SEQ ID NO 37
<211> LENGTH: 15
<212> TYPE: DNA
<213> ORGANISM: Zea mays

<400> SEQUENCE: 37
tgttttccct ttttc                                                      15

<210> SEQ ID NO 38
<211> LENGTH: 15
<212> TYPE: DNA
<213> ORGANISM: Zea mays

<400> SEQUENCE: 38
caggttgaac aaaat                                                      15

<210> SEQ ID NO 39
<211> LENGTH: 16
<212> TYPE: DNA
<213> ORGANISM: Zea mays

<400> SEQUENCE: 39
acgaagtaaa caaatc                                                     16

<210> SEQ ID NO 40
<211> LENGTH: 18
<212> TYPE: DNA
<213> ORGANISM: Zea mays

<400> SEQUENCE: 40
cacaatgatc actacgcc                                                   18

<210> SEQ ID NO 41
<211> LENGTH: 17
<212> TYPE: DNA
<213> ORGANISM: Zea mays

<400> SEQUENCE: 41
aagcaaatca aaatatt                                                    17

<210> SEQ ID NO 42
<211> LENGTH: 18

```
<212> TYPE: DNA
<213> ORGANISM: Zea mays

<400> SEQUENCE: 42
atatatgggc acatgttt                                              18

<210> SEQ ID NO 43
<211> LENGTH: 20
<212> TYPE: DNA
<213> ORGANISM: Zea mays

<400> SEQUENCE: 43
ttgatgaata ctaccacgcc                                            20

<210> SEQ ID NO 44
<211> LENGTH: 17
<212> TYPE: DNA
<213> ORGANISM: Zea mays

<400> SEQUENCE: 44
cttgctgaag atgggaa                                               17

<210> SEQ ID NO 45
<211> LENGTH: 14
<212> TYPE: DNA
<213> ORGANISM: Zea mays

<400> SEQUENCE: 45
agtgcaacaa ataa                                                  14

<210> SEQ ID NO 46
<211> LENGTH: 14
<212> TYPE: DNA
<213> ORGANISM: Zea mays

<400> SEQUENCE: 46
tgcaactggg aagc                                                  14

<210> SEQ ID NO 47
<211> LENGTH: 17
<212> TYPE: DNA
<213> ORGANISM: Zea mays

<400> SEQUENCE: 47
ttgtttttcc tttttcg                                               17

<210> SEQ ID NO 48
<211> LENGTH: 15
<212> TYPE: DNA
<213> ORGANISM: Zea mays

<400> SEQUENCE: 48
caggttcaac aaaat                                                 15

<210> SEQ ID NO 49
<211> LENGTH: 15
<212> TYPE: DNA
<213> ORGANISM: Zea mays

<400> SEQUENCE: 49
cgaagtagac aaatc                                                 15

<210> SEQ ID NO 50
```

```
<211> LENGTH: 17
<212> TYPE: DNA
<213> ORGANISM: Zea mays

<400> SEQUENCE: 50
acaatgatcg ctacgcc                                                    17

<210> SEQ ID NO 51
<211> LENGTH: 367
<212> TYPE: DNA
<213> ORGANISM: Zea mays
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (357)..(363)
<223> OTHER INFORMATION: n is a, c, g, or t

<400> SEQUENCE: 51
gagctgtatc tgtaagcagc tgcacagtag cagcagcatc acgaacccga tgatgcagtc      60
ggtcttgtac tgcatgttgc cggcgcaacg caagtacttc gctcaggctt cccacanga     120 tccaaacagg cgcagcttct ctgctacaac agctttcatt gcctctttag cagacgccat    180
cacctgaatc aagtcctttt ctggctttct gagggacgcc aggtagctgt tccgaacctc    240
ggtgttcaca ttgaattttc tcacgcccaa gtctatgcac tcctgctcca gaaattagtg    300
cactgttata gcgcctacac gataagtttt atcctaataa tacttgagat atggccnnnn    360 nnntagc                                                              367

<210> SEQ ID NO 52
<211> LENGTH: 487
<212> TYPE: DNA
<213> ORGANISM: Zea mays
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
```

-continued

```
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (256)..(428)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t

<400> SEQUENCE: 52
actactgatg ccattggcta ccatgaaccc atggatgcag tactgcatga agcaacaggg      60
ggttgccaac ttgntagcgt ggccgaccct gatgntgcag caacngttgg cctcaccgnt     120
tcagcngtgc cagatgccaa tgatgatgcc nggtatgatg ccaccgatgn cnatgatgcc    180
gatgccgant atgatgncat cnatgatggt gccgactatg atgtcaccaa tnacgatngc    240
tagtatgatg ccnccnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420 nnnnnnnca gtgccacaat gttactctga ttcnatctcg cacattatac aacaacaaca    480
attacca                                                              487

<210> SEQ ID NO 53
<211> LENGTH: 226
<212> TYPE: DNA
<213> ORGANISM: Zea mays
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (217)..(218)
<223> OTHER INFORMATION: n is a, c, g, or t

<400> SEQUENCE: 53
tttgtcttgt tagttgttac cacatctgaa tctaacaaca ttaatccatt ccatggtgca      60
acaatataat gtaatatcat gtctctttnc cttttcttg tatgtatgtt cccaggcctt     120
cacaaatggg aaggtgataa gcgtccggca cagggtaatt gcaagctcga gcagggcgag    180
gctgtcaacg atctacttcg ctgcgccgcc actgcannca cgaatt                   226

<210> SEQ ID NO 54
<211> LENGTH: 201
<212> TYPE: DNA
<213> ORGANISM: Zea mays
<220> FEATURE:
```

```
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 54
tgcttgatac agcataaatc catcgcccag ctgaaactaa aaccaagttg tcattggcca    60
ctttattgtt tgactgcaaa gaataaaggc acgtcactca ngagaagtgc tataggaaac   120
atcaattgca ttatttatca acttatgatn tctcagaaan tagaaaatgc attgtgcgca   180
cagaccataa catgcanctg t                                             201

<210> SEQ ID NO 55
<211> LENGTH: 616
<212> TYPE: DNA
<213> ORGANISM: Zea mays
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (554)..(555)
<223> OTHER INFORMATION: n is a, c, g, or t
<220> FEATURE:
<221> NAME/KEY: misc_feature
<222> LOCATION: (565)..(566)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (589)..(593)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (604)..(612)
<223> OTHER INFORMATION: n is a, c, g, or t

<400> SEQUENCE: 55
atcttaaaag cactgaagtt atcgaacatc catatgtcca ggtaatagca gttcaactgc    60
tccagtttga ctaatattcc ctgttttatt tggagtgcta agtctctctt ttgctcctat   120
tcagatattt aatgaaggac atcaaaatgt tcttgtagag atgttggaaa tcataacagt   180
aatttgtgaa gagctcaaac tacccatagc tcagacttgg gtgccatgca aataccaaaa   240
tttattgata cattgtggtg gtgaaaataa gagttgcttc gatattcatg naagttgtgc   300
ccaagaacta tgcatgtcaa caagtgctgt tatgtttcat attatcgatg ctcatatgtg   360
gggcttccga gatgcctgtg tagagcacca cctgaagaag ggacaagggg tttctggaaa   420
ggcttttatc ctacgtaggc cttgctttac gaaagatgtt actagattct ctaaaatgga   480
gtaccccctt gttcactatg ctcgtatgtt tggattagct ggctgttttt cgatatgctt   540
```

```
gcaaagtgct tatnntagaa atgannacta tgtattgnag ttcttcttnn nnnctgattg    600
tngnnnnnnn nntgag                                                   616
```

<210> SEQ ID NO 56
<211> LENGTH: 655
<212> TYPE: DNA
<213> ORGANISM: Zea mays
<220> FEATURE:
<221> NAME/KEY: misc_feature
<222> LOCATION: (4)..(18)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (573)..(575)
<223> OTHER INFORMATION: n is a, c, g, or t
<220> FEATURE:
<221> NAME/KEY: misc_feature
<222> LOCATION: (577)..(578)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (593)..(598)
<223> OTHER INFORMATION: n is a, c, g, or t
<220> FEATURE:
<221> NAME/KEY: misc_feature
<222> LOCATION: (607)..(609)
<223> OTHER INFORMATION: n is a, c, g, or t
<220> FEATURE:
<221> NAME/KEY: misc_feature
<222> LOCATION: (618)..(623)
<223> OTHER INFORMATION: n is a, c, g, or t
<220> FEATURE:
<221> NAME/KEY: misc_feature
<222> LOCATION: (625)..(648)
<223> OTHER INFORMATION: n is a, c, g, or t

<400> SEQUENCE: 56

```
gtgnnnnnnn nnnnnnnntt ggtaactcca gctctggagt agaagatgga tgtcgagaag     60
gaacatgaaa gtagagcatc tgtaaagtta tcatagaaan ctatattcat ttttgctctg    120
gacacaagag agctatgtat tttgtataaa ttcaagagag aaaagggaga agagtaaagc    180
cacaatcatt ttaagttgcc atagagcaga atattaggtg gtcacaaaat ccaagtgacc    240
atgcagcaac gatggaacag aacaaaactc tgtaagagta aaaattaaga gtacacctgt    300
gggatttaaa tgataccgaa accacacttt ttggaactta ttttgtagaa ctaaacaaac    360
tttttttcct tcaaaaaaaa agaactaaac aaacttcggc catactatct caaagctaca    420
tgtttgcaaa aaccattagg ttggacagca actgaaaggg gtttcaaagc atgtagtttt    480
gaactacgtt aaagcaacta aactaaaagt acttcatttc atgatattgc accatgttgg    540
ttggaaggca aaagtgcaag gtaacaatgg tcnnngnngg tcctgnntgt ttnnnnnnaa    600
aaacaannnt cgtagctnnn nnncnnnnnn nnnnnnnnn nnnnnnnnag cctgc          655
```

<210> SEQ ID NO 57
<211> LENGTH: 19
<212> TYPE: DNA
<213> ORGANISM: Zea mays

<400> SEQUENCE: 57

```
ggcgcaacgc aagtacttc                                              19

<210> SEQ ID NO 58
<211> LENGTH: 22
<212> TYPE: DNA
<213> ORGANISM: Zea mays

<400> SEQUENCE: 58
tgaacccatg gatgcagtac tg                                          22

<210> SEQ ID NO 59
<211> LENGTH: 25
<212> TYPE: DNA
<213> ORGANISM: Zea mays

<400> SEQUENCE: 59
cattaatcca ttccatggtg caaca                                       25

<210> SEQ ID NO 60
<211> LENGTH: 24
<212> TYPE: DNA
<213> ORGANISM: Zea mays

<400> SEQUENCE: 60
ggccacttta ttgtttgact gcaa                                        24

<210> SEQ ID NO 61
<211> LENGTH: 25
<212> TYPE: DNA
<213> ORGANISM: Zea mays

<400> SEQUENCE: 61
gtggtggtga aaataagagt tgctt                                       25

<210> SEQ ID NO 62
<211> LENGTH: 27
<212> TYPE: DNA
<213> ORGANISM: Zea mays

<400> SEQUENCE: 62
gaaggaacat gaaagtagag catctgt                                     27

<210> SEQ ID NO 63
<211> LENGTH: 25
<212> TYPE: DNA
<213> ORGANISM: Zea mays

<400> SEQUENCE: 63
caatgaaagc tgttgtagca gagaa                                       25

<210> SEQ ID NO 64
<211> LENGTH: 21
<212> TYPE: DNA
<213> ORGANISM: Zea mays

<400> SEQUENCE: 64
ccaacagttg ctgcatcatc a                                           21

<210> SEQ ID NO 65
<211> LENGTH: 24
<212> TYPE: DNA
<213> ORGANISM: Zea mays

<400> SEQUENCE: 65
```
aaggcctggg aacatacata caag                                         24

<210> SEQ ID NO 66
<211> LENGTH: 23
<212> TYPE: DNA
<213> ORGANISM: Zea mays

<400> SEQUENCE: 66
ctgtgcgcac aatgcatttt cta                                          23

<210> SEQ ID NO 67
<211> LENGTH: 25
<212> TYPE: DNA
<213> ORGANISM: Zea mays

<400> SEQUENCE: 67
agcacttgtt gacatgcata gttct                                        25

<210> SEQ ID NO 68
<211> LENGTH: 29
<212> TYPE: DNA
<213> ORGANISM: Zea mays

<400> SEQUENCE: 68
ctcccttttc tctcttgaat ttatacaaa                                    29

<210> SEQ ID NO 69
<211> LENGTH: 14
<212> TYPE: DNA
<213> ORGANISM: Zea mays

<400> SEQUENCE: 69
cccacacgat ccaa                                                    14

<210> SEQ ID NO 70
<211> LENGTH: 14
<212> TYPE: DNA
<213> ORGANISM: Zea mays

<400> SEQUENCE: 70
acgctagcaa gttg                                                    14

<210> SEQ ID NO 71
<211> LENGTH: 18
<212> TYPE: DNA
<213> ORGANISM: Zea mays

<400> SEQUENCE: 71
atgtctcttt ccctttt                                                 18

<210> SEQ ID NO 72
<211> LENGTH: 17
<212> TYPE: DNA
<213> ORGANISM: Zea mays

<400> SEQUENCE: 72
acgtcactca ggagaag                                                 17

<210> SEQ ID NO 73
<211> LENGTH: 18
<212> TYPE: DNA
<213> ORGANISM: Zea mays

-continued

```
<400> SEQUENCE: 73
cacaactttc atgaatat                                          18

<210> SEQ ID NO 74
<211> LENGTH: 21
<212> TYPE: DNA
<213> ORGANISM: Zea mays

<400> SEQUENCE: 74
caaaaatgaa tatagttttc t                                      21

<210> SEQ ID NO 75
<211> LENGTH: 16
<212> TYPE: DNA
<213> ORGANISM: Zea mays

<400> SEQUENCE: 75
ttcccacatg atccaa                                            16

<210> SEQ ID NO 76
<211> LENGTH: 14
<212> TYPE: DNA
<213> ORGANISM: Zea mays

<400> SEQUENCE: 76
cgctaacaag ttgg                                              14

<210> SEQ ID NO 77
<211> LENGTH: 18
<212> TYPE: DNA
<213> ORGANISM: Zea mays

<400> SEQUENCE: 77
atgtctcttt tccttttt                                          18

<210> SEQ ID NO 78
<211> LENGTH: 17
<212> TYPE: DNA
<213> ORGANISM: Zea mays

<400> SEQUENCE: 78
acgtcactca agagaag                                           17

<210> SEQ ID NO 79
<211> LENGTH: 16
<212> TYPE: DNA
<213> ORGANISM: Zea mays

<400> SEQUENCE: 79
cacaacttcc atgaat                                            16

<210> SEQ ID NO 80
<211> LENGTH: 20
<212> TYPE: DNA
<213> ORGANISM: Zea mays

<400> SEQUENCE: 80
caaaaatgaa tatagctttc                                        20

<210> SEQ ID NO 81
<211> LENGTH: 201
<212> TYPE: DNA
<213> ORGANISM: Zea mays
```

-continued

<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 81
ttccatcatt gcttctntgt aggttgnggg ctcatcattg tccaacaata atatgtcatg      60
atgctctatg gctaggatta tcaactattg agttgctcga ngttcccttg tagacttatg     120
ttggactggt gcttcatcaa tagagtgcac aacatcttgt ataagttcag tgggcgctga     180 aatatttag gtgtttatcg a                                                201

<210> SEQ ID NO 82
<211> LENGTH: 201
<212> TYPE: DNA
<213> ORGANISM: Zea mays
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 82
ttaattaaaa caagtgaaat ttaatttgct nctctactca aatcgcatcg atcggtagcc      60
ccaactttga tgcaccgacc accaaagctg tcagactacg ntttgagttc cctctgctgc     120
tttaaaaaaa ctctctatca aaagatatca caagaagaat ctaatgaaac aagcttagtt     180
agtgttagac agctcacagc a                                               201

<210> SEQ ID NO 83
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 83
ggataagttt tcaggtagca aaatttgatt ccatcgggat tccagattgt tggatgagag      60
ctgacatggc aattcagact aactagtgtg ctatgtaccc ntatgttttc tttggtcttg     120
ctattatgtt tggcaaaagg atggaatggt tgagcaaata aagtaattcc agattgagaa     180
atatttncag cganggtatt c                                               201

<210> SEQ ID NO 84
<211> LENGTH: 25
<212> TYPE: DNA

<213> ORGANISM: Zea mays

<400> SEQUENCE: 84
gtcatgatgc tctatggcta ggatt 25

<210> SEQ ID NO 85
<211> LENGTH: 17
<212> TYPE: DNA
<213> ORGANISM: Zea mays

<400> SEQUENCE: 85
gcaccgacca ccaaagc 17

<210> SEQ ID NO 86
<211> LENGTH: 23
<212> TYPE: DNA
<213> ORGANISM: Zea mays

<400> SEQUENCE: 86
atgagagctg acatggcaat tca 23

<210> SEQ ID NO 87
<211> LENGTH: 24
<212> TYPE: DNA
<213> ORGANISM: Zea mays

<400> SEQUENCE: 87
gcaccagtcc aacataagtc taca 24

<210> SEQ ID NO 88
<211> LENGTH: 26
<212> TYPE: DNA
<213> ORGANISM: Zea mays

<400> SEQUENCE: 88
gagttttttt aaagcagcag agggaa 26

<210> SEQ ID NO 89
<211> LENGTH: 25
<212> TYPE: DNA
<213> ORGANISM: Zea mays

<400> SEQUENCE: 89
ccattccatc cttttgccaa acata 25

<210> SEQ ID NO 90
<211> LENGTH: 18
<212> TYPE: DNA
<213> ORGANISM: Zea mays

<400> SEQUENCE: 90
agttgctcga tgttccct 18

<210> SEQ ID NO 91
<211> LENGTH: 17
<212> TYPE: DNA
<213> ORGANISM: Zea mays

<400> SEQUENCE: 91
tcagactacg atttgag 17

<210> SEQ ID NO 92
<211> LENGTH: 20

-continued

<212> TYPE: DNA
<213> ORGANISM: Zea mays

<400> SEQUENCE: 92
tgctatgtac ccatatgttt                                          20

<210> SEQ ID NO 93
<211> LENGTH: 15
<212> TYPE: DNA
<213> ORGANISM: Zea mays

<400> SEQUENCE: 93
tgctcgacgt tccct                                               15

<210> SEQ ID NO 94
<211> LENGTH: 17
<212> TYPE: DNA
<213> ORGANISM: Zea mays

<400> SEQUENCE: 94
tcagactacg gtttgag                                             17

<210> SEQ ID NO 95
<211> LENGTH: 20
<212> TYPE: DNA
<213> ORGANISM: Zea mays

<400> SEQUENCE: 95
tgctatgtac ccttatgttt                                          20

<210> SEQ ID NO 96
<211> LENGTH: 201
<212> TYPE: DNA
<213> ORGANISM: Zea mays

<400> SEQUENCE: 96
ctgtatgaca tacatatgcc atatgacatg gccaytttca ttgtggtaaa aaaaattacg      60
tgcagtgaac agaatgttag ttagatttat gtgcagtgaa yggaatgtta gttccttagt     120
gtgcaccatc gaaatcatac tagcttcgct atttccctgt tgattttagt yggtaaaaaa     180
attctagcaa actatccggt g                                              201

<210> SEQ ID NO 97
<211> LENGTH: 301
<212> TYPE: DNA
<213> ORGANISM: Zea mays

<400> SEQUENCE: 97
gattatattt tcctttccag ttcatgcacg caaaaaattg gatggcatga gtcacataga      60
gcataaattc ttatacaaca tccaataaat acttacaaat ctggcattta tgaacataaa     120
tgatttgatt ttttatgata attacgaaca ycataaatca agaaattatc tttccaatgt     180
gtatgcaaaa aatatgcatg cagcatactg atataggaac ttcgttttca agcataaaat     240
agtacaattt ttagcgtaaa taatatatgt ggtaggcata aaatataata atcgaaaaya     300
a                                                                    301

<210> SEQ ID NO 98
<211> LENGTH: 301
<212> TYPE: DNA
<213> ORGANISM: Zea mays

```
<400> SEQUENCE: 98
aggaagctgg caatttayag gatccaccac aatgaagata tattcaaaaa tttgctgtcc    60
tcgatccagt acctcagtgg ttattcactc caaactyttt taatcgttga tgagtcatct   120
gaattcttca agaccctgga gtcaatgtcg ycatcccatc taactgacct gagagctctg   180
gagctgtctg gcaaattgct ttaccttcca aagtggctcg acactcttca acatcttgtg   240
aagttaacgc tttcagcaac agccctatgc yctgataact ttttggtcyt cagaaaactg   300
a                                                                  301

<210> SEQ ID NO 99
<211> LENGTH: 301
<212> TYPE: DNA
<213> ORGANISM: Zea mays

<400> SEQUENCE: 99
acctctatct ctactkctat aaaacaccac ttttcctggt ttctaccttg gtcccttttc    60
aaaaagtcat cacaattatt tttaatttaa ackacggtct aaacatcaac tttaacgtkc   120
acgcccaccg gtttgcacgt ttatgcaaaa ktaaggtaaa attgtgcata agkcagagtt   180
cgaacttggt tgttgtctcc aacagaacac acattttgt gctttttaa aacaaataca    240 tatggcatat agaaaccata gtgatgcacg ggcatttgac tagttaatta atatatacaa   300
c                                                                  301

<210> SEQ ID NO 100
<211> LENGTH: 301
<212> TYPE: DNA
<213> ORGANISM: Zea mays

<400> SEQUENCE: 100
ataaaccttt gttgtagtga cataaggagt ttcgaaattg caaggaattt taaatttgaa    60
tatttttcag tgagatgttg aggttgataa ttttaatctt tgtgcactaa tatgttgtag   120
aaagtagttt gttcaccgtt gcaacgcacg rgcatgtacc tagtatatat atatgaaatt   180
attgaagtgt gttatgttat tacaggatac aaatattcat gaggctcaca tgacgtgtaa   240
atatgaatca gtgccacatg aaaaagctag ttagtctaga catccaatac ggtaatatgt   300
a                                                                  301

<210> SEQ ID NO 101
<211> LENGTH: 301
<212> TYPE: DNA
<213> ORGANISM: Zea mays

<400> SEQUENCE: 101
gttcgcggtc tacgtcgtgg tgcccatgtg gcctgagggc atcccggaga gcggctccgt    60
gcaggccatc ctcgactggc agaggaggac catggagatg atgtacaccg acatcgcaca   120
ggcgatccag gccaagggka tcgacgccaa kcccagggac tacctkacct tcttctgcct   180
cggcaaccgg gaggcgaaga agccagggga gtacgtgccc acggaggagg ctgagcctga   240
cactggctac atcaaggccc agcaaaacag aaggttcatg atctatgtcc acaccaagat   300
g                                                                  301

<210> SEQ ID NO 102
<211> LENGTH: 301
<212> TYPE: DNA
<213> ORGANISM: Zea mays
```

<400> SEQUENCE: 102

```
gttcgcggtc tacgtcgtgg tgcccatgtg gcctgagggc atcccggaga gcggctccgt    60
gcaggccatc ctcgactggc agaggaggac catggagatg atgtacaccg acatcgcaca   120
ggcgatccag gccaagggma tcgacgccaa mcccagggac tacctmacct tcttctgcct   180
cggcaaccgg gaggcgaaga agccagggga gtacgtgccc acggaggagg ctgagcctga   240
cactggctac atcaaggccc agcaaaacag aaggttcatg atctatgtcc acaccaagat   300
g                                                                   301
```

<210> SEQ ID NO 103
<211> LENGTH: 301
<212> TYPE: DNA
<213> ORGANISM: Zea mays

<400> SEQUENCE: 103

```
tggaaggtcc accccctcct cctcctctcc ccaaatcgtg catccgccgc gccctcaaat    60
cccgctggcc ttcaactcta tctctgcagc ggatgcgccc gcggatggaa ggtaccagac   120
ctcttctcgc cattaccgcg cccgccccgt yaattcccat atctcttctc gccatcctct   180
cggatcgtcc actgccattc atggacggca gccgattcca tcctctcggt tcatggacag   240
caaacttgta tctatttaaa aaccctaat cgatccatac gccatatgcc agtgaagcca    300
c                                                                   301
```

<210> SEQ ID NO 104
<211> LENGTH: 301
<212> TYPE: DNA
<213> ORGANISM: Zea mays

<400> SEQUENCE: 104

```
actctcctac atcatcacca ttgcaaagta cgggccaaca aaacacaaca agargarctg    60
gatcgggcac accgcacaca gggatctctg aagcttaccc gatggagaag gtggtcatgg   120
agctatcctc cgtcgtcggt gtagagcgtc rcgctgtggg tcgtgaagac ccgggaatcg   180
aggggggtcat cgcgagcggc gtcaggcagg tggatgacgg crgctgtctc gcaggcgggt   240
aggcaagggg gacgggtgcg gcggtccctg aggggatgac gatgcatgcg ggggttgaga   300
a                                                                   301
```

<210> SEQ ID NO 105
<211> LENGTH: 301
<212> TYPE: DNA
<213> ORGANISM: Zea mays

<400> SEQUENCE: 105

```
gcccataaag atctctgatg tgtactcgtc catagccctc ttactatctc ccacgtacgg    60
cacatactgc atgcaacaaa tgagtggcaa gtttcaatgt aaatctacgt ttaaactgct   120
gcatgtgcca tctttttaaa gaggtggaag wtcagctaac agaccttgat gacaacaaca   180
tgatcgggat gctcgccggg cccatagaga atggcattgc ttgagacaat gtcatccacc   240
acgttgctct tggagatctc cttggacctg aatgtttgag gggcagacag gttcatgccg   300
t                                                                   301
```

<210> SEQ ID NO 106
<211> LENGTH: 301
<212> TYPE: DNA

```
<213> ORGANISM: Zea mays

<400> SEQUENCE: 106
atacccgaag ccatgcttag catagtaggg gaggttggag agcgtcgtct catcgacgtc     60
gaacacccag acctccttgc cttggccggt gaggttgagg ccctcggcgt aggcgatggc    120
ctcgttggcg acggctcggg agtcgctgcg rtagtgcccg ccgagcatgt agttgccgac    180
gtacttctcg cagcgggctg ggacagtgtc ccagtcgcgg agggtgttgg tctccacagc    240
gaaccgccag ctgtcgcacg gcacgcggcc gcgccggccg aggtcgccgc crgaatgcag    300
c                                                                   301
```

DISEASE RESISTANT PLANT METHODS AND COMPOSITIONS

REFERENCE TO RELATED APPLICATIONS

This application is a divisional of U.S. application Ser. No. 16/404,570, filed May 6, 2019, which is a divisional of U.S. application Ser. No. 14/801,618, filed Jul. 16, 2015, now U.S. Pat. No. 10,280,433, which claims the benefit of U.S. Provisional Application No. 62/027,153, filed Jul. 21, 2014, and U.S. Provisional Application No. 62/101,292, filed Jan. 8, 2015 each of which is herein incorporated by reference in their entireties.

FIELD OF THE INVENTION

The present invention relates to the field of agricultural biotechnology. More specifically, the invention relates to methods for producing corn plants with resistance to fungi.

INCORPORATION OF SEQUENCE LISTING

A sequence listing contained in the file named "MONS358US_ST25.txt" which is 40 bytes (measured in MS-Windows®) and created on Jul. 16, 2015, and comprises 106 nucleotide sequences, is filed electronically herewith and incorporated by reference in its entirety.

BACKGROUND OF THE INVENTION

Advances in molecular genetics have made it possible to select plants based on genetic markers linked to traits of interest, a process called marker-assisted selection (MAS). While breeding efforts to date have provided a number of useful corn lines and varieties with beneficial traits, there remains a need in the art for selection of varieties with further improved traits and methods for their production. In many cases, such efforts have been hampered by difficulties in identifying and using alleles conferring beneficial traits. These efforts can be confounded by the lack of definitive phenotypic assays, and other issues such as epistasis and polygenic or quantitative inheritance. In the absence of molecular tools such as MAS, it may not be practical to attempt to produce certain new genotypes of crop plants due to such challenges.

SUMMARY OF THE INVENTION

In one aspect, the present invention provides a method for obtaining a corn plant with enhanced anthracnose stalk rot resistance comprising: a) providing a population of corn plants; b) detecting in said plants an anthracnose stalk rot resistance allele at a polymorphic locus in a chromosomal segment flanked by loci IDP7601 and gpm426b on chromosome 6; c) selecting from said population at least a first plant comprising said allele and enhanced anthracnose stalk rot resistance compared to a plant lacking said allele. In some embodiments, said segment is flanked by marker loci umc2006 and chs562. In other embodiments, said segment is flanked by marker loci umc2006 and SEQ ID NO: 8. In further embodiments, said segment is flanked by marker loci SEQ ID NO: 52 and SEQ ID NO: 8. In yet further embodiments, said segment is flanked by marker loci SEQ ID NO: 4 and SEQ ID NO: 2. In other embodiments, said segment is flanked by marker loci SEQ ID NO: 96 and SEQ ID NO: 106. In some embodiments, said polymorphic locus is selected from the group consisting of: IDP7601, IDP62, 111, IDP8090, umc2006, IDP8231, umc248b, SEQ ID NO: 10, pco136292, SEQ ID NO: 3, IDP6025, IDP6010, SEQ ID NO: 1, SEQ ID NO: 7, agrr118a, umc180(pep), SEQ ID NO: 51, gpm74, TIDP3136, AY107053, SEQ ID NO: 4, SEQ ID NO: 52, IDP1699, pdi7, gpm869, SEQ ID NO: 81, ufg11, SEQ ID NO: 82, umc1250, SEQ ID NO: 53, TIDP3356, SEQ ID NO: 83, SEQ ID NO: 96, csu382a(cld), IDP2409, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, PCO146525, SEQ ID NO: 8, csu225, bn13.03, AI665560, SEQ ID NO: 54, pzb00414, umc2141, SEQ ID NO: 55, SEQ ID NO: 2, AY110435, e1fa5, SEQ ID NO: 5, umc1379, bn115.37a, SEQ ID NO: 56, pza02478, IDP3886, c139957_1, mmc0241, dup400(pac), jpsb107b, chs562, gpm709b, SEQ ID NO: 6, umc2321, bn1g1702, SEQ ID NO: 9, csu158b(eno), and gpm426b. In further embodiments, the invention provides a corn plant produced by the methods provided herein, or a plant part or seed of said corn plant.

In another aspect, the present invention provides a method of producing a corn plant with enhanced anthracnose stalk rot resistance comprising: a) introgressing into a corn plant a genomic segment comprising an anthracnose stalk rot resistance allele; and b) selecting a plant based on the presence of said allele in at least one polymorphic locus selected from the group consisting of: IDP7601, IDP62, 111, IDP8090, umc2006, IDP8231, umc248b, SEQ ID NO: 10, pco136292, SEQ ID NO: 3, IDP6025, IDP6010, SEQ ID NO: 1, SEQ ID NO: 7, agrr118a, umc180(pep), SEQ ID NO: 51, gpm74, TIDP3136, AY107053, SEQ ID NO: 4, SEQ ID NO: 52, IDP1699, pdi7, gpm869, SEQ ID NO: 81, ufg11, SEQ ID NO: 82, umc1250, SEQ ID NO: 53, TIDP3356, SEQ ID NO: 83, SEQ ID NO: 96, csu382a(cld), IDP2409, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, PC0146525, SEQ ID NO: 8, csu225, bn13.03, AI665560, SEQ ID NO: 54, pzb00414, umc2141, SEQ ID NO: 55, SEQ ID NO: 2, AY110435, e1fa5, SEQ ID NO: 5, umc1379, bn115.37a, SEQ ID NO: 56, pza02478, IDP3886, c139957_1, mmc0241, dup400(pac), jpsb107b, chs562, gpm709b, SEQ ID NO: 6, umc2321, bn1g1702, SEQ ID NO: 9, csu158b(eno), and gpm426b; wherein said allele confers enhanced resistance to anthracnose stalk rot compared to a plant lacking said allele. In further embodiments, the method further comprises: c) crossing said corn plant with itself or a second plant to produce one or more progeny plants; and d) selecting a progeny plant comprising said allele. In some embodiments, step (d) of selecting comprises marker-assisted selection. In other embodiments, the progeny plant is an F2-F6 progeny plant. In further embodiments, producing the progeny plant comprises backcrossing. In yet further embodiments, backcrossing comprises from 2-7 generations of backcrosses. In certain embodiments, backcrossing comprises marker-assisted selection in at least two generations. In further embodiments, the invention provides a corn plant produced by the methods provided herein, or a plant part or seed of said corn plant.

In yet another aspect, the invention provides a method of producing a corn plant with enhanced anthracnose stalk rot resistance comprising: a) crossing a first corn plant comprising an anthracnose stalk rot resistance allele with a second corn plant of a different genotype to produce one or more progeny plants; and b) selecting a progeny plant based on the presence of said allele in at least one polymorphic locus selected from the group consisting of: IDP7601, IDP62, 111, IDP8090, umc2006, IDP8231, umc248b, SEQ ID NO: 10, pco136292, SEQ ID NO: 3, IDP6025, IDP6010, SEQ ID NO: 1, SEQ ID NO: 7, agrr118a, umc180(pep), SEQ ID NO: 51, gpm74, TIDP3136, AY107053, SEQ ID NO: 4, SEQ ID NO: 52, IDP1699, pdi7, gpm869, SEQ ID NO: 81, ufg11, SEQ ID NO: 82, umc1250, SEQ ID NO: 53, TIDP3356, SEQ ID NO: 83, SEQ ID NO: 96, csu382a(cld), IDP2409, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, PCO146525, SEQ ID NO: 8, csu225, bn13.03, AI665560, SEQ ID NO: 54, pzb00414, umc2141, SEQ ID NO: 55, SEQ ID NO: 2, AY110435, e1fa5, SEQ ID NO: 5, umc1379, bn115.37a, SEQ ID NO: 56, pza02478, IDP3886, c139957_1, mmc0241, dup400(pac), jpsb107b, chs562, gpm709b, SEQ ID NO: 6, umc2321, bnlg1702, SEQ ID NO: 9, csu158b(eno), and gpm426b; wherein said allele confers enhanced resistance to anthracnose stalk rot compared to a plant lacking said allele. In some embodiments, step (b) of selecting comprises marker-assisted selection. In other embodiments, the progeny plant is an F2-F6 progeny plant. In further embodiments, producing the progeny plant comprises backcrossing. In yet further embodiments, backcrossing comprises from 2-7 generations of backcrosses. In some embodiments, backcrossing comprises marker-assisted selection in at least two generations. In other embodiments, the first corn plant is an inbred or a hybrid. In further embodiments, the second corn plant is an agronomically elite corn plant. In yet further embodiments, the agronomically elite corn plant is an inbred or a hybrid. In further embodiments, the invention provides a corn plant produced by the methods provided herein, or a plant part or seed of said corn plant.

In some aspects, corn plants or methods disclosed herein are used in combination with one or more pesticides including, but not limited to, herbicides, fungicides, insecticides, microbiocides, nematicides, insect repellents, bactericides, and other substances used to control pests. In other aspects, the corn plants or methods disclosed herein are used in combination with one or more triazoles, strobilurins, acylamino acids, pyrimidines, pyridines, aryl phenyl ketones, amides, benzanilides, imidazoles, dinitrophenols, morpholines, phenylsulfamides and organophosphorus cpds, derivatives thereof and combinations thereof which may be applied as seed, foliar, drench or drip treatments.

DESCRIPTION OF THE FIGURES

FIG. 1 shows first round fine-mapping of ASR-6.01 from CV820914/CV391950 as also shown in Table 10. Bulk "f" shared at least one same allele as the resistant inbred line (CV391950) at the SNP positions represented by SEQ ID NO: 51, SEQ ID NO: 52 and SEQ ID NO: 53 (highlighted by white cells). Bulk "f" shared the same alleles as the susceptible inbred line (CV820914) at the SNP positions represented by SEQ ID NO: 8, SEQ ID NO: 54, SEQ ID NO: 55, SEQ ID NO: 5 and SEQ ID NO: 56 (highlighted by grey cells). Similar experiments were also conducted on BC1F2 kernels derived from CV295879/CV391950. Bulk "f", "g", "i", "j", "p" and "o" displayed significantly reduced ASR severity (highlighted by black box, p-value<=0.05) compared with the bulk "b". Among these resistant bulks, the same common SNP (SEQ ID NO: 53, highlighted by black oval) was identified as the peak marker.

FIG. 2 shows first round fine-mapping of ASR-6.01 from CV295879/CV391950 as also shown in Table 11.

FIG. 3 shows second round fine-mapping of ASR-6.01 from CV005260/CV391950 as also shown in Table 14. For example, bulk "a" shared the same alleles as the resistant inbred line, CV391950, at the candidate QTL region (highlighted by white cells); bulk "b" shared the same alleles as the susceptible inbred line, CV005260, at the candidate QTL region (highlighted by grey cells).

DETAILED DESCRIPTION OF THE INVENTION

Anthracnose stalk rot (ASR) is caused by the fungal pathogen *Colletotrichum graminicola*, and results in severe yield loss in crop plants. Efforts to identify or produce plant lines resistant to ASR have been hindered by a limited understanding of the genetic loci controlling ASR resistance and a lack of available markers for detecting and tracking ASR resistance in plants. Yield loss due to ASR therefore remains a significant problem.

The present invention identifies previously-unknown genetic loci which confer ASR resistance and provides novel molecular markers linked to ASR resistance in plants. The invention further provides methods for introgression of genetic loci conferring ASR resistance into plant varieties previously lacking such loci, thereby providing plants with a new or improved disease resistance. The genetic loci, markers, and methods provided by the invention therefore represent a significant advance in the art, enabling production of new varieties exhibiting ASR resistance.

In some embodiments, the invention therefore provides quantitative trait loci (QTL) that demonstrate significant co-segregation with ASR resistance. The QTL of the invention can be tracked during plant breeding or introgressed into a desired genetic background in order to provide novel plants exhibiting ASR resistance and one or more other beneficial traits. In particular embodiments, the invention identifies for the first time a QTL on chromosome 6 of the corn genome, designated ASR-6.01, which is associated with ASR resistance.

In other embodiments, the invention provides molecular markers linked to the QTL of the invention and methods of using the markers for detection of and selection for ASR resistance. Embodiments of the invention therefore include specific markers, chromosome intervals comprising the markers, and methods of detecting markers genetically linked to ASR-6.01 to identify disease resistant plant lines. For example, the invention provides a chromosome interval associated with ASR resistance which is flanked by the markers IDP7601 and gpm426b, and which comprises markers having SEQ ID NOs: 1-10, 51-56, 81-83, and 96-106, or any of the markers listed in Table 17, and any other markers genetically linked thereto. Also provided herein are markers that are useful for detecting the presence or absence of disease resistance alleles within the QTL of the invention that can be used in marker assisted selection (MAS) breeding programs to produce plants with improved resistance to ASR infection.

The invention further provides methods of using the markers identified herein to introgress loci associated with ASR resistance into plants. Thus, one skilled in the art can use the invention to create novel maize plants with ASR resistance by crossing a donor line comprising a QTL associated with ASR resistance into any desired recipient line, with or without MAS. Resulting progeny can be selected to be genetically similar to the recipient line except for the ASR resistance QTL.

Quantitative Trait Loci The term "chromosome interval" designates a contiguous linear span of genomic DNA that resides on a single chromosome. A chromosome interval may comprise a QTL linked with a genetic trait and the QTL may comprise a single gene or multiple genes associated with the genetic trait. The boundaries of a chromosome interval comprising a QTL are drawn such that a marker that lies within the chromosome interval can be used as a marker for the genetic trait, as well as markers genetically linked thereto. Each interval comprising a QTL comprises at least one gene conferring a given trait, however knowledge of how many genes are in a particular interval is not necessary to make or practice the invention, as such an interval will segregate at meiosis as a linkage block. In accordance with the invention, a chromosomal interval comprising a QTL may therefore be readily introgressed and tracked in a given genetic background using the methods and compositions provided herein.

Identification of chromosomal intervals and QTL is therefore beneficial for detecting and tracking a genetic trait, such as ASR resistance, in plant populations. In some embodiments, this is accomplished by identification of markers linked to a particular QTL. The principles of QTL analysis and statistical methods for calculating linkage between markers and useful QTL include penalized regression analysis, ridge regression, single point marker analysis, complex pedigree analysis, Bayesian MCMC, identity-by-descent analysis, interval mapping, composite interval mapping (CIM), and Haseman-Elston regression. QTL analyses may be performed with the help of a computer and specialized software available from a variety of public and commercial sources known to those of skill in the art.

In some embodiments, the invention provides a chromosomal interval comprising a QTL associated with ASR resistance. The invention provides multiple markers associated with ASR resistance, for example the markers having the sequence of SEQ ID NOs: 1-10, 51-56, 81-83, or 96-106. The invention therefore provides a plant comprising a nucleic acid molecule selected from the group consisting of SEQ ID NOs: 1-10, 51-56, 81-83, 96-106, fragments thereof, or complements thereof. The present invention further provides a plant comprising alleles of the chromosome interval linked to ASR resistance or fragments and complements thereof as well as any plant comprising any combination of one or more disease resistance loci selected from the group consisting of SEQ ID NOs: 1-10, 51-56, 81-83 and 96-106. Plants provided by the invention may be homozygous or heterozygous for such alleles.

In one embodiment, the chromosome interval associated with ASR resistance contains SEQ ID NOs: 1-10, 51-56, 81-83 or 96-106, and is flanked by the markers IDP7601 and gpm426b. This chromosome interval encompasses markers that co-segregate with ASR resistance in the populations studied at a p-value≤0.05. An example of a subinterval associated with ASR resistance includes the interval flanked by umc2006 and chs562, which define a chromosome interval encompassing markers that co-segregate with ASR resistance in populations studied at a p-level≤0.05. An example of a subinterval associated with ASR resistance includes the interval flanked by SEQ ID NO: 52 and SEQ ID NO: 8, which define a chromosome interval encompassing markers that co-segregate with ASR resistance in populations studied at a p-level≤0.05. A further example of a subinterval associated with ASR resistance includes the interval flanked by SEQ ID NO: 53 and SEQ ID NO: 8, that define a chromosome interval encompassing markers that co-segregate with ASR resistance in the populations studied at a p-level≤0.05. Another example of a subinterval associated with ASR resistance includes the interval flanked by SEQ ID NO: 96 and SEQ ID NO: 106, that define a chromosome interval encompassing markers that co-segregate with ASR resistance in the populations studied at a p-level≤0.001.

Thus, one skilled in the art can use the invention to create novel maize plants with ASR resistance by associating disease resistance phenotypes with genotypes at previously unknown disease resistance loci in the maize genome. Disclosed herein are chromosome intervals that comprise alleles responsible for phenotypic differences between ASR resistant and ASR susceptible corn lines. The chromosome intervals of the invention are characterized in specific embodiments by genomic regions including and flanked by the markers IDP7601 and gpm426b, which comprise markers within or closely linked to (within 20 cM of) ASR-6.01. The invention also comprises other intervals whose borders fall between, and including, those of IDP7601 and gpm426b, or any interval closely linked to those intervals.

Examples of markers useful for this purpose comprise the SNP markers listed in Table 16, or any marker linked thereto, including a marker that maps within or is genetically linked to the chromosome intervals described herein, including the termini of the intervals. Such markers can be assayed simultaneously or sequentially in a single sample or population of samples.

Accordingly, the compositions and methods of the present invention can be utilized to guide MAS or breeding maize varieties with a desired complement (set) of allelic forms of chromosome intervals associated with superior agronomic performance (resistance, along with any other available markers for yield, disease resistance, etc.). Any of the disclosed marker alleles can be introduced into a corn line via introgression, by traditional breeding (or introduced via transformation, or both) to yield a corn plant with superior agronomic performance. The number of alleles associated with resistance that can be introduced or be present in a corn plant of the present invention ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this invention.

Similarly, by identifying plants lacking a desired marker locus, susceptible or less resistant plants can be identified, and eliminated from subsequent crosses. Similarly, these marker loci can be introgressed into any desired genomic background, germplasm, plant, line, variety, etc., as part of an overall MAS breeding program designed to enhance disease resistance. The invention also provides chromosome QTL intervals that find use in MAS to select plants that demonstrate disease resistance or improved tolerance. The QTL intervals can also be used to counter-select plants that are susceptible or have reduced resistance to disease.

The present invention also extends to a method of making a progeny corn plant and the resulting progeny corn plants. The method comprises, in an embodiment, crossing a first parent corn plant with a second corn plant and growing the female corn plant parent under plant growth conditions to yield corn plant progeny. Methods of crossing and growing corn plants are well within the ability of those of ordinary skill in the art. Such corn plant progeny can be assayed for alleles associated with ASR resistance as disclosed herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants is a corn plant of the present invention in that it comprises at least one of the allelic forms of the markers of the present invention, such that the progeny are capable of inheriting the allele.

Often, a method of the present invention may be applied to at least one related corn plant such as from progenitor or descendant line in the subject corn plants' pedigree such that inheritance of the desired resistance allele can be traced. The number of generations separating the corn plants being subjected to the methods of the present invention may be, in specific embodiments, from 1 to 20, commonly 1 to 5, and including 1, 2, or 3 generations of separation, and often a direct descendant or parent of the corn plant will be subject to the method (i.e., one generation of separation).

Thus, the invention permits one skilled in the art to detect the presence or absence of disease resistance genotypes in the genomes of corn plants as part of a MAS program. In one embodiment, a breeder ascertains the genotype at one or more markers for a disease resistant parent, which contains a disease resistance allele, and the genotype at one or more markers for a susceptible parent, which lacks the resistance allele. For example, the markers of the present invention can be used in MAS in crosses involving elite x exotic corn lines by subjecting the segregating progeny to MAS to maintain disease resistance alleles, or alleles associated with yield under disease conditions. A breeder can then reliably track the inheritance of the resistance alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the disease resistant parent can be reliably predicted to express the resistant phenotype and progeny that share genotypes with the disease susceptible parent can be reliably predicted to express the susceptible phenotype. Thus, the laborious, inefficient, and potentially inaccurate process of manually phenotyping the progeny for disease resistance is avoided.

By providing the positions in the maize genome of the intervals and the disease resistance associated markers within, this invention also allows one skilled in the art to identify and use other markers within the intervals disclosed herein or linked to the chromosome intervals disclosed herein. Having identified such regions, these markers can be readily identified from public linkage maps.

Closely linked markers flanking the locus of interest that have alleles in linkage disequilibrium with a resistance allele at that locus may be effectively used to select for progeny plants with enhanced resistance to disease conditions. Thus, the markers described herein, such as those listed in Table 16, as well as other markers genetically linked to the same chromosome interval, may be used to select for maize plants with enhanced resistance to ASR. Often, a set of these markers will be used, (e.g., 2 or more, 3 or more, 4 or more, 5 or more) in the flanking regions of the gene. Optionally, as described above, a marker flanking on either side or within the actual gene and/or locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice the invention is not limited and can be any marker that is genetically linked to the intervals described herein, which includes markers mapping within the intervals. One example includes any marker selected from SEQ ID NOs: 1-10, 51-56, 81-83, 96-106, or the markers listed in Table 17. Furthermore, since there are many different types of marker detection assays known in the art, it is not intended that the type of marker detection assay used to practice this invention be limited in any way.

Molecular Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., disease resistance). As used herein, a QTL marker has a minimum of one favorable allele, although it is possible that the marker might have two or more favorable alleles found in the population. Any favorable allele of that marker can be used advantageously for the identification and construction of disease resistant plant lines. Optionally, one, two, three or more favorable allele(s) of different markers are identified in, or introgressed into a plant, and can be selected for or against during MAS. Desirably, plants or germplasm are identified that have at least one such favorable allele that positively correlates with disease resistance or improved disease resistance. Alternatively, a marker allele that co-segregates with disease susceptibility also finds use with the invention, since that allele can be used to identify and counter select disease susceptible plants. Such an allele can be used for exclusionary purposes during breeding to identify alleles that negatively correlate with resistance, to eliminate susceptible plants or germplasm from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of any one particular marker) on the basis of polynucleotide length and/or sequence. A large number of corn molecular markers are known in the art, and are published or available from various sources, such as the MaizeGDB internet resource. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one resistance marker, or alternatively, favorable alleles from more than one resistance marker are introgressed into a desired germplasm. One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are routine and well known in the art, and furthermore, that the identification and use of such favorable alleles is well within the scope of this invention. Furthermore still, identification of favorable marker alleles in plant populations other than the populations used or described herein is well within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification-based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more properties of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

While the exemplary markers provided in the figures and tables herein are either SNP markers, any of the aforementioned marker types can be employed in the context of the invention to identify chromosome intervals encompassing genetic element that contribute to superior agronomic performance (e.g., disease resistance or improved disease tolerance).

Probes and Primers

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon. It is not intended that the nucleic acid probes of the invention be limited to any particular size.

In some embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

Linkage Analysis

"Linkage", or "genetic linkage," is used to describe the degree with which one marker locus is associated with another marker locus or some other locus (for example, a resistance locus). A marker locus may be located within a locus to which it is genetically linked. For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus may be genetically linked to a trait, and in some cases a marker locus genetically linked to a trait is located within the allele conferring the trait. A marker may also be causative for a trait or phenotype, for example a causative polymorphism. In a further example, a marker locus can be associated with resistance or improved tolerance to a plant pathogen when the marker locus is in linkage disequilibrium with the resistance trait. The degree of linkage of a molecular marker to a phenotypic trait (e.g., a QTL) is measured, e.g., as a statistical probability of co-segregation of that molecular marker with the phenotype.

As used herein, "closely linked" means that the marker or locus is within about 20 cM, for instance within about 10 cM, about 5 cM, about 1 cM, about 0.5 cM, or less than 0.5 cM of the identified locus associated with ASR resistance.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate.

Linkage analysis is used to determine which polymorphic marker allele demonstrates a statistical likelihood of co-segregation with the resistance phenotype (thus, a "resistance marker allele"). Following identification of a marker allele for co-segregation with the resistance phenotype, it is possible to use this marker for rapid, accurate screening of plant lines for the resistance allele without the need to grow the plants through their life cycle and await phenotypic evaluations, and furthermore, permits genetic selection for the particular resistance allele even when the molecular identity of the actual resistance QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through MAS, a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with the disease resistance phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

Marker Assisted Selection

"Introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that are resistant, exhibit improved resistance or are susceptible to ASR infection by identifying plants having a specified allele that is linked to ASR-6.01.

In general, MAS uses polymorphic markers that have been identified as having a significant likelihood of co-segregation with a resistance trait. Such markers are presumed to map near a gene or genes that give the plant its resistance phenotype, and are considered indicators for the desired trait, and are termed QTL markers. Plants are tested for the presence or absence of a desired allele in the QTL marker.

Identification of plants or germplasm that include a marker locus or marker loci linked to a resistance trait or traits provides a basis for performing MAS. Plants that comprise favorable markers or favorable alleles are selected for, while plants that comprise negative markers or alleles that are negatively correlated with resistance can be selected against. Desired markers and/or alleles can be introgressed into plants having a desired (e.g., elite or exotic) genetic background to produce an introgressed resistant plant or germplasm. In some aspects, it is contemplated that a plurality of resistance markers are sequentially or simultaneous selected and/or introgressed. The combinations of resistance markers that are selected for in a single plant is not limited, and can include any combination of markers disclosed herein or any marker linked to the markers disclosed herein, or any markers located within the QTL intervals defined herein.

In some embodiments, a disease resistant first corn plant or germplasm (the donor) can be crossed with a second corn plant or germplasm (the recipient, e.g., an elite or exotic corn, depending on characteristics that are desired in the progeny) to create an introgressed corn plant or germplasm as part of a breeding program designed to improve disease resistance of the recipient corn plant or germplasm. In some aspects, the recipient plant can also contain one or more disease resistant loci, which can be qualitative or quantitative trait loci. In another aspect, the recipient plant can contain a transgene.

In some embodiments, the recipient corn plant or germplasm will typically display reduced resistance to disease conditions as compared to the first corn plant or germplasm, while the introgressed corn plant or germplasm will display an increased resistance to disease conditions as compared to the second plant or germplasm. An introgressed corn plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one or multiple traits, e.g., multiple loci involved in resistance, or multiple loci each involved in resistance or tolerance to different diseases, the efficiency of MAS compared to phenotypic screening becomes even greater, because all of the loci can be evaluated in the lab together from a single sample of DNA.

Introgression of ASR Resistance Loci Using MAS

The introgression of one or more desired loci from a donor line into another is achieved via repeated backcrossing to a recurrent parent accompanied by selection to retain one or more ASR resistance loci from the donor parent. Markers associated with ASR resistance are assayed in progeny and those progeny with one or more ASR resistance markers are selected for advancement. In another aspect, one or more markers can be assayed in the progeny to select for plants with the genotype of the agronomically elite parent. This invention anticipates that trait introgression activities will require more than one generation, wherein progeny are crossed to the recurrent (agronomically elite) parent or selfed. Selections are made based on the presence of one or more ASR resistance markers and can also be made based on the recurrent parent genotype, wherein screening is performed on a genetic marker and/or phenotype basis. In another embodiment, markers of this invention can be used in conjunction with other markers, ideally at least one on each chromosome of the corn genome, to track the introgression of ASR resistance loci into elite germplasm. In another embodiment, QTLs associated with ASR resistance will be useful in conjunction with SNP molecular markers of the present invention to combine quantitative and qualitative ASR resistance in the same plant. It is within the scope of this invention to utilize the methods and compositions for trait integration of ASR resistance. It is contemplated by the inventors that the present invention will be useful for developing commercial varieties with ASR resistance and an agronomically elite phenotype.

In an aspect, this invention could be used on any plant. In another aspect, the plant is selected from the genus *Zea*. In another aspect, the plant is selected from the species *Zea mays*. In a further aspect, the plant is selected from the subspecies *Zea mays* L. ssp. *mays*. In an additional aspect, the plant is selected from the group *Zea mays* L. subsp. *mays* Indentata, otherwise known as dent corn. In another aspect, the plant is selected from the group *Zea mays* L. subsp. *mays* Indurata, otherwise known as flint corn. In an aspect, the plant is selected from the group *Zea mays* L. subsp. *mays* Saccharata, otherwise known as sweet corn. In another aspect, the plant is selected from the group *Zea mays* L. subsp. *mays* Amylacea, otherwise known as flour corn. In a further aspect, the plant is selected from the group *Zea mays* L. subsp. *mays* Everta, otherwise known as pop corn. *Zea* plants include hybrids, inbreds, partial inbreds, or members of defined or undefined populations.

In another aspect, a corn plant of the invention can show a comparative resistance compared to a non-resistant control corn plant. In this aspect, a control corn plant will preferably be genetically similar except for the disease resistance allele or alleles in question. Such plants can be grown under similar conditions with equivalent or near equivalent exposure to the pathogen.

Transgenic Plants

Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the present disclosure, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant.

Regulatory elements such as promoters, leaders, enhancers, introns, and transcription termination regions (or 3' UTRs) can play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron. In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-lsl) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Regulatory elements may be characterized by their gene expression pattern, e.g., positive and/or negative effects, such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the disclosure.

In specific embodiments, chimeric DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

Exemplary promoters for expression of a nucleic acid sequence include plant promoters such as the CaMV 35S promoter, or others such as CaMV 19S, nos, Adh, sucrose synthase, α-tubulin, actin, cab, PEPCase or those promoters associated with the R gene complex. Tissue-specific promoters such as leaf specific promoters, or tissue selective promoters (e.g., promoters that direct greater expression in leaf primordia than in other tissues), and tissue-specific enhancers are also contemplated to be useful, as are inducible promoters such as ABA- and turgor-inducible promoters. Any suitable promoters known in the art may be used to express defensin or defensin-like coding sequences in a plant. In an embodiment, the CaMV35S promoter may be used to express defensin or defensin-like coding sequences in a plant. In yet another embodiment, a disease or pathogen inducible promoter can be used to express defensin or defensin like proteins. Examples of disease or pathogen inducible promoters can be found in Kooshki et al. *Plant Science* 165 (2003) 213-219, Koschmann et al. *Plant Physiology* 160 (2012) 178-191, Rushton et al. *The Plant Cell,* 14 (2002) 749-762, and Kirsch et al. *The Plant Journal* (2001) 26 217-227.

The DNA sequence between the transcription initiation site and the start of the coding sequence, i.e., the untranslated leader sequence, can also influence gene expression. As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. One may thus wish to employ a particular leader sequence with a transformation construct of the present disclosure. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of defensin or defensin-like coding sequences.

It is envisioned that defensin or defensin-like coding sequences may be introduced under the control of novel promoters, enhancers, etc., or homologous or tissue-specific or tissue-selective, or pathogen or disease promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure.

Transformation constructs prepared in accordance with the present disclosure may further include a 3' end DNA sequence that acts as a signal to terminate transcription and allow for the polyadenylation of the mRNA produced by coding sequences operably linked to a promoter. As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR. In one embodiment, the native terminator of a defensin or defensin-like coding sequence may be used. Alternatively, a heterologous 3' end may enhance the expression of sense or antisense defensin or defensin-like coding sequences.

Sequences that are joined to the coding sequence of an expressed gene, which are removed post-translationally from the initial translation product and which facilitate the transport of the protein into or through intracellular or extracellular membranes, are termed transit or targeting peptide (usually into vacuoles, vesicles, plastids and other intracellular organelles) and signal peptide or sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein.

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the present disclosure.

Selectable marker transgenes may also be used with the present disclosure. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the present disclosure are known in the art and include, but are not limited to, transcribable DNA molecules encoding β-glucuronidase (GUS), green fluorescent protein (GFP), proteins that confer antibiotic resistance, and proteins that confer herbicide resistance Plant Cell Transformation Methods Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), and U.S. Patent Application Publication Nos. US 2004/0087030 A1 (cotton), and US 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising the recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance or pest resistance or enhanced water use efficiency, to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application using a selective agent such as a herbicide for use with a herbicide resistance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits, such as resistance to anthracnose stalk rot in maize.

Definitions

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in in Alberts et al., Molecular Biology of The Cell, $5^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes Icorn, Oxford University Press: New York, 2007. The nomenclature for DNA bases as set forth at 37 CFR § 1.822 is used.

"Adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

"Allele" refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self fertilization (selfing).

"Elite line" means any line that has resulted from breeding and selection for superior agronomic performance. Numerous elite lines are available and known to those of skill in the art of corn breeding. An "elite population" is an assortment of elite individuals or lines that can be used to represent the state of the art in terms of agronomically superior genotypes of a given crop species, such as corn. Similarly, an "elite germplasm" or elite strain of germplasm is an agronomically superior germplasm.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

"Linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The tern "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

"Locus" a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker Assisted Selection" (MAS) is a process by which phenotypes are selected based on marker genotypes.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Percent identity" or "% identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a resistance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different corn line) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant lines, or plant families under disease conditions, and furthermore, will also recognize the phenotypic gradations of "resistant."

"Resistance locus" means a locus that contributes resistance, tolerance, or susceptibility to anthracnose stalk rot.

"Resistance allele" means the nucleic acid sequence associated with resistance or tolerance to disease.

"Tolerance locus" means a locus associated with tolerance or resistance to disease. For instance, a tolerance locus according to the present invention may, in one embodiment, control tolerance or susceptibility for one or more races of *Colletotrichum graminicola*.

"Tolerance allele" means the nucleic acid sequence associated with tolerance or resistance to disease.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tolerance" or "improved tolerance" in a plant to disease conditions is an indication that the plant is less affected by disease conditions with respect to yield, survivability and/or other relevant agronomic measures, compared to a less resistant, more "susceptible" plant. Tolerance is a relative term, indicating that a "tolerant" plant survives and/or produces better yields in disease conditions compared to a different (less tolerant) plant (e.g., a different corn line strain) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance or susceptibility of different plants, plant lines or plant families under disease conditions, and furthermore, will also recognize the phenotypic gradations of "tolerant."

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "subcloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Yield" is the culmination of all agronomic traits as determined by the productivity per unit area of a particular plant product of commercial value. "Agronomic traits," include the underlying genetic elements of a given plant variety that contribute to yield over the course of growing season.

EXAMPLES

Example 1. Field Studies A, B and C

Biparental Mapping Populations

Parental lines were selected from resistant inbred lines: CV820914, CV094802 and CV594360, and susceptible inbred lines: CV391950, I294213 and I283669. CV391950 is described in U.S. Pat. Nos. 7,718,859; 1,294,213 is described in U.S. Pat. Nos. 7,166,779; and 1,283,669 is described in U.S. Pat. No. 7,414,181. Number of lines derived were 168 doubled-haploid from CV820914/CV391950, 180 BC1F3 inbred from CV094802/I294213*2 and 178 BC1F2 inbred from I283669*2/CV594360. 168 hybrid lines were also derived from the cross of (CV820914/CV391950) BC1F3 and testers that are modest-resistant or neutral to ASR (Table 1).

TABLE 1

Mapping populations

| Field Study | Mapping Population | Resistant Line | Susceptible Line | Population Type | Gender | Number of Lines |
|---|---|---|---|---|---|---|
| A | CV820914/CV391950 | CV820914 | CV391950 | DH | M | 168 |
| A | CV820914/CV391950 | CV820914 | CV391950 | (BC1F3XTester)F1 | M | 168 |
| B | CV094802/I294213*2 | CV094802 | I294213 | BC1F3 | F | 180 |
| C | I283669*2/CV594360 | CV594360 | I283669 | BC1F2 | M | 178 |

Inoculation and Rating Scale of Phenotypes

Corn plants grown in a field were inoculated 14 days after the mid-silk stage, i.e. the point when 50% of the plants within a given row had reached the R1 (silking) growth stage, by injecting 5×105 *Colletotrichum graminicola* spores suspended in 1 mL of distilled water. Thirty days after inoculation, the severity of anthracnose stalk rot in plants was visually assessed by splitting each stalk longitudinally to expose the pith. Each pith was examined to determine 1) the total number of internodes that displayed visual legions characteristic of the disease, and 2) the total number of internodes wherein visual legions had infected >75% of the tissue within the internode, as summarized in Table 2. These two numbers were then summed into a disease score phenotype for each plant, with scores of 10 converted to 9 to fit a scale ranging from 1 (highly resistant) to 9 (highly susceptible). Twelve to fourteen plants were ranged per row and the space between each row was 0.80 m in field. The individual plant scores of each row were then averaged and the average was reported as a final score for the row. Two populations (CV820914/CV391950 and CV094802/I294213*2) were measured in two field replicates and one population (I283669*2/CV594360) was measured in three field replicates for ASR resistance at different research sites using methods described in the art and the rating scale in Table 2.

Phenotype Analysis

After statistical procedures for phenotype quality control, a mixed model was run to estimate the variance components and to compute the heritability for ASR resistance. The heritability was 0.40 for inbred per se and 0.60 for hybrid for the population CV820914/CV391950, 0.46 for inbred per se for the population CV094802/I294213*2, and 0.30 for inbred per se for the population I283669*2/CV594360.

TABLE 2

Rating Scale of relative ASR infection resistance phenotypes

| No. Internodes Infected | No. Internodes >75% Infected | Score | Rating |
|---|---|---|---|
| 1 | 0 | 1 | Highly resistant |
| 1 | 1 | 2 | Highly resistant |
| 2 | 1 | 3 | Resistant |
| 2 | 2 | 4 | Resistant |
| 3 | 2 | 5 | Intermediate |
| 3 | 3 | 6 | Susceptible |
| 4 | 3 | 7 | Susceptible |
| 4 | 4 | 8 | Highly susceptible |
| 5 | 4 | 9 | Highly susceptible |
| 5 | 4 or 5 | 9 | Highly susceptible |

Primers and Probes Useful for Detecting ASR Resistance Genotypes

These plants were then genotyped using SNP markers that collectively spanned each chromosome in the maize genome. Loci that were monomorphic in the subject populations were eliminated from further analysis.

The primer sequences for amplifying exemplary SNP marker loci linked to ASR-6.01 QTL and the probes used to genotype the corresponding SNP sequences are provided in Table 3. One of skill in the art will recognize that sequences to either side of the given primers can be used in place of the given primers, so long as the primers can amplify a region that includes the allele to be detected. The precise probe to be used for detection can vary, e.g., any probe that can identify the region of a marker amplicon to be detected can be substituted for those probes exemplified herein. Also, configuration of the amplification primers and detection probes can, of course, vary. Thus, the invention is not limited to the primers, probes, or marker sequences specifically recited herein.

Illustrative ASR resistance marker DNA sequences SEQ ID NOs: 1 can be amplified using the primers described in Table 3 as SEQ ID NOs: 11 (forward primer) and 21 (reverse primer), and detected with probes as SEQ ID NOs: 31 (probe 1) and 41 (probe 2).

Marker-Trait Association Study

Marker-trait association studies were performed using both single-marker analysis (SMA) and CIM. For each marker, the thresholds of Likelihood ratio between full and null models for CIM were based on 1000 random permutation tests and the thresholds (p-value) for SMA were based on 10,000 random permutation tests (Churchill and Doerge 1994). The CIM analysis revealed a strong QTL associated with ASR resistance on chromosome 6. The QTL was confirmed in multiple genetic backgrounds and multi-year phenotypes for both inbred per se and hybrid populations. The QTL peaks from these three populations were located on chromosome 6 within 54 to 62 cM on the Monsanto's internal consensus genetic map as shown in Table 4. Combining the data from three mapping populations, the interval for this QTL was 48.8-67.9 cM. This QTL is designated as "ASR-6.01". The QTL effect for one copy of favorable allele was 0.75 rating score and 1.5 rating score for homozygotes on average. The phenotypic variance explained (R2) by this QTL was 24%.

TABLE 4

Summary of the CIM analysis from field studies A, B, and C.

| Field Study | Mapping Population | Population Type | #Mk | Resistant Parent | Chr | QTL Peak | Left | Right | P-val | Additive | QTL $R^2$ | Total $R^2$ |
|---|---|---|---|---|---|---|---|---|---|---|---|---|
| A | CV820914/CV391950 | Inbred | 146 | CV391950 | 6 | 53.9 | 48.8 | 65.1 | 0.01 | 0.75 | 0.24 | 0.48 |
| A | CV820914/CV391950 | Hybrid | 146 | CV391950 | 6 | 54.9 | 49.9 | 67.9 | 0.01 | 1.16 | 0.55 | 0.66 |
| B | CV094802/I294213*2 | Inbred | 194 | CV094802 | 6 | 55.7 | 49.7 | 57.5 | 0.01 | 0.77 | 0.11 | 0.35 |
| C | I283669*2/CV594360 | Inbred | 140 | CV594360 | 6 | 62.5 | 56.8 | 66.6 | 0.01 | 0.61 | 0.11 | 0.22 |

*P-value is based on 1,000 permutation tests

TABLE 3

Primers and probes used for detecting SNPs linked to ASR-6.01 in field studies

| | | SEQ ID NO. | | | |
|---|---|---|---|---|---|
| SEQ ID NO. | SNP Pos. | Fwd Primer | Rev Primer | Probe 1 | Probe 2 |
| 1 | 433 | 11 | 21 | 31 | 41 |
| 2 | 381 | 12 | 22 | 32 | 42 |
| 3 | 221 | 13 | 23 | 33 | 43 |
| 4 | 130 | 14 | 24 | 34 | 44 |
| 5 | 373 | 15 | 25 | 35 | 45 |
| 6 | 301 | 16 | 26 | 36 | 46 |
| 7 | 463 | 17 | 27 | 37 | 47 |
| 8 | 618 | 18 | 28 | 38 | 48 |
| 9 | 148 | 19 | 29 | 39 | 49 |
| 10 | 469 | 20 | 30 | 40 | 50 |

Each row provides field study ID, mapping population, population type, number of markers used, resistant parent, chromosome position, the peak of the Likelihood ratio corresponds to ASR resistance, QTL interval where left and right flanking positions are shown, additive effect, phenotypic variance of individual QTL $R^2$ and total $R^2$.

Table 5 lists the effect estimates on ASR resistance phenotype ratings associated with each marker (SEQ ID NO) measured by single marker association (SMA) analysis in field study A, B and C. Each row provides the SEQ ID NO of the marker, and genetic map loci are represented in cM, with position zero being the first (most distal) marker known at the beginning of the chromosome on the internal consensus genetic map, mapping population, Genetic source of favorable allele, favorable allele, unfavorable allele, F statistical value and the estimated effect that the marker polymorphism had on the ASR phenotype. The statistical significance (p-value) of the association between the marker and the ASR resistance rating in each case was p-value≤0.01 on 10,000 permutation tests.

TABLE 5

Statistical associations of markers associated with ASR-6.01 in field studies A, B and C.

| SEQ ID NO. | MON Map cM | Mapping Population | Genetic Source of Favorable Allele | Favorable allele | Unfavorable allele | Fstat | Permutation testing Probability | Single Allele Effect |
|---|---|---|---|---|---|---|---|---|
| 1 | 49.7 | I283669*2/CV594360 | CV594360 | A | T | 14.1 | 0.01 | 0.51 |
| 2 | 62.5 | I283669*2/CV594360 | CV594360 | T | C | 23.4 | 0.001 | 0.63 |

TABLE 5-continued

Statistical associations of markers associated with ASR-6.01 in field studies A, B and C.

| SEQ ID NO. | MON Map cM | Mapping Population | Genetic Source of Favorable Allele | Favorable allele | Unfavorable allele | Fstat | Permutation testing Probability | Single Allele Effect |
|---|---|---|---|---|---|---|---|---|
| 3 | 49.6 | CV820914/CV391950 | CV391950 | C | T | 19.4 | 0.001 | 0.54 |
| 4 | 53.9 | CV820914/CV391950 | CV391950 | A | G | 45.3 | 0.001 | 0.77 |
| 5 | 63.1 | CV820914/CV391950 | CV391950 | T | C | 23.6 | 0.001 | 0.59 |
| 6 | 68.3 | CV820914/CV391950 | CV391950 | G | A | 21.2 | 0.001 | 0.56 |
| 7 | 49.7 | CV094802/I294213*2 | CV094802 | T | C | 17.2 | 0.005 | 0.76 |
| 8 | 58.6 | CV094802/I294213*2 | CV094802 | C | G | 17.6 | 0.005 | 0.78 |
| 9 | 69 | CV094802/I294213*2 | CV094802 | G | A | 19.4 | 0.001 | 0.81 |

*P-value is based on 10,000 permutation tests

For example, SEQ ID NO: 3 was associated with a 0.54 change in ASR resistance rating by one copy of the favorable allele. SEQ ID NO: 5 was associated with a 0.59 change in ASR resistance rating by one copy of the favorable allele. ASR resistance ratings were generated using the methods described in Example 1.

Example 2. Field Study D

180 BC1F4 plants were derived from BC1F3 CV094802/ I294213*2 as shown in Table 6. Corn plants were inoculated as described in Example 1 and then measured for ASR resistance at research site using methods described in the art and the rating scale in Table 2. These plants were genotyped using SNP markers that collectively spanned each chromosome in the maize genome. To note, the SNP markers used in this field study overlapped yet varied from the SNP markers used in the prior field studies.

TABLE 6

Mapping populations of field study D

| Field Study | Mapping Population | Resistant Parent | Susceptible parent | Population Type | Gender | Number of Lines |
|---|---|---|---|---|---|---|
| D | CV094802/I294213*2 | CV094802 | I294213 | BC1F4 | F | 180 |

Marker-Trait Association Study

Marker-trait association studies were performed using both SMA and CIM. For each marker, the thresholds of Likelihood ratio between full and null models for CIM were based on 1000 random permutation tests and the thresholds (p-value) for SMA were based on 10,000 random permutation tests (Churchill and Doerge 1994). The CIM analysis from field study D confirmed the QTL region associated with ASR resistance in Example 1. The QTL peak was mapped to 58.9 cM on chromosome 6 on the internally-derived genetic map as shown in Table 7. The QTL interval was 52.5-66.3cM. The phenotypic variance explained ($R^2$) by this QTL was 15%.

TABLE 7

Summary of the CIM analysis from field study D

| Field Study | Population Type | #Mk | Resistant Parent | Chr | QTL Peak | Left | Right | P-value | Additive | QTL $R^2$ | Total $R^2$ |
|---|---|---|---|---|---|---|---|---|---|---|---|
| D | Inbred | 178 | CV094802 | 6 | 58.9 | 52.5 | 66.3 | 0.01 | 0.54 | 0.15 | 0.38 |

*P-value is based on 1,000 permutation tests

Table 7 provides the population type, number of markers used, resistant parent, chromosome location, the peak of the Likelihood ratio corresponds to ASR resistance, QTL interval where left and right flanking positions are shown, additive effect, phenotypic variance of individual QTL or Total ($R^2$).

Table 8 lists the effect estimates on ASR resistance phenotype ratings of each marker (SEQ ID NO) linked to ASR-6.01 measured by single marker association (SMA) analysis from field study D. Each row provides the SEQ ID NO of the marker, genetic map loci are represented in cM, with position zero being the first (most distal) marker known at the beginning of the chromosome on the internal consensus genetic map, mapping population, genetic source of favorable allele, favorable allele, unfavorable allele, F statistical value and the estimated effect that the marker polymorphism had on the ASR phenotype. The statistical significance (p-value) of the association between the marker and the ASR resistance rating in each case was p-value≤0.01 on 10,000 permutation tests.

TABLE 8

Estimate effects of markers associated with ASR-6.01 from field study D.

| SEQ ID NO. | MON Map cM | Mapping Population | Genetic Source of Favorable Allele | Favorable allele | Unfavorable allele | Fstat | Permutation testing Probability | Single Allele Effect |
|---|---|---|---|---|---|---|---|---|
| 10 | 49.5 | CV094802/I294213*2 | CV094802 | A | G | 23.81 | 0.001 | 0.584 |
| 4 | 53.9 | | | A | G | 28.18 | 0.001 | 0.618 |
| 2 | 62.5 | | | T | C | 29.14 | 0.001 | 0.625 |

*P-value is based on 10,000 permutation tests

For example, SEQ ID NO: 10 was associated with a 0.584 change in ASR resistance rating by one copy of the favorable allele. SEQ ID NO: 4 was associated with a 0.618 change in ASR resistance rating by one copy of the favorable allele. ASR resistance ratings were generated using the methods described in Example 1.

Example 3. First Round of Fine-Mapping of ASR Resistance QTL on Chromosome 6

In order to obtain additional recombinants, CV820914/CV391950 derived F1 lines were selected, self-crossed, and harvested. The resulting segregating F2 kernels were chipped and genotyped with 8 SNP markers within 51-65 cM on Monsanto's internal consensus genetic map (Table 9).

TABLE 9

Primers and probes used for detecting SNPs linked to ASR-6.01 in first round fine-mapping

| | | SEQ ID NO. | | | |
|---|---|---|---|---|---|
| SEQ ID NO. | SNP Pos. | Fwd Primer | Rev Primer | Probe 1 | Probe 2 |
| 51 | 118 | 57 | 63 | 69 | 75 |
| 52 | 74 | 58 | 64 | 70 | 76 |
| 53 | 89 | 59 | 65 | 71 | 77 |
| 8 | 618 | 18 | 28 | 38 | 48 |
| 54 | 101 | 60 | 66 | 72 | 78 |
| 55 | 291 | 61 | 67 | 73 | 79 |
| 5 | 373 | 15 | 25 | 35 | 45 |
| 56 | 100 | 62 | 68 | 74 | 80 |

Kernels were bulked based on their haplotypes within this QTL region. These bulks (10-20 plants) were then planted and subsequently screened for ASR resistance via progeny test in the greenhouse. In Table 10, grey cells indicated that the bulk carried the same alleles as the susceptible inbred line at the specific SNP position. White cells indicated that the bulk carried at least one copy of the same allele as the resistant inbred line at the specific SNP position. Lines which were homozygous or heterozygous for the resistant allele were grouped together in this analysis. Bulk "b" shared the same candidate QTL region as the susceptible inbred line, CV820914. The individual plant scores of each bulk were averaged. The average was reported as a final score for the bulk and then compared with that of bulk "b". Bulk "f", "g", "h", "i", "j", "p" and "o" displayed significantly reduced ASR severity (highlighted by black box, p-value<0.05). Based on the common SNP (highlighted by black oval) of these bulks, SEQ ID NO: 53 was identified as the peak marker. The two closest markers flanking SEQ ID NO: 53 are SEQ ID NO: 52 and SEQ ID NO: 8.

For example, bulk "f" shared at least one same allele as the resistant inbred line (CV391950) at the SNP positions represented by SEQ ID NO: 51, SEQ ID NO: 52 and SEQ ID NO: 53 (highlighted by white cells). Bulk "f" shared the same alleles as the susceptible inbred line (CV820914) at the SNP positions represented by SEQ ID NO: 8, SEQ ID NO: 54, SEQ ID NO: 55, SEQ ID NO: 5 and SEQ ID NO: 56 (highlighted by grey cells).

Similar experiments were also conducted on BC1F2 kernels derived from CV295879/CV391950. Bulk "f", "g", "i", "j", "p" and "o" displayed significantly reduced ASR severity (highlighted by black box, p-value<=0.05) compared with the bulk "b". Among these resistant bulks, the same common SNP (SEQ ID NO: 53, highlighted by black oval) was identified as the peak marker, as shown in Table 11.

The QTL region associated with ASR resistance was fine-mapped to 53.9-58.6 cM on chromosome 6 based on the internally-derived genetic map (Table 12).

TABLE 12

Summary of first round fine-mapping results

| SEQ ID NO. | MON Map cM | Marker Profile |
|---|---|---|
| 52 | 53.9 | Left flanking marker |
| 53 | 56.8 | QTL peak |
| 8 | 58.6 | Right flanking marker |

Example 4. Second Round Fine-Mapping of ASR Resistance QTL on Chromosome 6

In order to further fine-map the QTL region, CV005260/CV391950 derived F2 lines were selected, self-crossed, and harvested. CV005260 was the susceptible inbred line and CV391950 was the resistant inbred line. The resulting segregating F3 kernels were chipped and genotyped with 6 SNP markers within 54-59 cM on the internally-derived genetic map (Table 13). Primer and probe synthesis is within the skill of the art once the SNP position in the corn genome is provided. One of skill in the art will also immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Also, configuration of the amplification primers and detection probes can, of course, vary. Thus, the invention is not limited to the primers, probes, or marker sequences specifically recited herein.

TABLE 13

Primers and probes used for detecting SNPs linked to ASR-6.01 in second round fine-mapping from CV005260/CV391950

| | | SEQ ID NO. | | | |
|---|---|---|---|---|---|
| SEQ ID NO. | SNP Pos. | Fwd Primer | Rev Primer | Probe 1 | Probe 2 |
| 4 | 130 | 14 | 24 | 34 | 44 |
| 81 | 101 | 84 | 87 | 90 | 93 |
| 82 | 101 | 85 | 88 | 91 | 94 |
| 53 | 89 | 59 | 65 | 71 | 77 |
| 83 | 101 | 86 | 89 | 92 | 95 |
| 8 | 618 | 18 | 28 | 38 | 48 |

Kernels were bulked based on their haplotypes within this QTL region. These bulks (9-19 plants/bulk) were then planted and subsequently screened for ASR resistance via progeny test in the greenhouse. In Table 14, grey cells indicated that the bulk shared the same alleles as the susceptible inbred line at the specific SNP positions. White cells indicated that the bulk shared the same alleles as the resistant inbred line at the specific SNP positions. The individual plant scores of each bulk were averaged and the average was reported as a final score for the bulk. Bulk "i", "j", "k", "l" and "m" displayed significantly reduced ASR severity with mean values less than 2 (highlighted by black box). Based on the common SNP (highlighted by black oval) of these bulks, SEQ ID NO: 83 was identified as the peak marker.

For example, bulk "a" shared the same alleles as the resistant inbred line, CV391950, at the candidate QTL region (highlighted by white cells); bulk "b" shared the same alleles as the susceptible inbred line, CV005260, at the candidate QTL region (highlighted by grey cells).

The two closest markers flanking SEQ ID NO: 83 are SEQ ID NO: 53 and SEQ ID NO: 8. The QTL region associated with ASR resistance was further fine-mapped to 56.8-58.6 cM on chromosome 6 based on the internally-derived genetic map (Table 15).

TABLE 15

Summary of second round fine-mapping results

| SEQ ID NO. | MON Map cM | Marker Profile |
|---|---|---|
| 53 | 56.8 | Left flanking marker |
| 83 | 57.1 | QTL peak |
| 8 | 58.6 | Right flanking marker |

Example 5. Further Fine-Mapping Using Genotype-by-Sequencing (GBS) Method

SNP markers were specifically designed for CV005260/CV391950-derived plants via genotype-by-sequencing method within ASR-6.01 interval. One hundred and twenty-seven BC1F2 inbred plants were genotyped and measured for ASR resistance. SMA analysis identified the top 11 SNP markers associated with ASR resistance. Each row in Table 16 provides the SEQ ID NO of the marker, genetic map positions of the marker, SNP position, favorable allele, unfavorable allele, marker effect, p-value and phenotypic variance ($R^2$) of the marker. Genetic map loci are represented in cM, with position zero being the first (most distal) marker known at the beginning of the chromosome on Monsanto's internal consensus genetic map.

TABLE 16

Further Fine-Mapping of ASR-6.01 via GBS Method

| SEQ ID NO. | MON Map cM | SNP position | Favorable allele | Unfavorable allele | Marker Effect | p-value | $R^2$ |
|---|---|---|---|---|---|---|---|
| 96 | 57.1 | 101 | C | T | 1 | 0.0001 | 0.12 |
| 97 | 58 | 151 | T | C | 0.94 | 0.0007 | 0.09 |
| 98 | 58 | 151 | T | C | 0.97 | 0.0002 | 0.11 |
| 99 | 58 | 151 | T | G | 0.98 | 0.0001 | 0.11 |
| 100 | 58 | 151 | A | G | 0.98 | 0.0001 | 0.11 |
| 101 | 58 | 151 | T | G | 0.98 | 0.0001 | 0.11 |
| 102 | 58 | 151 | C | A | 0.98 | 0.0001 | 0.11 |
| 103 | 58 | 151 | C | T | 0.97 | 0.0002 | 0.11 |
| 104 | 58.2 | 151 | A | G | 1.93 | 0.0003 | 0.1 |
| 105 | 58.2 | 151 | T | A | 0.75 | 0.0006 | 0.09 |
| 106 | 58.6 | 151 | A | G | 0.71 | 0.0002 | 0.1 |

Chromosome intervals according to the invention and comprising markers closely linked to the ASR-6.01 QTL are disclosed in Table 17. Genetic map loci are represented in cM, with position zero being the first (most distal) marker known at the beginning of the chromosome on both an internal consensus genetic map (MON) and the Neighbors 2008 maize genomic map (IBM2008), which is freely available to the public from the Maize GDB website and commonly used by those skilled in the art. Also disclosed in Table 17 are the physical locations of loci as they are reported on the B73 RefGen_v2 sequence public assembly by the Arizona Genomics Institute, available on the internet.

TABLE 17

Genetic and physical map positions of markers and chromosome intervals associated with ASR-6.01.

|  | Relative Genetic Map Position† | | Physical Map Position†† | | |
|---|---|---|---|---|---|
|  | MON | IBM2008 | | | |
| Marker/Locus | Map cM | Map IcM | Contig | Chr Start | Chr End |
| IDP7601 | 38.2 | 200.7 | AC204522.4 | 107366978 | 107368801 |
| IDP62 | 38.9 | 206.2 | AC208541.3 | 107736319 | 107737212 |
| l11 | 43.1 | 216 | — | — | — |
| IDP8090 | 44.6 | 219.5 | AC201909.4 | 109532609 | 109539045 |
| umc2006 | 48.7 | 228.9 | — | — | — |
| IDP8231 | 49.1 | 229.9 | AC206946.2 | 113039145 | 113042824 |
| umc248b | 49.1 | 230 | — | — | — |
| SEQ ID NO: 10 | 49.5 | 231.1 | — | — | — |
| pco136292 | 49.6 | 231.3 | — | — | — |
| SEQ ID NO: 3 | 49.6 | 231.3 | — | — | — |
| IDP6025 | 49.7 | 231.5 | AC212465.3 | 115308486 | 115310063 |
| IDP6010 | 49.7 | 231.5 | AC209367.3 | 116123817 | 116124980 |
| SEQ ID NO: 1 | 49.7 | 231.6 | — | — | — |
| SEQ ID NO: 7 | 49.7 | 231.6 | — | — | — |
| agrr118a | 50.1 | 232.6 | — | — | — |
| umc180(pep) | 50.2 | 232.9 | — | — | — |
| SEQ ID NO: 51 | 50.7 | 234.3 | — | — | — |
| gpm74 | 51.1 | 235.3 | — | — | — |
| TIDP3136 | 52.5 | 239.1 | AC209629.2 | 118788679 | 118790325 |
| AY107053 | 53.7 | 242.3 | — | — | — |
| SEQ ID NO: 4 | 53.9 | 242.7 | — | — | — |
| SEQ ID NO: 52 | 53.9 | 242.7 | — | — | — |
| IDP1699 | 54.1 | 243.3 | AC197533.3 | 120878064 | 120883418 |
| pdi7 | 54.9 | 245.3 | — | — | — |
| gpm869 | 55.3 | 246.2 | — | — | — |
| SEQ ID NO: 81 | 55.9 | 247.6 | — | — | — |
| ufg11 | 56.1 | 248.1 | — | — | — |
| SEQ ID NO: 82 | 56.3 | 251.3 | — | — | — |
| umc1250 | 56.6 | 254.5 | AC194965.4 | 127445565 | 127446395 |
| SEQ ID NO: 53 | 56.8 | 255.2 | — | — | — |
| TIDP3356 | 57 | 255.9 | AC203836.3 | 128061342 | 128063001 |
| SEQ ID NO: 83 | 57.1 | 256.3 | — | — | — |
| SEQ ID NO: 96 | 57.1 | 256.3 | — | — | — |
| csu382a(cld) | 57.3 | 257.1 | — | — | — |
| IDP2409 | 57.8 | 258.9 | AC189055.3 | 129901107 | 129902196 |
| SEQ ID NO: 97 | 58 | 259.6 | — | — | — |
| SEQ ID NO: 98 | 58 | 259.6 | — | — | — |
| SEQ ID NO: 99 | 58 | 259.6 | — | — | — |
| SEQ ID NO: 100 | 58 | 259.6 | — | — | — |
| SEQ ID NO: 101 | 58 | 259.6 | — | — | — |
| SEQ ID NO: 102 | 58 | 259.6 | — | — | — |
| SEQ ID NO: 103 | 58 | 259.6 | — | — | — |
| SEQ ID NO: 104 | 58.2 | 260.4 | — | — | — |
| SEQ ID NO: 105 | 58.2 | 260.4 | — | — | — |
| SEQ ID NO: 106 | 58.6 | 262.3 | — | — | — |
| PCO146525 | 58.6 | 262.3 | — | — | — |
| SEQ ID NO: 8 | 58.6 | 262.3 | — | — | — |
| csu225 | 58.7 | 262.8 | — | — | — |
| bnl3.03 | 58.9 | 264 | — | — | — |
| AI665560 | 61.1 | 273.2 | AC195903.3 | 132064031 | 132064497 |
| SEQ ID NO: 54 | 61.5 | 274.4 | — | — | — |
| pzb00414 | 61.7 | 275.2 | — | — | — |
| umc2141 | 62.5 | 295.4 | AC204295.3 | 134846202 | 134846710 |
| SEQ ID NO: 55 | 62.5 | 295.4 | — | — | — |
| SEQ ID NO: 2 | 62.5 | 295.4 | — | — | — |
| AY110435 | 62.8 | 296.3 | AC200260.3 | 137078584 | 137079677 |
| elfa5 | 63.1 | 297.1 | — | — | — |
| SEQ ID NO: 5 | 63.1 | 297.1 | — | — | — |
| umc1379 | 63.1 | 297.1 | AC214298.3 | 138536487 | 138537038 |
| bnl15.37a | 64.2 | 303 | — | — | — |
| SEQ ID NO: 56 | 64.3 | 303.4 | — | — | — |
| pza02478 | 64.3 | 303.5 | — | — | — |
| IDP3886 | 65 | 306 | AC205030.3 | 141412746 | 141415456 |
| cl39957_1 | 65.6 | 308 | — | — | — |
| mmc0241 | 66.2 | 312.8 | — | — | — |
| dup400(pac) | 66.4 | 313.4 | — | — | — |
| jpsb107b | 66.6 | 314 | — | — | — |

TABLE 17-continued

Genetic and physical map positions of markers and
chromosome intervals associated with ASR-6.01.

| Marker/Locus | Relative Genetic Map Position† MON Map cM | IBM2008 Map lcM | Physical Map Position†† | | |
| --- | --- | --- | --- | --- | --- |
| | | | Contig | Chr Start | Chr End |
| chs562 | 67.9 | 317.5 | — | — | — |
| gpm709b | 68.3 | 318.6 | — | — | — |
| SEQ ID NO: 6 | 68.3 | 318.7 | — | — | — |
| umc2321 | 68.4 | 319 | AC208555.3 | 147911766 | 147912501 |
| bnlg1702 | 69 | 320.7 | — | — | — |
| SEQ ID NO: 9 | 69 | 320.7 | — | — | — |
| csu158b(eno) | 69.2 | 321.6 | — | — | — |
| gpm426b | 77.9 | 350.6 | — | — | — |

†cM = centiMorgans, lcM = map units of the IBM2 2008 Neighbors Genetic Map.
††Arizona Genomics Institute B73 RefGen_v2 sequence.
* Exact coordinates not known. Coordinates can be estimated based on nearest flanking loci with known coordinates.

In Table 17, "lcM" refers to the map units of the IBM2 2008 Neighbors Genetic Map, which was generated with an intermated recombinant inbred population (syn 4) that resulted in approximately a four-fold increase in the number of meiosies as compared to the typical recombination experiment that is used to generate centiMorgan (cM) distances (Lee et al., 2002, *Plant Mol Biol* 48:453 and the Maize Genetics and Genomics Database). "cM" refers to the classical definition of a centimorgan wherein one cM is equal to a 1% chance that a trait at one genetic locus will be separated from a trait at another locus due to crossing over in a single generation (meaning the traits cosegregate 99% of the time during meiosis), and this definition is used herein to delineate map locations pertaining to this invention. Any markers within the identified region, including those disclosed herein or publicly known, could be used for detection of and selection for ASR resistance in accordance with the methods of the present invention.

Example 6. Annotated Genes within ASR-6.01

Table 18 lists annotated coding sequences within ASR-6.01 region. Each row provides gene ID, gene annotation, chromosome location, genetic position on Monsanto internal consensus map and physical position based on Arizona Genomics Institute B73 RefGen_v2 sequence which is publicly available. Transgenic maize resistant to anthracnose stalk rot can be created using these annotated genes as described in the specification.

TABLE 18

Annotated coding sequences within ASR-6.01 region.

| Gene ID | Annotation | Chr | MON Map cM † | Physical Map Position bp †† Start | End |
|---|---|---|---|---|---|
| 1 | Putative uncharacterized protein Sb10g013040 n = 2 Tax = Andropogoneae RepID = C5Z298_SORBI (4e-20) | 6 | 53.9 | 121384232 | 121384851 |
| 2 | Delta zein storage protein n = 6 Tax = Zea mays RepID = C7AIP8_MAIZE (3e-22) | 6 | 53.9 | 121390345 | 121391190 |
| 3 | S-layer domain protein n = 2 Tax = Cyanothece RepID = B7K1E8_CYAP8 (1e-19); GO_CC:GO:0009507, chloroplast# (3e-73) | 6 | 53.9 | 121497243 | 121506368 |
| 4 | ZCN11 n = 1 Tax = Zea mays RepID = A8WES3_MAIZE (5e-82); PBP: Phosphatidylethanolamine-binding protein (9.1e-43); GO_BP:GO:0030154, cell differentiation# (3e-34); GO_CC:GO:0005737, cytoplasm# (2e-46) | 6 | 53.9 | 121537244 | 121538748 |
| 5 | Protein binding protein n = 1 Tax = Zea mays RepID = B6SVM4_MAIZE (1e-103); GO_MF:GO:0046872, metal ion binding# (1e-103); GO_BP:GO:0007229, integrin-mediated signaling pathway# (7e-25); GO_CC:GO:0005622, intracellular# (7e-35) | 6 | 53.9 | 121553074 | 121554257 |
| 6 | ELMO domain-containing protein 2 n = 3 Tax = Zea mays RepID = B6T7G4_MAIZE (4e-23); GO_BP:GO:0006909, LMP#phagocytosis# (4e-23); GO_CC:GO:0005856, cytoskeleton# (4e-23) | 6 | 53.9 | 121544918 | 121556006 |
| 7 | SMC4 protein n = 3 Tax = Oryza sativa RepID = Q8L6H8_ORYSA (1e-104); GO_MF:GO:0005524, ATP binding# (1e-104); GO_BP:GO:0051276, chromosome organization# (1e-104); GO_CC:GO:0005694, chromosome# (1e-104) | 6 | 53.9 | 121556779 | 121559923 |
| 8 | Pollen-specific protein NTP303 n = 4 Tax = Zea mays RepID = B6U4I6_MAIZE (9e-60); GO_MF:GO:0016491, oxidoreductase activity# (9e-60); GO_BP:GO:0055114, oxidation reduction# (9e-60); GO_CC:GO:0005576, extracellular region# (5e-34) | 6 | 53.9 | 121566108 | 121567043 |
| 9 | AlphaSNBP(B)-like n = 3 Tax = Oryza sativa RepID = Q6S1K5_ORYSJ (1e-125); DFDF: DFDF motif (3.4e-07); FFD_TFG: FFD and TFG box motifs (1e-20) | 6 | 53.9 | 121688996 | 121698144 |
| 10 | Histone mRNA exonuclease 1 n = 2 Tax = Zea mays RepID = B6T5F9_MAIZE (0.0); Exonuc_X-T: Exonuclease (8e-05); GO_MF:GO:0004527, exonuclease activity# (0.0); GO_BP:GO:0031125, rRNA 3'-end processing# (2e-24); GO_CC:GO:0005622, intracellular# (2e-26) | 6 | 53.9 | 121757218 | 121777486 |
| 11 | Aluminum-activated malate transporter-like n = 2 Tax = Oryza sativa RepID = Q6EPG5_ORYSJ (7e-11); GO_BP:GO:0010044, response to aluminum ion# (7e-11) | 6 | 53.9 | 121766949 | 121767251 |
| 12 | Putative polyprotein n = 1 Tax = Zea mays RepID = Q8SA93_MAIZE (5e-45); Exo-endo_phos: Endonuclease/Exonuclease/phosphatase family (0.074); GO_MF:GO:0003964, RNA-directed DNA polymerase, group II intron encoded# (5e-45); GO_BP:GO:0015074, DNA integration# (5e-45); GO_CC:GO:0005634, nucleus# (5e-45) | 6 | 53.9 | 121770395 | 121775874 |
| 13 | DNA helicase homolog, putative n = 1 Tax = Musa acuminata RepID = Q1EPC6_MUSAC (1e-17); GO_MF:GO:0004386, helicase activity# (1e-17) | 6 | 53.9 | 121779361 | 121796764 |
| 14 | B-cell receptor-associated protein 31-like containing protein n = 2 Tax = Andropogoneae RepID = B6TG43_MAIZE (8e-20); GO_MF:GO:0004872, receptor activity# (8e-20); GO_BP:GO:0006886, intracellular protein transport# (2e-50); GO_CC:GO:0016021, integral to membrane# (2e-26) | 6 | 53.9 | 121926217 | 121928807 |
| 15 | Reticulon n = 3 Tax = Andropogoneae RepID = B6TG01_MAIZE (1e-135); Reticulon: Reticulon (6.5e-58); GO_MF:GO:0003676, nucleic acid binding# (2e-97); GO_BP:GO:0006313, transposition, DNA-mediated# (8e-89); GO_CC:GO:0005783, IDA#endoplasmic reticulum# (1e-135) | 6 | 53.9 | 121943435 | 121946102 |
| 16 | OSJNBa0029H02.21 protein n = 1 Tax = Oryza sativa RepID = Q7XT72_ORYSA (1e-09); Ribosomal_L23: Ribosomal protein L23 (0.0023); GO_MF:GO:0003735, structural constituent of ribosome# (2e-09); GO_BP:GO:0006412, translation# (2e-09); GO_CC:GO:0030529, ribonucleoprotein complex# (2e-09) | 6 | 53.9 | 122086378 | 122086631 |
| 17 | V-type proton ATPase 16 kDa proteolipid subunit c4 n = 52 Tax = Embryophyta RepID = VATL4_ARATH (2e-26); GO_MF:GO:0015078, hydrogen ion transmembrane transporter activity# (2e-26); GO_BP:GO:0015992, proton transport# (2e-26); GO_CC:GO:0033179, proton-transporting V-type ATPase, V0 domain# (2e-26) | 6 | 53.9 | 122086738 | 122090981 |
| 18 | Putative uncharacterized protein n = 2 Tax = Zea mays RepID = B6U525_MAIZE (5e-10) | 6 | 53.9 | 122093288 | 122093569 |
| 19 | Tesmin-like n = 2 Tax = Oryza sativa Japonica Group RepID = Q69WH4_ORYSJ (1e-145); CXC: Tesmin/TSO1-like CXC domain (5.9e-16); CXC: Tesmin/TSO1-like CXC domain (1.4e-21); GO_MF:GO:0005515, protein | 6 | 53.9 | 122095245 | 122102827 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 20 | binding# (1e-68); GO_BP:GO:0045449, regulation of transcription# (2e-74); GO_CC:GO:0031523, IDA#Myb complex# (8e-33) | | | | |
| | Fiber protein Fb34 n = 2 Tax = Andropogoneae RepID = B4FVT6_MAIZE (7e-36); DUF1218: Protein of unknown function (DUF1218) (2.2e-11) | 6 | 53.9 | 122116076 | 122116865 |
| 21 | Protein kinase family protein n = 2 Tax = Eumusa RepID = Q1EPA3_MUSAC (1e-146); Pkinase: Protein kinase domain (8.9e-36); Pkinase_Tyr: Protein tyrosine kinase (2.1e-36); APH: Phosphotransferase enzyme family (0.028); GO_MF:GO:0005524, ATP binding# (1e-179); GO_BP:GO:0006468, protein amino acid phosphorylation# (1e-179); GO_CC:GO:0016459, myosin complex# (1e-179) | 6 | 53.9 | 122247935 | 122249667 |
| 22 | Putative Potential phospholipid-transporting ATPase 8 n = 2 Tax = Oryza sativa RepID = Q67VX1_ORYSJ (0.0); E1-E2_ATPase: E1-E2 ATPase (9.6e-05); Hydrolase: haloacid dehalogenase-like hydrolase (0.0033); GO_MF:GO:0016820, hydrolase activity, acting on acid anhydrides, catalyzing transmembrane movement of substances# (0.0); GO_BP:GO:0016820, hydrolase activity, acting on acid anhydrides, catalyzing transmembrane movement of substances# (0.0); GO_CC:GO:0016021, integral to membrane# (0.0) | 6 | 53.9 | 122254921 | 122264424 |
| 23 | Retrotransposon protein, putative, unclassified n = 1 Tax = Oryza sativa Japonica Group RepID = Q2QRU0_ORYSJ (1e-10); RVT_2: Reverse transcriptase (RNA-dependent DNA pol (0.0023); GO_MF:GO:0003676, nucleic acid binding# (2e-10); GO_BP:GO:0015074, DNA integration# (4e-10) | 6 | 53.9 | 122304131 | 122304529 |
| 24 | Retrotransposon protein, putative, unclassified n = 2 Tax = Oryza sativa Japonica Group RepID = Q10HG0_ORYSJ (3e-30); GO_MF:GO:0004523, ribonuclease H activity# (3e-30); GO_BP:GO:0006278, RNA-dependent DNA replication# (3e-30) | 6 | 53.9 | 122311854 | 122312338 |
| 25 | Pyrophosphate-fructose-6-phosphate1-phosphotransferase alpha subunit (Fragment) n = 2 Tax = Saccharum officinarum complex RepID = A1E380_SACSP (5e-24); GO_MF:GO:0003872, 6-phosphofructokinase activity# (1e-24); GO_BP:GO:0006096, glycolysis# (1e-24); GO_CC:GO:0005945, 6-phosphofructokinase complex# (1e-24) | 6 | 53.9 | 122322616 | 122325389 |
| 26 | Pho1-like protein n = 1 Tax = Populus trichocarpa RepID = B9HWP3_POPTR (0.0); SPX: SPX domain (2.2e-26); EXS: EXS family (2.3e-144); GO_MF:GO:0004872, receptor activity# (0.0); GO_BP:GO:0004872, receptor activity# (0.0); GO_CC:GO:0016021, integral to membrane# (0.0) | 6 | 53.9 | 122394825 | 122399345 |
| 27 | PpPPR_77 protein n = 1 Tax = Physcomitrella patens RepID = Q5W963_PHYPA (1e-106); PPR: PPR repeat (0.26); PPR: PPR repeat (0.94); PPR: PPR repeat (0.0071); PPR: PPR repeat (3.6e-05); PPR: PPR repeat (6.1e-09); PPR: PPR repeat (0.057); PPR: PPR repeat (0.7); GO_MF:GO:0005488, binding# (4e-94); GO_CC:GO:0009536, plastid# (8e-99) | 6 | 53.9 | 122404713 | 122406776 |
| 28 | Putative uncharacterized protein 9C20.7 n = 1 Tax = Zea mays RepID = Q5NKP3_MAIZE (1e-12) | 6 | 53.9 | 122421193 | 122421729 |
| 29 | DEAD-box ATP-dependent RNA helicase 14 n = 4 Tax = Oryza sativa RepID = RH14_ORYSJ (2e-49); DEAD: DEAD/DEAH box helicase (0.087); PPR: PPR repeat (0.0031); PPR: PPR repeat (9.6e-05); GO_BP:GO:0042254, ribosome biogenesis# (2e-49); GO_CC:GO:0005634, nucleus# (2e-49) | 6 | 53.9 | 122524854 | 122525657 |
| 30 | Putative uncharacterized protein n = 1 Tax = Zea mays RepID = B6SM34_MAIZE (2e-13) | 6 | 53.9 | 122555403 | 122555864 |
| 31 | Pentatricopeptide repeat-containing protein, putative n = 1 Tax = Ricinus communis RepID = B9SV96_RICCO (1e-173); PPR: PPR repeat (0.0007); PPR: PPR repeat (0.0031); PPR: PPR repeat (9.6e-05); PPR: PPR repeat (5e-11); PPR: PPR repeat (0.0066); PPR: PPR repeat (0.036); PPR: PPR repeat (7e-10); PPR: PPR repeat (0.18); PPR: PPR repeat (8.7e-08); GO_MF:GO:0030528, transcription regulator activity# (0.0); GO_BP:GO:0045449, regulation of transcription# (0.0); GO_CC:GO:0009536, plastid# (1e-173) | 6 | 53.9 | 122582468 | 122585135 |
| 32 | MADS-box transcription factor 31 n = 3 Tax = Andropogoneae RepID = B6TW19_MAIZE (6e-14); GO_MF:GO:0043565, sequence-specific DNA binding# (6e-14); GO_BP:GO:0045449, regulation of transcription# (6e-14); GO_CC:GO:0005634, nucleus# (6e-14) | 6 | 53.9 | 122587039 | 122588859 |
| 33 | Probable calcium-binding protein CML30 n = 3 Tax = Oryza sativa RepID = CML30_ORYSJ (1e-54); efhand: EF hand (0.0013); efhand: EF hand (0.0066); efhand: EF hand (1.4e-06); efhand: EF hand (4e-08); | 6 | 53.9 | 122664103 | 122665029 |

TABLE 18-continued

Annotated coding sequences within ASR-6.01 region.

| Gene ID | Annotation | Chr | MON Map cM† | Physical Map Position bp †† Start | End |
|---|---|---|---|---|---|
| 34 | GO_MF:GO:0005509, calcium ion storage activity# (1e−105); GO_BP:GO:0009409, IEP#response to cold# (5e−21); GO_CC:GO:0005737, cytoplasm# (5e−21) | 6 | 53.9 | 122727878 | 122731414 |
| 35 | Alkaline alpha galactosidase 2 n = 1 Tax = Zea mays RepID = Q57527_MAIZE (0.0); Raffinose_syn: Raffinose synthase or seed imbibition protein Sip1 (0); GO_MF:GO:0047274, galactinol-sucrose galactosyltransferase activity# (0.0); GO_BP:GO:0009409, IEP#response to cold# (0.0); GO_CC:GO:0009507, chloroplast# (0.0) | 6 | 53.9 | 122797640 | 122807850 |
| 36 | 26S protease regulatory subunit 6A homolog n = 12 Tax = Poaceae RepID = PRS6A_ORYSJ (2e−37); GO_MF:GO:0016765, transferase activity, transferring alkyl or aryl (other than methyl) groups# (2e−37); GO_BP:GO:0030163, protein catabolic process# (8e−36); GO_CC:GO:0005737, cytoplasm# (8e−36) 26S protease regulatory subunit 6A homolog n = 12 Tax = Poaceae RepID = PRS6A_ORYSJ (1e−135); AAA_2: ATPase family associated with various (0.0093); AAA: ATPase family associated with various cellular activities (AAA) (1.2e−89); AAA_3: ATPase family associated with various (0.011); AAA_5: ATPase family associated with various (0.00017); GO_MF:GO:0017111, nucleoside-triphosphatase activity# (1e−130); GO_BP:GO:0030163, protein catabolic process# (1e−130); GO_CC:GO:0005737, cytoplasm# (1e−130) | 6 | 53.9 | 122836036 | 122838395 |
| 37 | Putative uncharacterized protein n = 2 Tax = Zea mays RepID = B6TTZ4_MAIZE (0.0); Dev_Cell_Death: Development and cell death domain (1e−63); GO_MF:GO:0003677, DNA binding# (5e−33) | 6 | 53.9 | 122889105 | 122892158 |
| 38 | Longin-like n = 1 Tax = Medicago truncatula RepID = A4Q7K9_MEDTR (2e−77); Synaptobrevin: Synaptobrevin (1.1e−39); GO_MF:GO:0005515, protein binding# (7e−45); GO_BP:GO:0016192, vesicle-mediated transport# (1e−104); GO_CC:GO:0016021, integral to membrane# (1e−104) | 6 | 53.9 | 122950872 | 122954048 |
| 39 | Clathrin assembly protein AP180 short form-like n = 2 Tax = Oryza sativa RepID = Q69SJ3_ORYSJ (1e−169); ANTH: ANTH domain (5.7e−112); ENTH: ENTH domain (6.1e−05); GO_MF:GO:0030276, clathrin binding# (0.0); GO_BP:GO:0048268, IDA#clathrin coat assembly# (0.0); GO_CC:GO:0030118, clathrin coat# (0.0) | 6 | 53.95 | 122961662 | 122968145 |
| 40 | Receptor serine-threonine protein kinase, putative n = 1 Tax = Ricinus communis RepID = B9S1N3_RICCO (1e−138); Pkinase: Protein kinase domain (7.9e−31); Pkinase_Tyr: Protein tyrosine kinase (4.3e−31); GO_MF:GO:0005524, ATP binding# (0.0); GO_BP:GO:0006468, protein amino acid phosphorylation# (0.0) | 6 | 54 | 122994729 | 122996638 |
| 41 | Cytochrome b-c1 complex subunit 8 n = 1 Tax = Solanum tuberosum RepID = QCR8_SOLTU (2e−20); GO_MF:GO:0016491, oxidoreductase activity# (2e−16); GO_BP:GO:0022900, electron transport chain# (2e−20); GO_CC:GO:0070469, respiratory chain# (2e−20) | 6 | 54.1 | 123080089 | 123083460 |
| 42 | Putative iron/ascorbate-dependent oxidoreductase n = 1 Tax = Oryza sativa Japonica Group RepID = Q658E2_ORYSJ (7e−78); 2OG-FeII_Oxy: 2OG-Fe(II) oxygenase superfamily (1.1e−30); GO_MF:GO:0016491, oxidoreductase activity# (1e−80); GO_BP:GO:0055114, oxidation reduction# (1e−80) | 6 | 54.1 | 123156144 | 123157022 |
| 43 | OSJNBa0029H02.21 protein n = 1 Tax = Oryza sativa RepID = Q7XT72_ORYSA (6e−22); Ribosomal_L23eN: Ribosomal protein L23, N-terminal domain (2.4e−18); GO_MF:GO:0003735, structural constituent of ribosome# (7e−22); GO_BP:GO:0006412, translation# (7e−22); GO_CC:GO:0030529, ribonucleoprotein complex# (7e−22) | 6 | 54.1 | 123201331 | 123203345 |
| 44 | Putative uncharacterized protein Sb01g049710 n = 1 Tax = Sorghum bicolor RepID = C5X128_SORBI (1e−23) | 6 | 54.1 | 123335141 | 123335768 |
| 45 | Pyrophosphate-energized vacuolar membrane proton pump n = 12 Tax = Poaceae RepID = AVP_HORVU (0.0); H_PPase: Inorganic H+ pyrophosphatase (0); OPT: OPT oligopeptide transporter protein (0.084); BCCT: BCCT family transporter (0.062); GO_MF:GO:0016787, hydrolase activity# (0.0); GO_BP:GO:0015992, proton transport# (0.0); GO_CC:GO:0016021, integral to membrane# (0.0) | 6 | 54.1 | 123336536 | 123341421 |
| 46 | Heparanase-like protein 3 n = 3 Tax = Andropogoneae RepID = B6SXU7_MAIZE (0.0); Glyco_hydro_79n: Glycosyl hydrolase family 79, N-terminal domain (2.4e−88); GO_MF:GO:0016798, hydrolase activity, acting on glycosyl bonds# (0.0); GO_BP:GO:0055085, transmembrane transport# (2e−50); GO_CC:GO:0016020, membrane# (0.0) | 6 | 54.1 | 123344114 | 123346798 |
| 47 | Jp18 n = 1 Tax = Citrus trifoliata RepID = Q8H6R4_PONTR (3e−17) | 6 | 54.1 | 123370995 | 123372142 |
| 48 | Nodulin-like protein n = 2 Tax = Oryza sativa RepID = Q8H613_ORYSJ (0.0); Nodulin-like: Nodulin-like (2.8e−117); MFS_1: Major Facilitator Superfamily (0.049); GO_MF:GO:0016798, hydrolase activity, acting on | 6 | 54.1 | 123372572 | 123376208 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 49 | Putative villin n = 1 Tax = Oryza sativa Japonica Group RepID = Q65XP6_ORYSJ (0.0); Gelsolin: Gelsolin repeat (3.6e–11); Gelsolin: Gelsolin repeat (0.00013); Gelsolin: Gelsolin repeat (5.4e–05); Gelsolin: Gelsolin repeat (2e–05); Gelsolin: Gelsolin repeat (0.064); Gelsolin: Gelsolin repeat (0.13); GO_MF:GO:0003779, actin binding# (0.0); GO_BP:GO:0007010, cytoskeleton organization# (0.0); GO_CC:GO:0015629, actin cytoskeleton# (0.0) | 6 | 54.1 | 123383577 | 123388905 |
| 50 | Tryptophan aminotransferase n = 2 Tax = Zea mays RepID = B5AIU2_MAIZE (0.0); Allinase_C: Allinase, C-terminal domain (8.5e–198); Aminotran_1_2: Aminotransferase class I and II (0.00013); GO_MF:GO:0030170, pyridoxal phosphate binding# (0.0); GO_BP:GO:0080022, IMP#primary root development# (7e–91); GO_CC:GO:0005737, cytoplasm# (2e–89) | 6 | 54.2 | 123432761 | 123435867 |
| 51 | OSJNBa0053K19.25 protein n = 2 Tax = Oryza sativa RepID = Q7XPP8_ORYSJ (6e–26) | 6 | 54.8 | 123669647 | 123669987 |
| 52 | OSJNBa0053K19.25 protein n = 2 Tax = Oryza sativa RepID = Q7XPP8_ORYSJ (3e–46); DUF1682: Protein of unknown function (DUF1682) (0.0022); GO_CC:GO:0016021, integral to membrane# (2e–17) | 6 | 54.85 | 123660711 | 123671949 |
| 53 | OSJNBa0053K19.25 protein n = 2 Tax = Oryza sativa RepID = Q7XPP8_ORYSJ (8e–18); GO_CC:GO:0005739, mitochondrion# (2e–14) | 6 | 54.9 | 123671681 | 123672761 |
| 54 | 2,3-bisphosphoglycerate-independent phosphoglycerate mutase n = 6 Tax = Poaceae RepID = PMGI_MAIZE (3e–99); iPGM_N: BPG-independent PGAM N-terminus (iPGM) (9.4e–16); GO_MF:GO:0046872, metal ion binding# (3e–99); GO_BP:GO:0008152, metabolic process# (3e–99); GO_CC:GO:0005737, cytoplasm# (3e–99) | 6 | 54.9 | 123673484 | 123674700 |
| 55 | Cyclic nucleotide-gated ion channel 2 (Fragment) n = 1 Tax = Hordeum vulgare subsp. vulgare RepID = Q4VDM4_HORVD (3e–15); GO_MF:GO:0005216, ion channel activity## (5e–12); GO_BP:GO:0055085, transmembrane transport# (5e–12); GO_CC:GO:0016021, integral to membrane# (5e–12) | 6 | 54.9 | 123676263 | 123676490 |
| 56 | CENP-E like kinetochore protein n = 1 Tax = Zea mays RepID = B6SHI8_MAIZE (0.0); KIP1: KIP1-like protein (2.6e–38); DUF2051: Double stranded RNA binding protein ((0.079); Pox_A_type_inc: Viral A-type inclusion protein repeat (57); Pox_A_type_inc: Viral A-type inclusion protein repeat (77); Pox_A_type_inc: Viral A-type inclusion protein repeat (0.79); Pox_A_type_inc: Viral A-type inclusion protein repeat (12); Cenp-F_leu_zip: Leucine-rich repeats of kinetochore p (0.053); Pox_A_type_inc: Viral A-type inclusion protein repeat (27); GO_MF:GO:0016301, kinase activity# (1e–132); GO_BP:GO:0016301, kinase activity# (1e–132); GO_CC:GO:0005886, plasma membrane# (1e–21) | 6 | 54.9 | 123677322 | 123687963 |
| 57 | NHP2-like protein 1 n = 7 Tax = Andropogoneae RepID = B6TBE1_MAIZE (5e–24); GO_MF:GO:0005515, protein binding# (5e–19); GO_BP:GO:0042254, ribosome biogenesis# (5e–24); GO_CC:GO:0030529, ribonucleoprotein complex# (5e–24) | 6 | 54.9 | 123706476 | 123707839 |
| 58 | Integral membrane protein like n = 1 Tax = Zea mays RepID = B6SMU5_MAIZE (1e–139); UAA: UAA transporter family (4.5e–49); Nuc_sug_transp: Nucleotide-sugar transporter (0.022); DUF6: Integral membrane protein DUF6 (0.037); TPT: Triose-phosphate Transporter family (4.5e–49); GO_BP:GO:0009624, IEP#response to nematode# (5e–36); GO_CC:GO:0016021, integral to membrane# (1e–125) | 6 | 54.9 | 123729619 | 123734039 |
| 59 | Aminotransferase y4uB n = 2 Tax = Andropogoneae RepID = B6T579_MAIZE (9e–27); GO_MF:GO:0030170, pyridoxal phosphate binding## (9e–27); GO_BP:GO:0055114, oxidation reduction# (9e–12) | 6 | 54.9 | 123741189 | 123741689 |
| 60 | Aminotransferase y4uB n = 2 Tax = Andropogoneae RepID = B6T579_MAIZE (1e–62); GO_MF:GO:0030170, pyridoxal phosphate binding# (1e–62) | 6 | 54.9 | 123741701 | 123742472 |
| 61 | Putative uncharacterized protein Sb09g005000 n = 2 Tax = Andropogoneae RepID = C5Z118_SORBI (1e–111); GO_BP:GO:0006979, response to oxidative stress# (2e–78) | 6 | 54.9 | 123748498 | 123751787 |
| 62 | Transcription factor BIM2 n = 3 Tax = Andropogoneae RepID = B6SVP6_MAIZE (7e–11); GO_MF:GO:0030528, transcription regulator activity# (7e–11); GO_BP:GO:0045449, regulation of transcription# (7e–11); GO_CC:GO:0005634, nucleus# (7e–11) | 6 | 54.9 | 123753813 | 123761545 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 63 | AP2 domain-containing transcription factor n = 1 Tax = Populus trichocarpa RepID = B9GNL6_POPTR (4e–22); GO_MF:GO:0003700, transcription factor activity# (7e–23); GO_BP:GO:0045449, regulation of transcription# (7e–23); GO_CC:GO:0005634, nucleus# (7e–23) | 6 | 54.9 | 123763332 | 123764175 |
| 64 | Catalytic/hydrolase n = 2 Tax = Zea mays RepID = B6TIK5_MAIZE (1e–120); GO_MF:GO:0016787, hydrolase activity# (1e–120); GO_BP:GO:0008152, metabolic process# (1e–120) | 6 | 54.9 | 123766758 | 123770464 |
| 65 | Germin-like protein n = 4 Tax = Andropogoneae RepID = Q6TM44_MAIZE (1e–117); Cupin_1: Cupin (3.6e–34); Cupin_2: Cupin domain (6.8e–07); GO_MF:GO:0046872, metal ion binding# (8e–97); GO_BP:GO:0055114, oxidation reduction# (1e–71); GO_CC:GO:0048046, IDA#apoplast# (8e–97) | 6 | 54.9 | 123777183 | 123778314 |
| 66 | Ribulose bisphosphate carboxylase large chain n = 4 Tax = BEP clade RepID = B8Y2Y5_FESAR (9e–63); RuBisCO_large_N: Ribulose bisphosphate carboxylase large chain, N-terminal domain (1e–79); GO_MF:GO:0016984, ribulose-bisphosphate carboxylase activity# (4e–62); GO_BP:GO:0055114, oxidation reduction# (4e–62); GO_CC:GO:0009536, plastid# (4e–62) | 6 | 55.1 | 123912742 | 123913547 |
| 67 | Putative uncharacterized protein n = 1 Tax = Zea mays RepID = B8A1X9_MAIZE (3e–81) | 6 | 55.1 | 123914152 | 123915257 |
| 68 | Auxin Efflux Carrier family protein n = 1 Tax = Zea mays RepID = B6SV1L_MAIZE (7e–29); GO_BP:GO:0055085, transmembrane transport# (7e–29); GO_CC:GO:0016021, integral to membrane# (7e–29) | 6 | 55.1 | 123949237 | 123949664 |
| 69 | Armadillo/beta-catenin-like repeat family protein n = 1 Tax = Zea mays RepID = B6U4A9_MAIZE (5e–32); GO_MF:GO:0005488, binding# (5e–32) | 6 | 55.1 | 123952012 | 123952497 |
| 70 | Kelch-like protein n = 3 Tax = Oryza sativa RepID = Q84S70_ORYSJ (7e–82); Dev_Cell_Death: Development and cell death domain (7.1e–40); Kelch_1: Kelch motif (0.095); Kelch_1: Kelch motif (1.3e–16); Kelch_2: Kelch motif (6.9e–05); Kelch_1: Kelch motif (4.2e–08); Kelch_2: Kelch motif (8.6); Kelch_1: Kelch motif (5.5e–11); Kelch_2: Kelch motif (0.00044); Kelch_1: Kelch motif (8.5e–14); Kelch_2: Kelch motif (1.5e–05); Kelch_1: Kelch motif (4.4e–05); Kelch_2: Kelch motif (2.3); GO_MF:GO:0005515, protein binding# (5e–40); GO_BP:GO:0050807, IGI#regulation of synapse organization# (7e–38); GO_CC:GO:0005575, cellular_component# (7e–38) | 6 | 55.1 | 124019830 | 124042554 |
| 71 | Kelch-like protein n = 3 Tax = Oryza sativa RepID = Q84S70_ORYSJ (4e–44); Dev_Cell_Death: Development and cell death domain (2.8e–74); Kelch_2: Kelch motif (21); Kelch_1: Kelch motif (0.11); Kelch_1: Kelch motif (0.23); Kelch_2: Kelch motif (15); Kelch_1: Kelch motif (5.4e–12); Kelch_2: Kelch motif (2.3); Kelch_1: Kelch motif (1.2e–12); Kelch_2: Kelch motif (9.9e–06); Kelch_1: Kelch motif (0.004); Kelch_2: Kelch motif (2.4); GO_MF:GO:0005515, protein binding# (1e–26); GO_BP:GO:0046529, IGI#imaginal disc fusion, thorax closure# (6e–26); GO_CC:GO:0031463, IPI#Cul3-RING ubiquitin ligase complex# (6e–26) | 6 | 55.1 | 124104544 | 124110586 |
| 72 | Erg28 like protein n = 4 Tax = Andropogoneae RepID = B6U3K5_MAIZE (9e–68); Erg28: Erg28 like protein (1.6e–36); GO_BP:GO:0016126, IGI#sterol biosynthetic process# (1e–45); GO_CC:GO:0016021, integral to membrane# (2e–68) | 6 | 55.1 | 124135063 | 124140932 |
| 73 | Putative uncharacterized protein Sb02g010980 n = 1 Tax = Sorghum bicolor RepID = C5X573_SORBI (6e–22) | 6 | 55.1 | 124156120 | 124156572 |
| 74 | DNA binding protein n = 1 Tax = Zea mays RepID = B6U8E0_MAIZE (1e–123); HLH: Helix-loop-helix DNA-binding domain (3.5e–07); GO_MF:GO:0030528, transcription regulator activity# (1e–123); GO_BP:GO:0045449, regulation of transcription# (1e–123); GO_CC:GO:0005634, nucleus# (1e–123) | 6 | 55.1 | 124197455 | 124198967 |
| 75 | DNA helicase homolog, putative n = 1 Tax = Musa acuminata RepID = Q1EPC6_MUSAC (6e–10); GO_MF:GO:0004386, helicase activity# (6e–10) | 6 | 55.1 | 124205879 | 124207211 |
| 76 | RuBisCo subunit binding-protein beta subunit (Fragment) n = 1 Tax = Zea mays RepID = Q6B7Q9_MAIZE (5e–62); GO_MF:GO:0005524, ATP binding# (7e–60); GO_BP:GO:0044267, cellular protein metabolic process# (7e–60); GO_CC:GO:0009536, plastid# (7e–60) | 6 | 55.1 | 124214939 | 124216073 |
| 77 | Ulp1 protease family, C-terminal catalytic domain containing protein n = 2 Tax = Oryza sativa Japonica Group RepID = Q109R5_ORYSJ (4e–37); Peptidase_C48: Ulp1 protease family, C-terminal catalytic domain (4.9e–13); GO_MF:GO:0008234, cysteine-type peptidase activity# (1e–158); GO_BP:GO:0006508, proteolysis# (1e–158) | 6 | 55.1 | 124218673 | 124221589 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 78 | Transposon protein, putative, CACTA, En/Spm sub-class n = 1 Tax = Oryza sativa Japonica Group RepID = Q2QWY8_ORYSJ (1e–128); GO_MF:GO:0004803, transposase activity# (2e–57); GO_BP:GO:0006313, transposition, DNA-mediated# (2e–57); | 6 | 55.15 | 124153890 | 124156112 |
| 79 | Glutaryl-CoA dehydrogenase n = 1 Tax = Zea mays RepID = B6TNB5_MAIZE (0.0); Acyl-CoA_dh_N: Acyl-CoA dehydrogenase, N-terminal domain (7e–30); Acyl-CoA_dh_M: Acyl-CoA dehydrogenase, middle domain (1.7e–22); Acyl-CoA_dh_1: Acyl-CoA dehydrogenase, C-terminal do (2.8e–25); Acyl-CoA_dh_2: Acyl-CoA dehydrogenase, C-terminal do (0.0014); GO_MF:GO:0050660, FAD binding# (0.0); GO_BP:GO:0055114, oxidation reduction# (0.0); GO_CC:GO:0009514, glyoxysome# (0.0) | 6 | 55.2 | 124146431 | 124151926 |
| 80 | PHD finger transcription factor-like n = 2 Tax = Oryza sativa RepID = Q5JV7_ORYSJ (1e–153); PHD: PHD-finger (1.8e–10); Acetyltransf_1: Acetyltransferase (GNAT) family (0.074); GO_MF:GO:0046872, metal ion binding# (1e–153); GO_BP:GO:0008152, metabolic process# (1e–153) | 6 | 55.3 | 124296440 | 124300947 |
| 81 | Growth inhibition and differentiation-related protein 88 n = 2 Tax = Andropogoneae RepID = B6TKU0_MAIZE (1e–140); RNA_bind: RNA binding domain (0.027); GO_MF:GO:0046872, metal ion binding# (1e–140); GO_BP:GO:0006402, mRNA catabolic process# (1e–140); GO_CC:GO:0005737, cytoplasm# (1e–140) | 6 | 55.9 | 124363443 | 124366224 |
| 82 | Putative uncharacterized protein n = 1 Tax = Zea mays RepID = B4FS85_MAIZE (4e–14) | 6 | 55.9 | 124471043 | 124472524 |
| 83 | Putative uncharacterized protein n = 3 Tax = Zea mays RepID = B6U549_MAIZE (4e–66) | 6 | 55.9 | 124489396 | 124490221 |
| 84 | Nucleolar complex protein 4 n = 1 Tax = Zea mays RepID = B6SWX2_MAIZE (5e–43); DUF947: Domain of unknown function (DUF947) (0.018); CBF: CBF/Mak21 family (2.7e–05); GO_MF:GO:0005515, protein binding# (1e–19); GO_BP:GO:0006364, rRNA processing# (4e–15); GO_CC:GO:0016020, membrane# (4e–34) | 6 | 55.9 | 124525406 | 124526646 |
| 85 | Fructose-6-phosphate-2-kinase/fructose-2,6-bisphosphatase n = 4 Tax = Andropogoneae RepID = Q947C1_MAIZE (0.0); CBM_20: Starch binding domain (0.0071); 6PF2K: 6-phosphofructo-2-kinase (2.6e–121); PGAM: Phosphoglycerate mutase family (1.6e–33); GO_MF:GO:0030246, carbohydrate binding# (0.0); GO_BP:GO:0016301, kinase activity# (0.0); GO_CC:GO:0043540, IDA#6-phosphofructo-2-kinase/fructose-2,6-biphosphatase 1 complex# (8e–97) | 6 | 55.9 | 124531369 | 124550954 |
| 86 | RING-H2 finger protein ATL3F n = 2 Tax = Zea mays RepID = B6U6T9_MAIZE (2e–75); PHD: PHD-finger (0.066); zf-C3HC4: Zinc finger, C3HC4 type (RING finger) (2.8e–08); GO_MF:GO:0046872, metal ion binding# (2e–75); GO_BP:GO:0010200, IEP#response to chitin# (1e–15); GO_CC:GO:0016021, integral to membrane# (1e–15) | 6 | 55.9 | 124551008 | 124551883 |
| 87 | Putative CCR4-associated factor 1 n = 2 Tax = Oryza sativa RepID = Q5VPG5_ORYSJ (4e–72); CAF1: CAF1 family ribonuclease (8.7e–63); zf-C3HC4: Zinc finger, C3HC4 type (RING finger) (4e–72); GO_BP:GO:0045449, regulation of transcription# (3e–45); GO_CC:GO:0005634, nucleus# (4e–72) | 6 | 55.9 | 124603474 | 124604545 |
| 88 | Protein binding protein, putative n = 1 Tax = Ricinus communis RepID = B9S0N5_RICCO (2e–33); PHD: PHD-finger (0.019); zf-C3HC4: Zinc finger, C3HC4 type (RING finger) (3.6e–07); GO_MF:GO:0046872, metal ion binding# (0.0) | 6 | 56 | 124658046 | 124668099 |
| 89 | PHD finger protein n = 4 Tax = Andropogoneae RepID = B4FK95_MAIZE (1e–107); C1_3: C1-like domain (0.091); PHD: PHD-finger (3.4e–10); GO_MF:GO:0046872, metal ion binding# (1e–107); GO_BP:GO:0046961, proton-transporting ATPase activity, rotational mechanism# (2e–54); GO_CC:GO:0005634, nucleus# (4e–58) | 6 | 56.1 | 124705685 | 124710899 |
| 90 | Arginyl-tRNA synthetase n = 2 Tax = Zea mays RepID = B4FMR1_MAIZE (0.0); Arg_tRNA_synt_N: Arginyl tRNA synthetase N terminal do (1e–183); tRNA-synt_1d: tRNA synthetases class I (R) (9.5e–117); DALR_1: DALR anticodon binding domain (3.7e–48); GO_MF:GO:0016874, ligase activity# (0.0); GO_BP:GO:0006420, arginyl-tRNA aminoacylation# (0.0); GO_CC:GO:0005737, cytoplasm# (0.0) | 6 | 56.2 | 124736591 | 124745075 |
| 91 | Fasciclin-like arabinogalactan protein 8 n = 2 Tax = Zea mays RepID = B6SL10_MAIZE (1e–108); Fasciclin: Fasciclin domain (4.3e–18); GO_CC:GO:0046658, anchored to plasma membrane# (2e–36) | 6 | 56.45 | 124803296 | 124805408 |
| 92 | Arginine/serine-rich splicing factor, putative n = 1 Tax = Ricinus communis RepID = B9SGV2_RICCO (1e–39); zf-CCHC: Zinc knuckle (1.4e–05); zf-CCHC: Zinc knuckle (6.9e–06); GO_MF:GO:0046872, metal ion binding# (1e–39); GO_BP:GO:0008380, RNA splicing# (2e–32) | 6 | 56.8 | 124861967 | 124863604 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 93 | Putative receptor-like protein kinase n = 2 Tax = Oryza sativa RepID = Q75IR9_ORYSJ (0.0); Pkinase: Protein kinase domain (1.9e–32); Pkinase_Tyr: Protein tyrosine kinase (2.3e–23); GO_MF:GO:0016301, kinase activity# (0.0); GO_BP:GO:0016301, kinase activity# (0.0); GO_CC:GO:0016021, integral to membrane# (1e–141) | 6 | 56.8 | 124877371 | 124878770 |
| 94 | Aspartic proteinase oryzasin-1 n = 3 Tax = Zea mays RepID = B6TSQ9_MAIZE (3e–51); GO_MF:GO:0016787, hydrolase activity# (3e–51); GO_BP:GO:0006629, lipid metabolic process# (3e–51); GO_CC:GO:0005773, IDA#vacuole# (1e–41) | 6 | 56.8 | 124956620 | 124957402 |
| 95 | Peroxidase (Fragment) n = 6 Tax = Zea mays RepID = Q6RFK0_MAIZE (0.0); peroxidase: Peroxidase (2.4e–134); GO_MF:GO:0046872, metal ion binding# (0.0); GO_BP:GO:0055114, oxidation reduction# (0.0); GO_CC:GO:0016021, integral to membrane# (2e–84) | 6 | 56.8 | 125011395 | 125012945 |
| 96 | Peroxidase (Fragment) n = 6 Tax = Zea mays RepID = Q6RFK0_MAIZE (1e–157); peroxidase: Peroxidase (4.3e–134); GO_MF:GO:0046872, metal ion binding# (0.0); GO_BP:GO:0055114, oxidation reduction# (0.0); GO_CC:GO:0016021, integral to membrane# (5e–86) | 6 | 56.8 | 125155203 | 125156888 |
| 97 | Chloroplast RelA homologue 2 n = 2 Tax = Oryza sativa Japonica Group RepID = Q9AYT4_ORYSJ (0.0); RelA_SpoT: Region found in RelA/SpoT proteins (6.3e–46); efhand: EF hand (0.0012); efhand: EF hand (0.043); GO_MF:GO:0005509, calcium ion storage activity# (0.0); GO_BP:GO:0015969, guanosine tetraphosphate metabolic process# (0.0); GO_CC:GO:0009507, chloroplast# (1e–149) | 6 | 56.8 | 125187331 | 125190275 |
| 98 | Dihydrolipoyl dehydrogenase 2 n = 3 Tax = Poaceae RepID = B9FML1_ORYSJ (1e–61); Pyr_redox_2: Pyridine nucleotide-disulphide oxidored (0.0013); Pyr_redox: Pyridine nucleotide-disulphide oxidore (8.3e–16); GO_MF:GO:0050660, FAD binding# (1e–61); GO_BP:GO:0055114, oxidation reduction# (1e–61); GO_CC:GO:0005737, cytoplasm# (1e–61) | 6 | 56.8 | 125286546 | 125310756 |
| 99 | Retrotransposon protein, putative, unclassified n = 1 Tax = Oryza sativa Japonica Group RepID = Q2QSA6_ORYSJ (1e–70); GO_MF:GO:0003677, DNA binding# (1e–70); GO_BP:GO:0015074, DNA integration# (1e–70); GO_CC:GO:0005634, nucleus# (7e–67) | 6 | 56.8 | 125334886 | 125345192 |
| 100 | Alpha-L-fucosidase 2 n = 3 Tax = Zea mays RepID = B6TDT3_MAIZE (0.0); Lipase_GDSL: GDSL-like Lipase/Acylhydrolase (9.8e–76); GO_MF:GO:0016788, hydrolase activity, acting on ester bonds# (7e–46); GO_BP:GO:0006629, lipid metabolic process# (0.0); GO_CC:GO:0005576, extracellular region# (8e–88) | 6 | 56.8 | 125454576 | 125459572 |
| 101 | Ubiquitin-protein ligase, putative n = 1 Tax = Ricinus communis RepID = B9RZW1_RICCO (1e–114); HECT: HECT-domain (ubiquitin-transferase) (4.5e–53); GO_MF:GO:0016881, acid-amino acid ligase activity# (1e–123); GO_BP:GO:0006464, protein modification process# (1e–123); GO_CC:GO:0005622, intracellular# (1e–123) | 6 | 56.8 | 125545211 | 125554393 |
| 102 | Ubiquitin-protein ligase, putative n = 1 Tax = Ricinus communis RepID = B9RZW1_RICCO (2e–32); GO_MF:GO:0016881, acid-amino acid ligase activity# (7e–46); GO_BP:GO:0006464, protein modification process# (7e–46); GO_CC:GO:0005622, intracellular# (7e–46) | 6 | 56.8 | 125612410 | 125613737 |
| 103 | Putative aldose reductase-related protein n = 1 Tax = Zea mays RepID = Q7FS90_MAIZE (2e–19); Kelch_1: Kelch motif (1.6e–06); Kelch_2: Kelch motif (0.00097); GO_MF:GO:0005515, protein binding# (5e–46); GO_BP:GO:0055114, oxidation reduction# (2e–19) | 6 | 56.8 | 125628803 | 125629340 |
| 104 | Protein phosphatase 2C 35 n = 2 Tax = Oryza sativa RepID = P2C35_ORYSJ (5e–40); GO_MF:GO:0046872, metal ion binding# (5e–40); GO_BP:GO:0006952, defense response# (5e–40); GO_CC:GO:0016020, membrane# (5e–40) | 6 | 56.8 | 125630885 | 125631928 |
| 105 | Replication protein A 70 kDa DNA-binding subunit n = 3 Tax = Zea mays RepID = B6SL03_MAIZE (1e–141); Rep_fac-A_C: Replication factor-A C terminal domain (4e–66); GO_MF:GO:0003677, DNA binding# (1e–141); GO_BP:GO:0006260, DNA replication# (1e–141); GO_CC:GO:0005634, nucleus# (1e–141) | 6 | 56.8 | 125632605 | 125635951 |
| 106 | Retrotransposon protein, putative, Ty1-copia subclass n = 1 Tax = Oryza sativa Japonica Group RepID = Q2R0F7_ORYSJ (8e–17); GO_MF:GO:0003677, DNA binding# (8e–17); GO_BP:GO:0015074, DNA integration# (8e–17) | 6 | 56.8 | 125879055 | 125879270 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 107 | Gibberellin 2-oxidase n = 1 Tax = Zea mays RepID = B6U889_MAIZE (1e–139); 2OG-FeII_Oxy: 2OG-Fe(II) oxygenase superfamily (0.008); GO_MF:GO:0016491, oxidoreductase activity# (1e–139); GO_BP:GO:0055114, oxidation reduction# (1e–139); GO_CC:GO:0016020, membrane# (3e–42) | 6 | 56.8 | 125881243 | 125886353 |
| 108 | Putative gag-pol polyprotein n = 1 Tax = Oryza sativa Japonica Group RepID = Q6UUN3_ORYSJ (4e–33); GO_MF:GO:0004190, penicillopepsin activity# (4e–33); GO_BP:GO:0015074, DNA integration# (4e–33); GO_CC:GO:0005634, nucleus# (9e–29) | 6 | 56.8 | 125909464 | 125910136 |
| 109 | ATP citrate lyase b-subunit n = 3 Tax = Papilionoideae RepID = Q93YH3_LUPAL (6e–21); GO_MF:GO:0005524, ATP binding# (6e–23); GO_BP:GO:0006085, NAS#acetyl-CoA biosynthetic process# (1e–19) | 6 | 56.8 | 126000743 | 126001820 |
| 110 | Putative aspartic proteinase nepenthesin I n = 1 Tax = Oryza sativa Japonica Group RepID = Q69IP6_ORYSJ (9e–45); Asp: Eukaryotic aspartyl protease (1.6e–05); GO_MF:GO:0004190, penicillopepsin activity# (9e–45); GO_BP:GO:0006508, proteolysis# (9e–45); GO_CC:GO:0005576, extracellular region# (4e–41) | 6 | 56.8 | 126012128 | 126013728 |
| 111 | Transposon protein, putative, CACTA, En/Spm sub-class n = 1 Tax = Oryza sativa Japonica Group RepID = Q10BK1_ORYSJ (5e–59); GO_MF:GO:0004803, transposase activity# (4e–92); GO_BP:GO:0006313, transposition, DNA-mediated# (4e–92); GO_CC:GO:0016020, membrane# (1e–33) | 6 | 56.8 | 126014170 | 126016932 |
| 112 | Putative uncharacterized protein n = 1 Tax = Zea mays RepID = C0PP88_MAIZE (3e–32) | 6 | 56.8 | 126063923 | 126064225 |
| 113 | Putative uncharacterized protein Sb09g004490 n = 1 Tax = Sorghum bicolor RepID = C5ZOL6_SORBI (4e–18); GO_MF:GO:0030528, transcription regulator activity# (7e–10); GO_BP:GO:0045449, regulation of transcription# (7e–10); GO_CC:GO:0005634, nucleus# (7e–10) | 6 | 56.8 | 126090413 | 126091289 |
| 114 | Putative uncharacterized protein n = 1 Tax = Zea mays RepID = C4JC40_MAIZE (8e–11) | 6 | 56.8 | 126126609 | 126126863 |
| 115 | CID11 n = 3 Tax = Andropogoneae RepID = B4FZ16_MAIZE (1e–41); GO_MF:GO:0003676, nucleic acid binding# (1e–41); GO_BP:GO:0006397, mRNA processing# (4e–20); GO_CC:GO:0005634, nucleus# (4e–20) | 6 | 56.8 | 126130008 | 126133974 |
| 116 | USP family protein n = 4 Tax = Andropogoneae RepID = B6TC12_MAIZE (4e–65); Usp: Universal stress protein family (1.6e–20); GO_MF:GO:0016818, hydrolase activity, acting on acid anhydrides, in phosphorus-containing anhydrides# (1e–55); GO_BP:GO:0006950, response to stress# (4e–65); GO_CC:GO:0005634, nucleus# (1e–55) | 6 | 56.8 | 126146579 | 126149276 |
| 117 | DNA-directed RNA polymerase II 19 kDa polypeptide n = 2 Tax = Andropogoneae RepID = B4FXC7_MAIZE (2e–98); RNA_pol_Rpb7_N: RNA polymerase Rpb7, N-terminal domain (6.2e–13); RNA_pol_Rbc25: RNA polymerase III subunit Rpc25 (0.059); GO_MF:GO:0003899, DNA-directed RNA polymerase III activity# (2e–98); GO_BP:GO:0006350, transcription# (2e–98); GO_CC:GO:0080137, IPI#DNA-directed RNA polymerase V complex# (1e–48) | 6 | 56.8 | 126149278 | 126152151 |
| 118 | Putative uncharacterized protein Sb10g005530 n = 1 Tax = Sorghum bicolor RepID = C5ZSH0_SORBI (6e–25) | 6 | 56.8 | 126152259 | 126152825 |
| 119 | Pyrophosphate-energized vacuolar membrane proton pump n = 2 Tax = Andropogoneae RepID = B6UEE8_MAIZE (0.0); H_PPase: Inorganic H+ pyrophosphatase (0); OPT: OPT oligopeptide transporter protein (0.048); DUF540: Protein of unknown function (DUF540) (0.096); GO_MF:GO:0009678, hydrogen-translocating pyrophosphatase activity# (0.0); GO_BP:GO:0015992, proton transport# (0.0); GO_CC:GO:0016020, membrane# (0.0) | 6 | 56.8 | 126196881 | 126200082 |
| 120 | Putative uncharacterized protein n = 1 Tax = Zea mays RepID = B6U5J9_MAIZE (2e–16) | 6 | 56.8 | 126286798 | 126287445 |
| 121 | Putative polyprotein n = 1 Tax = Oryza sativa Japonica Group RepID = Q65XD2_ORYSJ (2e–16); GO_MF:GO:0004190, penicillopepsin activity# (2e–16); GO_BP:GO:0015074, DNA integration# (2e–16); GO_CC:GO:0005634, nucleus# (8e–16) | 6 | 56.8 | 126290188 | 126291608 |
| 122 | Polyprotein n = 1 Tax = Oryza sativa Japonica Group RepID = Q8W150_ORYSJ (1e–30); GO_MF:GO:0003964, RNA-directed DNA polymerase, group II intron encoded# (1e–30); GO_BP:GO:0015074, DNA integration# (1e–30); GO_CC:GO:0005634, nucleus# (1e–30) | 6 | 56.8 | 126292009 | 126292632 |
| 123 | Putative SMEK homolog 3 n = 2 Tax = Mus musculus RepID = SMEK3_MOUSE (8e–19); GO_MF:GO:0005488, binding# (2e–47) | 6 | 56.8 | 126343969 | 126349725 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 124 | Putative polyprotein n = 1 Tax = Zea mays RepID = Q8SA93_MAIZE (1e-160); DUF625: Protein of unknown function (DUF625) (8.6e-57); GO_MF:GO:0003964, RNA-directed DNA polymerase, group II intron encoded# (1e-160); GO_BP:GO:0015074, DNA integration# (1e-160); GO_CC:GO:0005634, nucleus# (1e-160) | 6 | 56.8 | 126358241 | 126418203 |
| 125 | OSJNBa0065O17.7 protein n = 1 Tax = Oryza sativa Japonica Group RepID = Q7XPS4_ORYSJ (2e-40); GO_MF:GO:0003964, RNA-directed DNA polymerase, group II intron encoded# (2e-40); GO_BP:GO:0015074, DNA integration# (2e-40) | 6 | 56.8 | 126362377 | 126368009 |
| 126 | Tubulin gamma-1 chain n = 28 Tax = Embryophyta RepID = TBG1_ARATH (0.0); Tubulin: Tubulin/FtsZ family, GTPase domain (3.7e-94); Tubulin_C: Tubulin/FtsZ family, C-terminal domain (1.2e-58); GO_MF:GO:0005525, GTP binding# (0.0); GO_BP:GO:0051641, IMP#cellular localization# (0.0); GO_CC:GO:0043234, protein complex# (0.0) | 6 | 56.8 | 126579166 | 126583379 |
| 127 | Putative uncharacterized protein Sb01g009200 n = 3 Tax = Andropogoneae RepID = C5WIY8_SORBI (1e-26); GO_MF:GO:0008375, acetylglucosaminyltransferase activity# (1e-11); GO_CC:GO:0016020, membrane# (1e-11) | 6 | 56.8 | 126648784 | 126649020 |
| 128 | Chaperone protein dnaJ, putative n = 1 Tax = Ricinus communis RepID = B9RNG7_RICCO (1e-141); DnaJ: DnaJ domain (1e-36); DnaJ_C: DnaJ C terminal region (1.6e-18); GO_MF:GO:0051082, unfolded protein binding# (1e-145); GO_BP:GO:0006457, protein folding# (1e-145); GO_CC:GO:0005886, plasma membrane# (1e-139) | 6 | 56.8 | 126678899 | 126686639 |
| 129 | Putative uncharacterized protein Sb02g029480 n = 2 Tax = Andropogoneae RepID = C5X5A3_SORBI (8e-23); GO_MF:GO:0005515, protein binding# (5e-16); GO_CC:GO:0005737, cytoplasm# (5e-16) | 6 | 56.8 | 126761961 | 126762272 |
| 130 | Protein disulfide isomerase n = 2 Tax = Andropogoneae RepID = Q5EUD6_MAIZE (0.0); Thioredoxin: Thioredoxin (2.5e-49); AhpC-TSA: AhpC/TSA family (0.034); GO_MF:GO:0016853, isomerase activity# (0.0); Endoplasmin reticulum ERp29, C-te (3.3e-46); GO_MF:GO:0016853, isomerase activity# (0.0); GO_BP:GO:0045454, cell redox homeostasis# (0.0); GO_CC:GO:0005783, IDA#endoplasmic reticulum# (0.0) | 6 | 56.8 | 126779705 | 126784442 |
| 131 | Retrotransposon protein, putative, unclassified n = 2 Tax = Oryza sativa Japonica Group RepID = Q2QZV1_ORYSJ (2e-26); GO_MF:GO:0003964, RNA-directed DNA polymerase, group II intron encoded# (2e-29); GO_BP:GO:0006278, RNA-dependent DNA replication# (2e-29); GO_CC:GO:0005634, nucleus# (4e-21) | 6 | 56.8 | 126790130 | 126790810 |
| 132 | Gamma-tubulin complex component, putative n = 1 Tax = Ricinus communis RepID = B9SAS5_RICCO (0.0); Spc97_Spc98: Spc97/Spc98 family (9.1e-144); GO_MF:GO:0005515, protein binding# (0.0); GO_CC:GO:0005815, microtubule organizing center# (0.0); GO_BP:GO:0000226, microtubule cytoskeleton organization# (0.0) | 6 | 56.8 | 126812997 | 126837059 |
| 133 | Putative AC transposase n = 1 Tax = Zea mays RepID = TRA1_MAIZE (0.0); zf-BED: BED zinc finger (4.4e-05); hATC: hAT family dimerisation domain (1.2e-38); GO_MF:GO:0046983, protein dimerization activity# (0.0); GO_BP:GO:0032196, transposition# (0.0) | 6 | 56.8 | 126822114 | 126824371 |
| 134 | Putative polyprotein n = 1 Tax = Zea mays RepID = Q8SA93_MAIZE (2e-26); GO_MF:GO:0003964, RNA-directed DNA polymerase, group II intron encoded# (2e-26); GO_BP:GO:0015074, DNA integration# (2e-26); GO_CC:GO:0005634, nucleus# (2e-26) | 6 | 56.8 | 126826110 | 126831487 |
| 135 | F6D8.18 protein n = 11 Tax = rosids RepID = Q9SSR2_ARATH (1e-22); GO_MF:GO:0008233, peptidase activity# (1e-24); GO_BP:GO:0006508, proteolysis# (1e-24); GO_CC:GO:0016020, membrane# (1e-24) | 6 | 56.8 | 126872786 | 126877517 |
| 136 | Ulp1 protease family, C-terminal catalytic domain containing protein n = 2 Tax = Oryza sativa Japonica Group RepID = Q109R5_ORYSJ (5e-34); Peptidase_C48: Ulp1 protease family, C-terminal catalytic domain (5.8e-13); GO_MF:GO:0008234, cysteine-type peptidase activity# (1e-129); GO_BP:GO:0006508, proteolysis# (1e-129) | 6 | 56.8 | 126877369 | 126879300 |
| 137 | VIP2 protein n = 1 Tax = Avena fatua RepID = Q9M4C5_AVEFA (1e-171); zf-C3HC4: Zinc finger, C3HC4 type (RING finger) (4.8e-05); zf-RING-like: RING-like domain (0.095); GO_MF:GO:0046872, metal ion binding# (1e-171); GO_BP:GO:0004842, NAS#ubiquitin-protein ligase activity# (2e-43) | 6 | 56.8 | 126957235 | 126967077 |
| 138 | Putative ABI3-interacting protein 2 n = 1 Tax = Oryza sativa Japonica Group RepID = Q6K486_ORYSJ (5e-09); GO_BP:GO:0000226, microtubule cytoskeleton organization# (5e-09); GO_CC:GO:0005874, microtubule (5e-09) | 6 | 56.8 | 126982783 | 126983154 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 139 | ATP binding protein n = 2 Tax = Andropogoneae RepID = B6SXM5_MAIZE (0.0); Kinesin: Kinesin motor domain (1.2e-125); GO_MF:GO:0005524, ATP binding# (0.0); GO_BP:GO:0007018, microtubule-based movement# (0.0); GO_CC:GO:0005874, microtubule# (0.0) | 6 | 56.8 | 127109946 | 127127395 |
| 140 | Putative polyprotein n = 1 Tax = Zea mays RepID = Q8SA93_MAIZE (2e-62); RVT_1: Reverse transcriptase (RNA-dependent DN (0.00015); GO_MF:GO:0003964, RNA-directed DNA polymerase, group II intron encoded# (2e-62); GO_BP:GO:0015074, DNA integration# (2e-62); GO_CC:GO:0005634, nucleus# (2e-62) | 6 | 56.8 | 127112084 | 127116226 |
| 141 | Putative polyprotein n = 1 Tax = Zea mays RepID = Q8SA93_MAIZE (1e-28); GO_MF:GO:0003964, RNA-directed DNA polymerase, group II intron encoded# (1e-28); GO_BP:GO:0006355, regulation of transcription, DNA-dependent# (1e-34); GO_CC:GO:0005634, nucleus# (1e-34) | 6 | 56.8 | 127116846 | 127117349 |
| 142 | Putative polyprotein n = 1 Tax = Zea mays RepID = Q8SA93_MAIZE (6e-62); GO_MF:GO:0003964, RNA-directed DNA polymerase, group II intron encoded# (6e-62); GO_BP:GO:0015074, DNA integration# (6e-62); GO_CC:GO:0005634, nucleus# (6e-62) | 6 | 56.8 | 127129438 | 127130136 |
| 143 | Serine/threonine-protein phosphatase n = 2 Tax = Andropogoneae RepID = C5Z010_SORBI (1e-175); Metallophos: Calcineurin-like phosphoesterase (1.3e-44); GO_MF:GO:0016787, hydrolase activity# (1e-163); GO_BP:GO:0004721, phosphoprotein phosphatase activity# (1e-163); GO_CC:GO:0016459, myosin complex# (1e-128) | 6 | 56.8 | 127199789 | 127203947 |
| 144 | Putative uncharacterized protein n = 1 Tax = Zea mays RepID = B6UAL2_MAIZE (2e-23) | 6 | 56.8 | 127262064 | 127265900 |
| 145 | Putative uncharacterized protein n = 1 Tax = Zea mays RepID = B6UAL2_MAIZE (3e-17) | 6 | 56.8 | 127283052 | 127283372 |
| 146 | HAT family dimerisation domain containing protein n = 1 Tax = Oryza sativa Japonica Group RepID = Q8LNK9_ORYSJ (0.0); zf-BED: BED zinc finger (9.6e-08); hATC: hAT family dimerisation domain (4.6e-39); GO_MF:GO:0046983, protein dimerization activity# (0.0); GO_BP:GO:0006468, protein amino acid phosphorylation# (3e-92) | 6 | 56.8 | 127360096 | 127364045 |
| 147 | Ribosomal protein L18 n = 16 Tax = Poaceae RepID = Q5WMY3_ORYSJ (3e-99); Ribosomal_L18e: Eukaryotic ribosomal protein L18 (7.2e-127); GO_MF:GO:0003735, structural constituent of ribosome# (3e-99); GO_BP:GO:0006412, translation# (3e-99); GO_CC:GO:0030529, ribonucleoprotein complex# (3e-99) | 6 | 56.8 | 127372821 | 127376997 |
| 148 | Ethylene receptor protein n = 1 Tax = Musa acuminata AAA Group RepID = A1IIY0_MUSAC (0.0); GAF: GAF domain (1.6e-07); HisKA: His Kinase A (phosphoacceptor) domain (6.3e-20); HATPase_c: Histidine kinase-, DNA gyrase B-, and HSP90-like ATPase (4.6e-31); GO_MF:GO:0016772, transferase activity, transferring phosphorus-containing groups# (0.0); GO_BP:GO:0018106, peptidyl-histidine phosphorylation# (0.0); GO_CC:GO:0016020, membrane# (0.0) | 6 | 56.8 | 127377761 | 127381836 |
| 149 | Putative uncharacterized protein Sb09g004315 (Fragment) n = 1 Tax = Sorghum bicolor RepID = C5Z0J6_SORBI (1e-14); GO_MF:GO:0046872, metal ion binding# (2e-09); GO_BP:GO:0006355, regulation of transcription, DNA-dependent# (2e-09) | 6 | 56.8 | 127445565 | 127447307 |
| 150 | Importin subunit alpha-1b n = 5 Tax = Poaceae RepID = IMA1B_ORYSJ (0.0); IBB: Importin beta binding domain (8.7e-27); Arm: Armadillo/beta-catenin-like repeat (4); HEAT: HEAT repeat (30); Arm: Armadillo/beta-catenin-like repeat (5.1e-11); HEAT: HEAT repeat (5.1); Arm: Armadillo/beta-catenin-like repeat (1.3e-14); HEAT: HEAT repeat (8.1e-05); Arm: Armadillo/beta-catenin-like repeat (4.5e-08); Arm: Armadillo/beta-catenin-like repeat (1.1e-06); HEAT: HEAT repeat (1.5); Arm: Armadillo/beta-catenin-like repeat (2.1e-10); HEAT: HEAT repeat (1.5); Arm: Armadillo/beta-catenin-like repeat (8e-11); HEAT: HEAT repeat (9.3); Arm: Armadillo/beta-catenin-like repeat (1.7e-13); HEAT: HEAT repeat (30); Arm: Armadillo/beta-catenin-like repeat (4.5e-07); HEAT: HEAT repeat (37); GO_MF:GO:0008565, protein transporter activity# (0.0); GO_BP:GO:0015031, protein transport# (0.0); GO_CC:GO:0048471, ISS#perinuclear region of cytoplasm# (0.0) | 6 | 56.8 | 127496705 | 127501662 |
| 151 | WRKY67-superfamily of TFs having WRKY and zinc finger domains n = 2 Tax = Zea mays RepID = B6T4Y9_MAIZE (7e-51); FAR1: FAR1 family (0.0056); WRKY: WRKY DNA-binding domain (7.5e-36); GO_MF:GO:0043565, sequence-specific DNA binding# (4e-81); GO_BP:GO:0045449, regulation of transcription# (4e-81); GO_CC:GO:0005634, nucleus# (4e-81) | 6 | 56.8 | 127590782 | 127592172 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 152 | Putative uncharacterized protein Sb05g019580 n = 1 Tax = Sorghum bicolor RepID = C5Y395_SORBI (2e−10) | 6 | 56.8 | 127598820 | 127599045 |
| 153 | Putative uncharacterized protein n = 2 Tax = Zea mays RepID = B6SQA8_MAIZE (8e−56) | 6 | 56.8 | 127633793 | 127634935 |
| 154 | H0103C06.4 protein n = 1 Tax = Oryza sativa RepID = Q259H8_ORYSA (4e−28); GO_MF:GO:0046983, protein dimerization activity# (3e−28) | 6 | 56.8 | 127659907 | 127661365 |
| 155 | Alpha-L-fucosidase 2 n = 2 Tax = Zea mays RepID = B6TLP8_MAIZE (2e−66); Lipase_GDSL: GDSL-like Lipase/Acylhydrolase (3.5e−07); Gp_dh_N: Glyceraldehyde 3-phosphate dehydrogenase, (1.3e−07); GO_MF:GO:0016788, hydrolase activity, acting on ester bonds# (1e−113); GO_BP:GO:0006629, lipid metabolic process# (1e−113); GO_CC:GO:0005576, extracellular region# (2e−49) | 6 | 56.8 | 127663965 | 127666621 |
| 156 | Putative uncharacterized protein n = 2 Tax = Zea mays RepID = B6SQA8_MAIZE (2e−81) | 6 | 56.8 | 127687297 | 127688865 |
| 157 | OSJNBa0040D17.12 protein n = 2 Tax = Oryza sativa Japonica Group RepID = Q7XX95_ORYSJ (1e−148); Transferase: Transferase family (1.6e−40); GO_MF:GO:0016747, transferase activity, transferring acyl groups other than amino-acyl groups# (1e−146) | 6 | 56.8 | 127714984 | 127716689 |
| 158 | Putative uncharacterized protein Sb09g005695 n = 3 Tax = Andropogoneae RepID = C5YU84_SORBI (1e−180); GO_MF:GO:0004803, transposase activity# (2e−43); GO_BP:GO:0006313, transposition, DNA-mediated# (2e−43) | 6 | 56.8 | 127766680 | 127770452 |
| 159 | BZIP transcription factor bZIP109 n = 3 Tax = Glycine max RepID = Q0QPG4_SOYBN (5e−49); DUF1664: Protein of unknown function (DUF1664) (3.1e−67) | 6 | 56.8 | 127774370 | 127787122 |
| 160 | Putative uncharacterized protein Sb08g000780 n = 1 Tax = Sorghum bicolor RepID = C5YQ53_SORBI (3e−20) | 6 | 56.8 | 127859677 | 127860013 |
| 161 | FACT complex subunit SSRP1-B n = 3 Tax = Oryza sativa RepID = SSP1B_ORYSJ (0.0); SSrecog: Structure-specific recognition protein (4.6e−144); Rtt106: Histone chaperone Rttp106-like (1.2e−56); HMG_box: HMG (high mobility group) box (3.2e−22); GO_MF:GO:0003677, DNA binding# (0.0); GO_BP:GO:0045449, regulation of transcription# (0.0); GO_CC:GO:0005694, chromosome# (0.0) | 6 | 56.8 | 127883928 | 127890893 |
| 162 | Tetratricopeptide repeat domain protein n = 1 Tax = Microcoleus chthonoplastes PCC 7420 RepID = B4VZS1_9CYAN (6e−15); TPR_2: Tetratricopeptide repeat (0.072); TPR_2: Tetratricopeptide repeat (4.7); TPR_2: Tetratricopeptide repeat (28); GO_MF:GO:0005488, binding# (1e−160); GO_BP:GO:0019684, photosynthesis, light reaction# (2e−15); GO_CC:GO:0009941, IDA#chloroplast envelope# (5e−27) | 6 | 56.8 | 127893148 | 127895627 |
| 163 | Bifunctional protein tiIS/hprT n = 3 Tax = Andropogoneae RepID = B6SSV8_MAIZE (3e−85); Pribosyltran: Phosphoribosyl transferase domain (2.3e−24); GO_MF:GO:0016740, transferase activity# (3e−85); GO_BP:GO:0009116, nucleoside metabolic process# (3e−85); GO_CC:GO:0005737, cytoplasm# (3e−85) | 6 | 56.8 | 127898464 | 127901020 |
| 164 | 3′-N-debenzoyltaxol N-benzoyltransferase-like n = 2 Tax = Oryza sativa RepID = Q9LGF6_ORYSJ (1e−170); Transferase: Transferase family (1.5e−49); GO_MF:GO:0016747, transferase activity, transferring acyl groups other than amino-acyl groups# (0.0) | 6 | 56.8 | 128052937 | 128055250 |
| 165 | 60S ribosomal protein L13 n = 14 Tax = Poaceae RepID = Q7XJB4_ORYSJ (1e−60); Ribosomal_L13e: Ribosomal protein L13e (1.6e−90); GO_MF:GO:0003735, structural constituent of ribosome# (1e−60); GO_BP:GO:0006412, translation# (1e−60); GO_CC:GO:0030529, ribonucleoprotein complex# (1e−60) | 6 | 56.8 | 128062357 | 128064852 |
| 166 | PRP38 pre-mRNA processing factor 38 domain containing B n = 3 Tax = Andropogoneae RepID = B6TSE1_MAIZE (1e−112); PRP38: PRP38 family (1.4e−26); DUF1777: Protein of unknown function (DUF1777) (0.022); GO_MF:GO:0004437, inositol or phosphatidylinositol phosphatase activity# (9e−37); GO_BP:GO:0009651, IEP#response to salt stress# (1e−110); GO_CC:GO:0005681, spliceosomal complex# (4e−38) | 6 | 56.8 | 128201353 | 128207921 |
| 167 | Macrophage erythroblast attacher n = 2 Tax = Andropogoneae RepID = B6TIF70_MAIZE (1e−133); GO_MF:GO:0003779, actin binding# (2e−40); GO_BP:GO:0051301, cell division# (2e−40); GO_CC:GO:0016363, nuclear matrix# (2e−40) | 6 | 56.85 | 125268872 | 125272587 |
| 168 | Protein TOC75, chloroplastic n = 3 Tax = Oryza sativa RepID = TOC75_ORYSJ (2e−22); GO_MF:GO:0015450, P-P-bond-hydrolysis-driven protein transmembrane transporter activity# (3e−19); GO_BP:GO:0015031, protein transport# (2e−22); GO_CC:GO:0019867, outer membrane# (2e−22) | 6 | 56.9 | 125224666 | 125225259 |

TABLE 18-continued

Annotated coding sequences within ASR-6.01 region.

| Gene ID | Annotation | Chr | MON Map cM† | Physical Map Position bp †† Start | End |
|---|---|---|---|---|---|
| 169 | Ribosomal protein S27a, isoform CRA_c n = 9 Tax = Euteleostomi RepID = B2RDW1_HUMAN (4e−59); ubiquitin: Ubiquitin family (2.9e−38); Ribosomal_S27: Ribosomal protein S27a (4.2e−30); GO_MF:GO:0003735, structural constituent of ribosome# (1e−57); GO_BP:GO:0006412, translation# (1e−57); GO_CC:GO:0005840, ribosome# (1e−57) | 6 | 56.9 | 125241154 | 125242015 |
| 170 | Retrotransposon protein, putative, Ty3-gypsy subclass n = 2 Tax = Oryza sativa RepID = Q7XGB8_ORYSJ (8e−10); GO_MF:GO:0008270, zinc ion binding# (8e−10); GO_BP:GO:0015074, DNA integration# (8e−10) | 6 | 56.9 | 125241943 | 125247539 |
| 171 | Retrotransposon protein, putative, unclassified n = 1 Tax = Oryza sativa Japonica Group RepID = Q2R3U8_ORYSJ (7e−66); GO_MF:GO:0003677, DNA binding# (7e−66); GO_BP:GO:0015074, DNA integration# (7e−66) | 6 | 56.9 | 125247227 | 125248186 |
| 172 | WD-repeat protein, putative n = 1 Tax = Ricinus communis RepID = B9RVD2_RICCO (3e−33); GO_BP:GO:0010072, IGI#primary shoot apical meristem specification# (2e−33); GO_CC:GO:0005829, IDA#cytosol# (3e−33) | 6 | 56.9 | 125265027 | 125267222 |
| 173 | Putative uncharacterized protein n = 1 Tax = Zea mays RepID = B6T0R3_MAIZE (4e−13); DVL: DVL family (1.1e−08) | 6 | 56.9 | 128132458 | 128133047 |
| 174 | Protein binding protein n = 2 Tax = Andropogoneae RepID = B6TV66_MAIZE (0.0); PHD: PHD-finger (0.048); zf-C3HC4: Zinc finger, C3HC4 type (RING finger) (6.8e−09); GO_MF:GO:0046872, metal ion binding# (0.0); GO_CC:GO:0005886, plasma membrane# (5e−23) | 6 | 56.9 | 128159679 | 128163410 |
| 175 | Putative serine/threonine protein phosphatase 2A (PP2A) regulatory subunit B' (B'gamma) n = 1 Tax = Oryza sativa Japonica Group RepID = Q5VRD6_ORYSJ (0.0); B56: Protein phosphatase 2A regulatory B subunit (B56 family) (7.4e−224); GO_MF:GO:0008601, protein phosphatase type 2A regulator activity# (0.0); GO_BP:GO:0008601, protein phosphatase type 2A regulator activity# (0.0); GO_CC:GO:0000159, protein phosphatase type 2A complex# (0.0) | 6 | 56.9 | 128299646 | 128308939 |
| 176 | Gibberellin 3-beta-dioxygenase 2-2 n = 4 Tax = Zea mays RepID = B6UAD7_MAIZE (0.0); 2OG-FeII_Oxy: 2OG-Fe(II) oxygenase superfamily (3.8e−29); GO_MF:GO:0016702, oxidoreductase activity, acting on single donors with incorporation of molecular oxygen, incorporation of two atoms of oxygen# (0.0); GO_BP:GO:0055114, oxidation reduction# (0.0); GO_CC:GO:0005737, cytoplasm# (1e−51) | 6 | 56.9 | 128315121 | 128316850 |
| 177 | Ankyrin repeat family protein-like n = 2 Tax = Oryza sativa RepID = Q69TB9_ORYSJ (4e−66); Ank: Ankyrin repeat (11); Ank: Ankyrin repeat (0.41); Ank: Ankyrin repeat (0.23); Ank: Ankyrin repeat (0.0015); Ank: Ankyrin repeat (2.9); Ank: Ankyrin repeat (0.006); GO_MF:GO:0008234, cysteine-type peptidase activity# (4e−66) | 6 | 56.9 | 128318222 | 128321074 |
| 178 | Cytokinin-O-glucosyltransferase 1 n = 2 Tax = Zea mays RepID = B4FAT6_MAIZE (0.0); UDPGT: UDP-glucoronosyl and UDP-glucosyl transferase (3e−07); GO_MF:GO:0016758, transferase activity, transferring hexosyl groups## (0.0); GO_BP:GO:0008152, metabolic process## (0.0); GO_CC:GO:0016021, integral to membrane# (1e−104) | 6 | 57 | 128420330 | 128421841 |
| 179 | Probable cellulose synthase A catalytic subunit 1 [UDP-forming] n = 15 Tax = Poaceae RepID = CESA1_ORYSJ (0.0); PHD: PHD-finger (0.011); zf-C3HC4: Zinc finger, C3HC4 type (RING finger) (0.05); Cellulose_synt: Cellulose synthase (0); GO_MF:GO:0046872, metal ion binding# (0.0); GO_BP:GO:0030244, cellulose biosynthetic process# (0.0); GO_CC:GO:0016021, integral to membrane# (0.0) | 6 | 57.05 | 128560617 | 128567283 |
| 180 | Putative uncharacterized protein n = 1 Tax = Zea mays RepID = B6TYR3_MAIZE (2e−39); GO_MF:GO:0005488, binding# (9e−11) | 6 | 57.1 | 128455019 | 128455534 |
| 181 | Putative uncharacterized protein n = 2 Tax = Zea mays RepID = B6SN58_MAIZE (5e−31); GO_MF:GO:0005488, binding# (1e−09) | 6 | 57.1 | 128465318 | 128466183 |
| 182 | Putative uncharacterized protein Sb09g005320 n = 2 Tax = Andropogoneae RepID = C5Z157_SORBI (1e−20) | 6 | 57.1 | 128467513 | 128484308 |
| 183 | 17.5 kDa class II heat shock protein n = 1 Tax = Zea mays RepID = B6U175_MAIZE (3e−52); HSP20: Hsp20/alpha crystallin family (0.0014); GO_MF:GO:0051082, unfolded protein binding# (9e−11); GO_BP:GO:0006950, response to stress# (3e−52); GO_CC:GO:0005737, cytoplasm# (1e−35) | 6 | 57.1 | 128470652 | 128471159 |
| 184 | Putative uncharacterized protein Sb04g007000 n = 1 Tax = Sorghum bicolor RepID = C5XXW4_SORBI (2e−10) | 6 | 57.1 | 128501719 | 128502463 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 185 | Putative wall-associated serine/threonine kinase n = 1 Tax = Oryza sativa Japonica Group RepID = Q6ZK05_ORYSJ (1e-177); Pkinase: Protein kinase domain (2.2e-39); Pkinase_Tyr: Protein tyrosine kinase (3.6e-34); GO_MF:GO:0016301, kinase activity# (1e-177); GO_BP:GO:0016301, kinase activity# (1e-177) | 6 | 57.1 | 128520533 | 128525078 |
| 186 | Lactoylglutathione lyase n = 1 Tax = Zea mays RepID = B6UGW8_MAIZE (2e-92); Glyoxalase: Glyoxalase/Bleomycin resistance protein/Dioxygenase superfamily (7e-07); GO_MF:GO:0016829, lyase activity# (2e-92) | 6 | 57.1 | 128580829 | 128583989 |
| 187 | Isoform 2 of Probable protein phosphatase 2C 48 n = 1 Tax = Oryza sativa Japonica Group RepID = Q6L482-2 (3e-10); GO_MF:GO:0046872, metal ion binding# (4e-10); GO_BP:GO:0004721, phosphoprotein phosphatase activity# (4e-10) | 6 | 57.2 | 128601099 | 128602653 |
| 188 | Transposon protein, putative, CACTA, En/Spm sub-class n = 1 Tax = Oryza sativa Japonica Group RepID = Q10N80_ORYSJ (2e-50); GO_MF:GO:0004803, transposase activity# (2e-50); GO_BP:GO:0006313, transposition, DNA-mediated# (2e-50); GO_CC:GO:0005783, IDA#endoplasmic reticulum# (2e-27) | 6 | 57.2 | 128635663 | 128637800 |
| 189 | Nucleotide sugar translocator BT2A n = 4 Tax = Zea mays RepID = B2LWG5_MAIZE (0.0); Mito_carr: Mitochondrial carrier protein (6.6e-26); Mito_carr: Mitochondrial carrier protein (1.1e-34); Mito_carr: Mitochondrial carrier protein (5.9e-33); GO_MF:GO:0005488, binding# (0.0); GO_BP:GO:0055085, transmembrane transport# (0.0); GO_CC:GO:0016021, integral to membrane# (0.0) | 6 | 57.2 | 128638388 | 128642377 |
| 190 | Putative uncharacterized protein n = 1 Tax = Zea mays RepID = B6SUB9_MAIZE (4e-99) | 6 | 57.3 | 128663003 | 128666303 |
| 191 | OSJNBa053K19.6 protein n = 5 Tax = Poaceae RepID = Q7X809_ORYSJ (1e-58); GO_MF:GO:0016491, oxidoreductase activity# (1e-58); GO_BP:GO:0055114, oxidation reduction# (1e-58); GO_CC:GO:0005777, IDA#peroxisome# (1e-44) | 6 | 57.3 | 128667645 | 128669160 |
| 192 | Phospholipase D alpha 1 n = 7 Tax = Poaceae RepID = PLDA1_ORYSJ (0.0); PLDc: Phospholipase D. Active site motif (1.2e-09); PLDc: Phospholipase D. Active site motif (1.4e-08); GO_MF:GO:0005509, calcium ion storage activity# (0.0); GO_BP:GO:0046470, phosphatidylcholine metabolic process# (0.0); GO_CC:GO:0016020, membrane# (0.0) | 6 | 57.4 | 128722429 | 128725039 |
| 193 | Putative uncharacterized protein n = 1 Tax = Zea mays RepID = B4FWV4_MAIZE (4e-69) | 6 | 57.4 | 128734831 | 128736354 |
| 194 | CDPK-related protein kinase n = 1 Tax = Zea mays RepID = B6SYP7_MAIZE (2e-67); Pkinase: Protein kinase domain (3.2e-09); Pkinase_Tyr: Protein tyrosine kinase (3.5e-06); WD40: WD domain, G-beta repeat (0.011); WD40: WD domain, G-beta repeat (0.0046); GO_MF:GO:0016740, transferase activity# (9e-87); GO_BP:GO:0016301, kinase activity# (9e-87); GO_CC:GO:0005886, plasma membrane# (1e-55) | 6 | 57.5 | 128754439 | 128759348 |
| 195 | Putative uncharacterized protein n = 2 Tax = Zea mays RepID = Q5GAU8_MAIZE (9e-27) | 6 | 57.5 | 128781974 | 128782353 |
| 196 | NBS-LRR class disease resistance protein n = 1 Tax = Oryza sativa Japonica Group RepID = B5UBC0_ORYSJ (0.0); NB-ARC: NB-ARC domain (1.1e-35); GO_MF:GO:0017111, nucleoside-triphosphatase activity# (0.0); GO_BP:GO:0006952, defense response# (0.0) | 6 | 57.5 | 128790205 | 128798880 |
| 197 | Putative uncharacterized protein n = 2 Tax = Zea mays RepID = B6TX07_MAIZE (1e-112); IQ: IQ calmodulin-binding motif (7.9e-05); IQ: IQ calmodulin-binding motif (0.0012) | 6 | 57.6 | 128819708 | 128821261 |
| 198 | Putative Mla1 n = 1 Tax = Sorghum bicolor RepID = Q8LJZ8_SORBI (1e-143); NB-ARC: NB-ARC domain (1.4e-57); NACHT: NACHT domain (0.036); LRR_1: Leucine Rich Repeat (9); LRR_1: Leucine Rich Repeat (2.4); LRR_1: Leucine Rich Repeat (1.6); LRR_1: Leucine Rich Repeat (45); LRR_1: Leucine Rich Repeat (3e+02); LRR_1: Leucine Rich Repeat (43); GO_MF:GO:0005524, ATP binding# (1e-149); GO_BP:GO:0006952, defense response# (1e-149) | 6 | 57.6 | 128825273 | 128833947 |
| 199 | Putative RGH1A n = 1 Tax = Oryza sativa Japonica Group RepID = Q6Z021_ORYSJ (1e-16); GO_MF:GO:0005524, ATP binding# (1e-16); GO_BP:GO:0006952, defense response# (1e-16) | 6 | 57.6 | 128827662 | 128828455 |
| 200 | Putative serine/threonine protein kinase (Fragment) n = 1 Tax = Oryza sativa Japonica Group RepID = Q84P73_ORYSJ (9e-16); GO_MF:GO:0005524, ATP binding# (4e-17); GO_BP:GO:0016567, IGI#protein ubiquitination# (4e-17); GO_CC:GO:0000151, ubiquitin ligase complex# (4e-17) | 6 | 57.6 | 128927057 | 128927892 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 201 | Putative Avr9/Cf-9 rapidly elicited protein n = 1 Tax = *Oryza sativa* Japonica Group RepID = Q6EUK7_ORYSJ (1e-09); GO_MF:GO:0005488, binding# (1e-09); GO_BP:GO:0016567, IGI#protein ubiquitination# (1e-09), GO_CC:GO:0000151, ubiquitin ligase complex# (1e-09) | 6 | 57.6 | 129025487 | 129026094 |
| 202 | H0716A07.11 protein n = 1 Tax = *Oryza sativa* RepID = Q01MA7_ORYSA (0.0); Inhibitor_I9: Peptidase inhibitor I9 (1.2e-19); Peptidase_S8: Subtilase family (3.6e-10); PA: PA domain (9.8e-05); GO_MF:GO:0043086, negative regulation of catalytic activity# (0.0); GO_BP:GO:0043086, negative regulation of catalytic activity# (0.0); GO_CC:GO:0009505, IDA#expansin# (1e-153) | 6 | 57.6 | 129031227 | 129036927 |
| 203 | Inositol-3-phosphate synthase n = 16 Tax = Magnoliophyta RepID = INO1_ORYSJ (1e-27); GO_MF:GO:0016853, isomerase activity# (1e-27); GO_BP:GO:0008654, phospholipid biosynthetic process# (1e-27); GO_CC:GO:0005737, cytoplasm# (1e-27) | 6 | 57.6 | 129042421 | 129042715 |
| 204 | Inositol-3-phosphate synthase n = 16 Tax = Magnoliophyta RepID = INO1_ORYSJ (1e-108); NAD_binding_5: Myo-inositol-1-phosphate synthase (3.4e-08); Inos-1-P_synth: Myo-inositol-1-phosphate synthase (2.2e-61); GO_MF:GO:0016853, isomerase activity# (1e-108); GO_BP:GO:0008654, phospholipid biosynthetic process# (1e-108); GO_CC:GO:0005737, cytoplasm# (1e-108) | 6 | 57.6 | 129042809 | 129044242 |
| 205 | Leaf senescence related protein-like n = 2 Tax = *Oryza sativa* RepID = Q69RQ8_ORYSJ (2e-18); IBB: Importin beta binding domain (0.076); GO_MF:GO:0008565, protein transporter activity# (1e-14); GO_BP:GO:0015031, protein transport# (1e-14); GO_CC:GO:0048471, ISS#perinuclear region of cytoplasm# (1e-14) | 6 | 57.6 | 129045552 | 129049517 |
| 206 | Xylanase inhibitor protein 1 n = 1 Tax = *Zea mays* RepID = B6U2X8_MAIZE (1e-170); Glyco_hydro_18: Glycosyl hydrolases family 18 (1.2e-19); GO_MF:GO:0043169, cation binding# (1e-170); GO_BP:GO:0045493, xylan catabolic process# (1e-170); GO_CC:GO:0005576, extracellular region# (2e-87) | 6 | 57.6 | 129086009 | 129087210 |
| 207 | Putative uncharacterized protein n = 1 Tax = *Oryza sativa* Indica Group RepID = A2YUK8_ORYSI (1e-15) | 6 | 57.6 | 129126147 | 129126488 |
| 208 | Putative transposon protein n = 1 Tax = *Oryza sativa* Japonica Group RepID = Q8H801_ORYSJ (3e-31); Transposase_23: TNP1/EN/SPM transposase (6.2e-05) | 6 | 57.6 | 129127693 | 129129065 |
| 209 | Putative uncharacterized protein Sb05g026840 n = 1 Tax = *Sorghum bicolor* RepID = C5Y811_SORBI (0.0); DUF594: Protein of unknown function, DUF594 (1.6e-30); GO_MF:GO:0046872, metal ion binding# (1e-115); GO_BP:GO:0006278, RNA-dependent DNA replication# (1e-51) | 6 | 57.6 | 129138400 | 129140529 |
| 210 | Retrotransposon protein, putative, unclassified n = 1 Tax = *Oryza sativa* Japonica Group RepID = Q2QQR5_ORYSJ (3e-33); zf-CCHC: Zinc knuckle (0.015); GO_MF:GO:0008270, zinc ion binding# (2e-49); GO_BP:GO:0006278, RNA-dependent DNA replication# (3e-40) | 6 | 57.6 | 129142269 | 129144473 |
| 211 | HAT family dimerisation domain containing protein n = 1 Tax = *Oryza sativa* Japonica Group RepID = Q2R0F0_ORYSJ (1e-107); zf-BED: BED zinc finger (1.4e-09); hATC: hAT family dimerisation domain (1.5e-28); GO_MF:GO:0046983, protein dimerization activity# (1e-116); GO_BP:GO:0006350, transcription# (1e-33) | 6 | 57.7 | 129169527 | 129171992 |
| 212 | Triose phosphate/phosphate translocator, non-green plastid, chloroplast, putative n = 1 Tax = *Ricinus communis* RepID = B9RB11_RICCO (1e-116); UAA: UAA transporter family (0.0016); DUF6: Integral membrane protein DUF6 (1.2e-11); DUF6: Integral membrane protein DUF6 (0.0068); TPT: Triose-phosphate Transporter family (3.5e-52); GO_MF:GO:0005215, transporter activity# (1e-146); GO_BP:GO:0006810, transport# (1e-146); GO_CC:GO:0016021, integral to membrane# (1e-146) | 6 | 57.7 | 129222041 | 129225144 |
| 213 | Putative transcription regulatory protein n = 2 Tax = *Oryza sativa* RepID = Q94LQ9_ORYSJ (2e-68); U-box: U-box domain (0.0089); GO_MF:GO:0016301, kinase activity# (2e-79); GO_BP:GO:0016301, kinase activity# (2e-79); GO_CC:GO:0000151, ubiquitin ligase complex# (3e-25) | 6 | 57.7 | 129243446 | 129247172 |
| 214 | NADH-ubiquinone oxidoreductase 10.5 kDa subunit n = 4 Tax = Andropogoneae RepID = B6TDN0_MAIZE (2e-31); L51_S25_CI-B8: Mitochondrial ribosomal protein L51/S25/CI-B8 domain (2e-15); GO_MF:GO:0016491, oxidoreductase activity# (4e-18); GO_BP:GO:0055114, oxidation reduction# (4e-18); GO_CC:GO:0045271, IDA#respiratory chain complex I# (4e-21) | 6 | 57.8 | 129361190 | 129365442 |
| 215 | Putative uncharacterized protein n = 1 Tax = *Zea mays* RepID = B6TDS4_MAIZE (1e-09) | 6 | 57.9 | 129437152 | 129437697 |

TABLE 18-continued

Annotated coding sequences within ASR-6.01 region.

| Gene ID | Annotation | Chr | MON Map cM† | Physical Map Position bp †† Start | End |
|---|---|---|---|---|---|
| 216 | Putative receptor protein kinase n = 1 Tax = Oryza sativa Japonica Group RepID = Q65XS7_ORYSJ (0.0); LRRNT_2: Leucine rich repeat N-terminal domain (6.8e–13); LRR_1: Leucine Rich Repeat (3.2); LRR_1: Leucine Rich Repeat (0.91); LRR_1: Leucine Rich Repeat (0.11); LRR_1: Leucine Rich Repeat (5.8); LRR_1: Leucine Rich Repeat (12); LRR_1: Leucine Rich Repeat (41); LRR_1: Leucine Rich Repeat (1.2); LRR_1: Leucine Rich Repeat (4.3); LRR_1: Leucine Rich Repeat (0.09); LRR_1: Leucine Rich Repeat (2.5); LRR_1: Leucine Rich Repeat (0.11); LRR_1: Leucine Rich Repeat (1.2); LRR_1: Leucine Rich Repeat (0.21); LRR_1: Leucine Rich Repeat (2.3); LRR_1: Leucine Rich Repeat (2.8); LRR_1: Leucine Rich Repeat (0.13); LRR_1: Leucine Rich Repeat (0.1); LRR_1: Leucine Rich Repeat (0.29); LRR_1: Leucine Rich Repeat (0.13); LRR_1: Leucine Rich Repeat (0.44); LRR_1: Leucine Rich Repeat (1.7); LRR_1: Leucine Rich Repeat (0.041); LRR_1: Leucine Rich Repeat (0.26); LRR_1: Leucine Rich Repeat (0.21); LRR_1: Leucine Rich Repeat (0.96); LRR_1: Leucine Rich Repeat (14); LRR_1: Leucine Rich Repeat (0.94); LRR_1: Leucine Rich Repeat (0.092); LRR_1: Leucine Rich Repeat (0.25); LRR_1: Leucine Rich Repeat (5.5); LRR_1: Leucine Rich Repeat (6); LRR_1: Leucine Rich Repeat (12); LRR_1: Leucine Rich Repeat (0.33); LRR_1: Leucine Rich Repeat (5.1); LRR_1: Leucine Rich Repeat (0.078); LRR_1: Leucine Rich Repeat (2.2); LRR_1: Leucine Rich Repeat (3.4); LRR_1: Leucine Rich Repeat (0.56); LRR_1: Leucine Rich Repeat (1.2); LRR_1: Leucine Rich Repeat (3.3); LRR_1: Leucine Rich Repeat (2.7); LRR_1: Leucine Rich Repeat (47); LRR_1: Leucine Rich Repeat (0.85); GO_MF:GO:0016301, kinase activity# (0.0); GO_BP:GO:0016301, kinase activity# (0.0); GO_CC:GO:0016021, integral to membrane# (0.0) | 6 | 57.95 | 129472709 | 129517525 |
| 217 | BEL1-related homeotic protein 30 n = 2 Tax = Andropogoneae RepID = B6SWM4_MAIZE (1e–64); GO_MF:GO:0043565, sequence-specific DNA binding# (1e–64); GO_BP:GO:0045449, regulation of transcription# (1e–64); GO_CC:GO:0005634, nucleus# (1e–64) | 6 | 58 | 129501726 | 129502856 |
| 218 | HAT family dimerization domain protein n = 2 Tax = Oryza sativa RepID = D0UZH7_ORYSJ (6e–94); GO_MF:GO:0046983, protein dimerization activity# (3e–86) | 6 | 58 | 129520475 | 129521414 |
| 219 | Putative uncharacterized protein n = 1 Tax = Zea mays RepID = C0PP88_MAIZE (1e–46) | 6 | 58 | 129538411 | 129540061 |
| 220 | Putative uncharacterized protein Sb01g027800 n = 1 Tax = Sorghum bicolor RepID = C5WQN1_SORBI (3e–13) | 6 | 58 | 129581574 | 129582554 |
| 221 | Alliin lyase n = 3 Tax = Zea mays RepID = B6TK37_MAIZE (0.0); Aminotran_1_2: Aminotransferase class I and II (0.006); Allinase_C: Allinase, C-terminal domain (4.8e–199); GO_MF:GO:0030170, pyridoxal phosphate binding# (0.0); GO_BP:GO:0080022, LMP#primary root development# (9e–82); GO_CC:GO:0005737, cytoplasm# (9e–82) | 6 | 58 | 129661095 | 129664534 |
| 222 | O-sialoglycoprotein endopeptidase, putative n = 2 Tax = rosids RepID = B9T542_RICCO (1e–164); Peptidase_M22: Glycoprotease family (6.3e–73); GO_MF:GO:0008270, zinc ion binding# (0.0); GO_BP:GO:0006508, proteolysis# (0.0); GO_CC:GO:0005737, cytoplasm# (1e–125) | 6 | 58 | 129670272 | 129674945 |
| 223 | HAT family dimerisation domain containing protein n = 2 Tax = Oryza sativa Japonica Group RepID = Q7XF06_ORYSJ (1e–44); hATC: hAT family dimerisation domain (1e–11); GO_MF:GO:0046983, protein dimerization activity# (7e–52); GO_BP:GO:0006350, transcription# (7e–52) | 6 | 58 | 129679558 | 129681972 |
| 224 | Nonspecific lipid-transfer protein n = 2 Tax = Zea mays RepID = B6SZZ6_MAIZE (6e–29); Tryp_alpha_amyl: Protease inhibitor/seed storage/LTP f (8.5e–10); GO_MF:GO:0008289, lipid binding# (3e–13); GO_BP:GO:0006869, lipid transport# (6e–29) | 6 | 58 | 129703134 | 129703976 |
| 225 | Stem 28 kDa glycoprotein n = 1 Tax = Zea mays RepID = B6T003_MAIZE (1e–147); Acid_phosphat_B: HAD superfamily, subfamily IIIB (Acid (3.6e–90); GO_MF:GO:0003993, acid phosphatase activity# (1e–147); GO_BP:GO:0003993, acid phosphatase activity# (1e–147); GO_CC:GO:0005886, plasma membrane# (1e–51) | 6 | 58.2 | 129792745 | 129795009 |
| 226 | Serine-threonine protein kinase, plant-type, putative n = 1 Tax = Ricinus communis RepID = B9RKF0_RICCO (1e–105); LRRNT_2: Leucine rich repeat N-terminal domain (2.6e–06); LRR_1: Leucine Rich Repeat (3.9); LRR_1: Leucine Rich Repeat (1.8); LRR_1: Leucine Rich Repeat (5.4); LRR_1: Leucine Rich Repeat (70); LRR_1: Leucine Rich Repeat (32); LRR_1: Leucine Rich Repeat (2.1e+02); LRR_1: Leucine Rich Repeat (0.72); LRR_1: Leucine Rich Repeat (0.23); LRR_1: Leucine Rich Repeat (1.4e+02); GO_MF:GO:0005515, protein | 6 | 58.3 | 129841439 | 129842719 |

TABLE 18-continued

Annotated coding sequences within ASR-6.01 region.

| Gene ID | Annotation | Chr | MON Map cM † | Physical Map Position bp †† Start | End |
|---|---|---|---|---|---|
| 227 | binding# (1e-141); GO_BP:GO:0055114, oxidation reduction# (1e-105); GO_CC:GO:0009505, IDA#expansin# (2e-68) | 6 | 58.3 | 129880459 | 129880719 |
| 228 | Retrotransposon protein, putative, Ty1-copia subclass n = 2 Tax = Oryza sativa RepID = Q7XH58_ORYSJ (6e-28); GO_MF:GO:0003677, DNA binding# (6e-28); GO_BP:GO:0015074, DNA integration# (6e-28) | 6 | 58.3 | 129887372 | 129887779 |
| 229 | OSJNBa0064G10.18 protein n = 3 Tax = Oryza sativa RepID = Q7XKB3_ORYSJ (7e-94); WD40: WD domain, G-beta repeat (1.6); WD40: WD domain, G-beta repeat (0.016); WD40: WD domain, G-beta repeat (3e-09); WD40: WD domain, G-beta repeat (3.4e-12); WD40: WD domain, G-beta repeat (2.6e-10); GO_MF:GO:0016740, transferase activity# (5e-92); GO_BP:GO:0016905, myosin heavy chain kinase activity# (2e-84); GO_CC:GO:0005874, microtubule# (1e-89) | 6 | 58.35 | 129888300 | 129891431 |
| 230 | SIN3 component, histone deacetylase complex n = 1 Tax = Populus trichocarpa RepID = B9HU88_POPTR (2e-15); GO_MF:GO:0016564, transcription repressor activity## (1e-12); GO_BP:GO:0006355, regulation of transcription, DNA-dependent# (5e-21); GO_CC:GO:0005634, nucleus# (5e-21) | 6 | 58.4 | 129892633 | 129892893 |
| 231 | L-lactate dehydrogenase n = 3 Tax = Oryza sativa RepID = Q0E4Q5_ORYSJ (1e-51); Ldh_1_C: lactate/malate dehydrogenase, alpha/b (7.2e-05); GO_MF:GO:0016616, oxidoreductase activity, acting on the CH—OH group of donors, NAD or NADP as acceptor# (1e-51); GO_BP:GO:0055114, oxidation reduction# (1e-51); GO_CC:GO:0005737, cytoplasm# (1e-51) | 6 | 58.4 | 129892886 | 129893304 |
| 232 | Derlin-1.2 n = 2 Tax = Zea mays RepID = DER12_MAIZE (1e-137); DER1: Der1-like family (2.5e-56); GO_MF:GO:0005515, protein binding# (3e-35); GO_BP:GO:0006950, response to stress# (1e-137); GO_CC:GO:0016021, integral to membrane# (1e-137) | 6 | 58.4 | 129897727 | 129902466 |
| 233 | Putative uncharacterized protein n = 1 Tax = Zea mays RepID = B6UF52_MAIZE (1e-14) | 6 | 58.5 | 129955339 | 129955661 |
| 234 | OSJNBa0036E02.10 protein n = 2 Tax = Oryza sativa RepID = Q7F7E1_ORYSJ (7e-35); IQ: IQ calmodulin-binding motif (0.0013); IQ: IQ calmodulin-binding motif (0.006) | 6 | 58.5 | 129963265 | 129965399 |
| 235 | Hexokinase-1 n = 2 Tax = Zea mays RepID = B6TL75_MAIZE (0.0); Hexokinase_1: Hexokinase (2.9e-09); Hexokinase_2: Hexokinase (4e-79); GO_MF:GO:0016773, phosphotransferase activity, alcohol group as acceptor# (0.0); GO_BP:GO:0016301, kinase activity# (0.0); GO_CC:GO:0005737, cytoplasm# (1e-152) | 6 | 58.5 | 129979002 | 129982104 |
| 236 | Retrotransposon protein, putative, unclassified n = 1 Tax = Oryza sativa Japonica Group RepID = Q7XE51_ORYSJ (7e-30); zf-CCHC: Zinc knuckle (0.0013); zf-CCHC: Zinc knuckle (0.16); GO_MF:GO:0008270, zinc ion binding# (7e-44); GO_BP:GO:0006278, RNA-dependent DNA replication# (4e-35) | 6 | 58.5 | 129986022 | 129989105 |
| 237 | IAA16-auxin-responsive Aux/IAA family member n = 2 Tax = Zea mays RepID = B6TT61_MAIZE (5e-89); AUX_IAA: AUX/IAA family (2.4e-19); GO_MF:GO:0046983, protein dimerization activity## (5e-89); GO_BP:GO:0045449, regulation of transcription# (5e-89); GO_CC:GO:0005634, nucleus# (5e-89) | 6 | 58.6 | 130004376 | 130008214 |
| 238 | Os07g0695700 protein n = 1 Tax = Oryza sativa Japonica Group RepID = Q0D3B3_ORYSJ (1e-12) | 6 | 58.6 | 130011779 | 130011936 |
| 239 | Histidine-containing phosphotransfer protein 4 n = 2 Tax = Andropogoneae RepID = B6SRE6_MAIZE (2e-50); Hpt: Hpt domain (1.7e-08); GO_MF:GO:0004871, signal transducer activity## (7e-65); GO_BP:GO:0004871, signal transducer activity# (7e-65); GO_CC:GO:0005737, cytoplasm# (2e-38) | 6 | 58.6 | 130159712 | 130161359 |
| 240 | OSJNBa0027O01.13 protein n = 3 Tax = Oryza sativa RepID = Q7XXC5_ORYSJ (0.0); NCD3G: Nine Cysteines Domain of family 3 GPC (0.093); GO_CC:GO:0005773, IDA#vacuole# (0.0) | 6 | 58.6 | 130239488 | 130245375 |
| 241 | Putative polyprotein n = 1 Tax = Zea mays RepID = Q8SA93_MAIZE (3e-59); GO_MF:GO:0003964, RNA-directed DNA polymerase, group II intron encoded# (3e-59); GO_BP:GO:0015074, DNA integration# (3e-59); GO_CC:GO:0005634, nucleus# (3e-59) | 6 | 58.6 | 130257021 | 130258701 |

† cM = centiMorgans.
†† bp = base pair of Arizona Genomics Institute B73 RefGen_v2 sequence.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method of obtaining a corn plant with enhanced anthracnose stalk rot resistance, said method comprising:
   a) obtaining a DNA sample from at least one corn plant or part thereof from a population of corn plants;
   b) detecting in the DNA sample the presence of an anthracnose stalk rot resistance allele, wherein said allele is within 5 cM of a "C" corresponding to position 101 of SEQ ID NO:96, and wherein the "C" at said position is associated with enhanced anthracnose stalk rot resistance;
   c) selecting at least a first plant comprising said allele and enhanced anthracnose stalk rot resistance compared to a plant lacking said allele;
   d) crossing the plant selected in step c) with a second corn plant, wherein said second corn plant lacks or is heterozygous for said anthracnose stalk rot resistance allele;
   e) collecting seeds from the cross of step d); and
   f) growing at least one progeny corn plant from the seeds of step e); wherein said progeny corn plant comprises said allele and has enhanced anthracnose stalk rot resistance compared to a corn plant lacking said allele.

2. The method of claim 1, wherein said selecting comprises detecting a polymorphism located in a chromosomal segment flanked by marker loci TIDP3136 and pzb00414.

3. The method of claim 2, wherein said polymorphism is located in a chromosomal segment flanked by marker loci SEQ ID NOs:4 and 54.

4. The method of claim 2, wherein said polymorphism is located in a chromosomal segment flanked by marker loci SEQ ID NO: 52 and SEQ ID NO: 8.

5. The method of claim 4, wherein said chromosomal segment is flanked by marker loci SEQ ID NO: 52 and SEQ ID NO: 106.

6. The method of claim 5, wherein said chromosomal segment is flanked by marker loci SEQ ID NO: 82 and SEQ ID NO: 97.

7. The method of claim 1, wherein the selecting comprises detecting enhanced anthracnose stalk rot resistance, wherein the detecting enhanced anthracnose stalk rot resistance comprises detecting a polynucleotide comprising SEQ ID NO:96 in the DNA sample.

* * * * *